United States Patent
Xu et al.

(10) Patent No.: US 11,958,856 B2
(45) Date of Patent: Apr. 16, 2024

(54) SUBSTITUTED 1,2,3,8,9,9A-HEXAHYDRO-5H-PYRROLO[1,2-A]AZEPIN-5-ONES AS FACTOR XIA INHIBITORS

(71) Applicant: Janssen Pharmaceutica NV, Beerse (BE)

(72) Inventors: Guozhang Xu, Chesterbrook, PA (US); Zhijie Liu, Paoli, PA (US)

(73) Assignee: Janssen Pharmaceutica NV, Beerse (BE)

( * ) Notice: Subject to any disclaimer, the term of this patent is extended or adjusted under 35 U.S.C. 154(b) by 0 days.

(21) Appl. No.: 17/870,142

(22) Filed: Jul. 21, 2022

(65) Prior Publication Data
US 2023/0067355 A1    Mar. 2, 2023

Related U.S. Application Data

(60) Provisional application No. 63/224,426, filed on Jul. 22, 2021.

(51) Int. Cl.
| A61K 31/55 | (2006.01) |
| A61K 9/48 | (2006.01) |
| C07D 223/14 | (2006.01) |
| C07D 487/04 | (2006.01) |

(52) U.S. Cl.
CPC .......... *C07D 487/04* (2013.01); *A61K 9/4858* (2013.01)

(58) Field of Classification Search
CPC .............................. A61K 31/55; C07D 223/14
USPC ....................................... 514/214.01; 540/593
See application file for complete search history.

(56) References Cited

U.S. PATENT DOCUMENTS

| 4,845,079 A | 7/1989 | Luly et al. |
| 4,885,292 A | 12/1989 | Ryono et al. |
| 4,894,437 A | 1/1990 | Tenbrink |
| 4,980,283 A | 12/1990 | Huang et al. |
| 5,034,512 A | 7/1991 | Hudspeth et al. |
| 5,036,053 A | 7/1991 | Himmelsbach et al. |
| 5,036,054 A | 7/1991 | Kaltenbronn et al. |
| 5,055,466 A | 10/1991 | Weller et al. |
| 5,063,207 A | 11/1991 | Doherty et al. |
| 5,063,208 A | 11/1991 | Rosenberg et al. |
| 5,064,965 A | 11/1991 | Ocain et al. |
| 5,066,643 A | 11/1991 | Abeles et al. |
| 5,071,837 A | 12/1991 | Doherty et al. |
| 5,075,451 A | 12/1991 | Ocain et al. |
| 5,089,471 A | 2/1992 | Hanson et al. |
| 5,095,119 A | 3/1992 | Ocain et al. |
| 5,098,924 A | 3/1992 | Poss |
| 5,104,869 A | 4/1992 | Albright et al. |
| 5,106,835 A | 4/1992 | Albright et al. |
| 5,114,937 A | 5/1992 | Hamby et al. |
| 5,116,835 A | 5/1992 | Ruger et al. |
| 6,063,847 A | 5/2000 | Chackalamannil et al. |
| 6,326,380 B1 | 12/2001 | Chackalamannil et al. |
| 6,645,987 B2 | 11/2003 | Chackalamannil et al. |
| 7,037,920 B2 | 5/2006 | Chackalamannil et al. |
| 7,235,567 B2 | 6/2007 | Wu |
| 7,304,078 B2 | 12/2007 | Chackalamannil et al. |
| 9,732,085 B2 | 8/2017 | Courtney et al. |
| 2023/0067355 A1* | 3/2023 | Xu ....................... A61K 9/0053 |

FOREIGN PATENT DOCUMENTS

| EP | 1294714 B1 | 8/2007 |
| EP | 1495018 B1 | 11/2007 |
| WO | 94/03479 A1 | 2/1994 |
| WO | 01/40231 A1 | 6/2001 |
| WO | 01/96330 A2 | 12/2001 |

OTHER PUBLICATIONS

Jordan, V. C. Nature Reviews: Drug Discovery, 2, 2003, 205.*
Dörwald, F. Zaragoza. Side Reactions in Organic Synthesis: A Guide to Successful Synthesis Design, Weinheim: Wiley-VCH Verlag GmbH & Co. KGaA, 2005, Preface.*
Hackam, et al. JAMA, 296(14), 2006, 1731-1732.*
Bernatowicz et al., Development of Potent Thrombin Receptor Antagonist Peptides, J. Med. Chem., 1996, vol. 39, 4879-4887.
Bundgaard, "Design of Prodrugs: Bioreversible derivative for various functional groups and chemical entities", Elsevier, 1985, 1-96.
Chou et al., "Theoretical Basis, Experimental Design, and Computerized Simulation of Synergism and Antagonism in Drug Combination Studies", Pharmacol. Rev., 2006, 58, 621-681.
Gailani et al., "Intrinsic Pathway of Coagulation and Arterial Thrombosis", Arterioscler. Throm. Vasc. Biol., 2007, 27, 2507-2513.
Hoffman, "A cell-based model of coagulation and the role of factor VIIa", Blood Reviews, 2003, 17, S1-S5.
Howard et al., "Factor IXa Inhibitors as Novel Anticoagulents", Arterioscler Thromb. Vasc. Biol., 2007, 27, 722-727.
Quan et al., "Factor XIa Inhibitors as New Anticoagulants", J. Med. Chem. 2018, vol. 61, 7425-7447.

* cited by examiner

*Primary Examiner* — Douglas M Willis
(74) *Attorney, Agent, or Firm* — BakerHostetler

(57) ABSTRACT

A compound of formula (I) or a pharmaceutically acceptable salt or stereoisomer thereof:

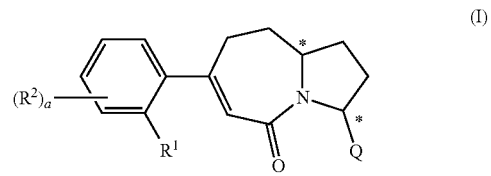

Pharmaceutical compositions containing said compounds, and the use of said compounds in the treatment and/or prophylaxis of thromboembolic disorders, inflammatory disorders and diseases or conditions in which plasma kallikrein activity is implicated.

16 Claims, No Drawings

SUBSTITUTED 1,2,3,8,9,9A-HEXAHYDRO-5H-PYRROLO[1,2-A] AZEPIN-5-ONES AS FACTOR XIA INHIBITORS

CROSS REFERENCE TO RELATED APPLICATIONS

This application claims benefit of U.S. Provisional Application No. 63/224,426, filed Jul. 22, 2021, the disclosure of which is incorporated by reference herein.

FIELD OF THE INVENTION

The present invention is directed 1,2,3,8,9,9a-hexahydro-5H-pyrrolo[1,2-a]azepin-5-one derivatives, stereoisomers, isotopologues, and pharmaceutically acceptable salts thereof, pharmaceutical compositions containing said compounds, and the use of said compounds in the treatment and/or prophylaxis of thromboembolic disorders, inflammatory disorders and diseases or conditions in which plasma kallikrein activity is implicated.

BACKGROUND OF THE INVENTION

Thromboembolic diseases remain the leading cause of death in developed countries despite the availability of anticoagulants such as warfarin (COUMADIN®), heparin, low molecular weight heparins (LMWH), and synthetic penta-saccharides and antiplatelet agents such as aspirin and clopidogrel (PLAVIX®). The oral anticoagulant warfarin inhibits the post-translational maturation of coagulation factors VII, IX, X and prothrombin, and has proven effective in both venous and arterial thrombosis. However, its usage is limited due to its narrow therapeutic index with respect to bleeding safety, slow onset of therapeutic effect, numerous dietary and drug-drug interactions, and a need for monitoring and dose adjustment. Novel oral anticoagulants directly targeting either thrombin or factor Xa, e.g., dabigatran, apixaban, betrixaban, edoxaban, rivaroxaban, have been approved for both venous and arterial indications. However, the risk of bleeding is not completely eliminated, and can be as high as 2-3% per year in patients with atrial fibrillation (Quan et al., J. Med. Chem. 2018, pp 7425-7447, Vol. 61). Thus, discovering and developing safe and efficacious oral anticoagulants with minimal impacts on hemostasis for the prevention and treatment of a wide range of thromboembolic disorders has become increasingly important.

SUMMARY OF THE INVENTION

The present invention is directed to compounds of formula (I)

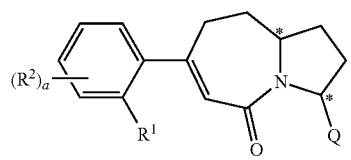

(I)

wherein
$R^1$ is selected from the group consisting of halogen, hydroxy, $C_{1-4}$alkyl, fluorinated $C_{1-4}$alkyl, $C_{1-4}$alkoxy, fluorinated $C_{1-4}$alkoxy, cyano, nitro, $-NR^A R^B$, $-C(O)-C_{1-4}$alkyl, $C_{3-6}$cycloalkyl, phenyl and 5 to 6 membered heterocyclyl;

wherein the $C_{3-6}$cycloalkyl, phenyl or 5 to 6 membered heterocyclyl is optionally substituted with one or more substituents independently selected from the group consisting of halogen, hydroxy, cyano, $C_{1-4}$alkyl, fluorinated $C_{1-4}$alkyl, $C_{1-4}$alkoxy, fluorinated $C_{1-4}$alkoxy, $-C(O)OH$, $-C(O)O-(C_{1-4}$alkyl), $-NR^A R^B$, $-(C_{1-4}$alkylene)-$NR^A R^B$, $C_{3-7}$cycloalkyl and 5 to 6 membered heterocyclyl;

and wherein $R^A$ and $R^B$ are each independently selected from the group consisting of hydrogen and $C_{1-4}$alkyl;

a is an integer from 0 to 3;

each $R^2$ is independently selected from the group consisting of chloro, fluoro, methyl and methoxy;

Q is selected from the group consisting of

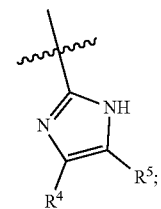

(a)

wherein $R^4$ is selected from the group consisting of hydrogen, and halogen;

wherein $R^5$ is selected from the group consisting of phenyl and 5 to 6 membered heteroaryl;

wherein the phenyl or 5 to 6 membered heteroaryl is optionally substituted with one to two substituents independently selected from the group consisting of halogen, $C_{1-4}$alkyl, fluorinated $C_{1-2}$alkyl, hydroxy substituted $C_{1-2}$alkyl, $-C(O)OH$, $-C(O)O-(C_{1-4}$alkyl), $-NR^C R^D$, $-C(O)-NR^C R^D$ and $-NR^C-C(O)-(C_{1-2}$alkyl); and wherein $R^C$ and $R^D$ are each independently selected from the group consisting of hydrogen, $C_{1-2}$alkyl and hydroxy substituted $C_{1-4}$alkyl;

and

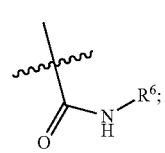

(b)

wherein $R^6$ is selected from the group consisting of phenyl and 9 to 10 membered heteroaryl;

wherein the phenyl or 9 to 10 membered heteroaryl is optionally substituted with one to two substituents independently selected from the group consisting of halogen, $C_{1-4}$alkyl, fluorinated $C_{1-2}$alkyl, hydroxy substituted $C_{1-2}$alkyl, $-C(O)OH$, $-C(O)O-(C_{1-4}$alkyl), $-NR^C R^D$, $-C(O)-NR^E R^F$, and $-NR^C-C(O)-(C_{1-2}$alkyl); wherein $R^E$ and $R^F$ are each independently selected from the group consisting of hydrogen and $C_{1-4}$alkyl;

and stereoisomers, isotopologues, and pharmaceutically acceptable salts thereof.

The present invention is further directed to processes for the preparation of the compounds of formula (I). The present invention is further directed to a compound of formula (I) prepared according to any of the process(es) described herein.

Illustrative of the invention are pharmaceutical compositions comprising a pharmaceutically acceptable carrier and a compound of formula (I) as described herein. An illustration of the invention is a pharmaceutical composition made by mixing a compound of formula (I) as described herein and a pharmaceutically acceptable carrier. Illustrating the invention is a process for making a pharmaceutical composition comprising mixing a compound of formula (I) as described herein and a pharmaceutically acceptable carrier.

Exemplifying the invention are methods for the treatment and/or prophylaxis of thromboembolic disorders, inflammatory disorders or diseases or conditions in which plasma kallikrein activity is implicated, as described herein, comprising administering to a subject in need thereof a therapeutically effective amount of any of the compounds or pharmaceutical compositions described above.

Exemplifying the invention are methods or the treatment and/or prophylaxis of thromboembolic disorders, such as arterial cardiovascular thromboembolic disorders, venous cardiovascular thromboembolic disorders, arterial cerebrovascular thromboembolic disorders, and venous cerebrovascular thromboembolic disorders, comprising administering to a subject in need thereof a therapeutically effective amount of any of the compounds or pharmaceutical compositions described above. Examples of thromboembolic disorders include, but are not limited to, unstable angina, an acute coronary syndrome, atrial fibrillation, first myocardial infarction, recurrent myocardial infarction, ischemic sudden death, transient ischemic attack, stroke, atherosclerosis, peripheral occlusive arterial disease, venous thrombosis, deep vein thrombosis, thrombophlebitis, arterial embolism, coronary arterial thrombosis, cerebral arterial thrombosis, cerebral embolism, kidney embolism, pulmonary embolism, and thrombosis resulting from medical implants, devices, or procedures in which blood is exposed to an artificial surface that promotes thrombosis.

In an embodiment, the present invention is directed to a compound of formula (I) for use as a medicament. In another embodiment, the present invention is directed to a compound of formula (I) for use in the treatment and/or prophylaxis of thromboembolic disorders, inflammatory disorders or diseases or conditions in which plasma kallikrein activity is implicated.

In another embodiment, the present invention is directed to a compound of formula (I) for use in the treatment and/or prophylaxis of a thromboembolic disorder, such as arterial cardiovascular thromboembolic disorders, venous cardiovascular thromboembolic disorders, arterial cerebrovascular thromboembolic disorders, and venous cerebrovascular thromboembolic disorders. In another embodiment, the present invention is directed to a compound of formula (I) for use in the treatment and/or prophylaxis of a thromboembolic disorder selected from the group consisting of unstable angina, an acute coronary syndrome, atrial fibrillation, first myocardial infarction, recurrent myocardial infarction, ischemic sudden death, transient ischemic attack, stroke, atherosclerosis, peripheral occlusive arterial disease, venous thrombosis, deep vein thrombosis, thrombophlebitis, arterial embolism, coronary arterial thrombosis, cerebral arterial thrombosis, cerebral embolism, kidney embolism, pulmonary embolism, and thrombosis resulting from medical implants, devices, or procedures in which blood is exposed to an artificial surface that promotes thrombosis. In another embodiment, the present invention is directed to a compound of formula (I) for use in the treatment and/or prophylaxis of a thromboembolic disorder selected from the group consisting of hereditary angioedema (HAE) and diabetic macular edema (DME).

In another embodiment, the present invention is directed to a composition comprising a compound of formula (I) for use in the treatment and/or prophylaxis of a disorder, disease or condition as described herein. In another embodiment, the present invention is directed to a composition comprising a compound of formula (I) for use in the treatment and/or prophylaxis of a thromboembolic disorder, and inflammatory disorder or a disease or condition in which plasma kallikrein activity is implicated.

In another embodiment, the present invention is directed to a composition comprising a compound of formula (I) for use in the treatment and/or prophylaxis of a thromboembolic disorder, such as arterial cardiovascular thromboembolic disorders, venous cardiovascular thromboembolic disorders, arterial cerebrovascular thromboembolic disorders, and venous cerebrovascular thromboembolic disorders. In another embodiment, the present invention is directed to a composition comprising a compound of formula (I) for use in the treatment and/or prophylaxis of a thromboembolic disorder selected from the group consisting of unstable angina, an acute coronary syndrome, atrial fibrillation, first myocardial infarction, recurrent myocardial infarction, ischemic sudden death, transient ischemic attack, stroke, atherosclerosis, peripheral occlusive arterial disease, venous thrombosis, deep vein thrombosis, thrombophlebitis, arterial embolism, coronary arterial thrombosis, cerebral arterial thrombosis, cerebral embolism, kidney embolism, pulmonary embolism, and thrombosis resulting from medical implants, devices, or procedures in which blood is exposed to an artificial surface that promotes thrombosis. In another embodiment, the present invention is directed to a composition comprising a compound of formula (I) for use in the treatment and/or prophylaxis of a thromboembolic disorder such as hereditary angioedema (HAE) or diabetic macular edema (DME).

Another example of the invention is the use of any of the compounds described herein in the preparation of a medicament for the treatment and/or prophylaxis of a disorder, disease or condition as described herein. Another example of the invention is the use of any of the compounds described herein in the preparation of a medicament for the treatment and/or prophylaxis of a thromboembolic disorder, an inflammatory disorder or a disease or condition in which plasma kallikrein activity is implicated.

Another example of the invention is the use of any of the compounds described herein in the preparation of a medicament for the treatment and/or prophylaxis of a thromboembolic disorder selected from the group consisting of (a) arterial cardiovascular thromboembolic disorders, (b) venous cardiovascular thromboembolic disorders, (c) arterial cerebrovascular thromboembolic disorders, and (d) venous cerebrovascular thromboembolic disorders. Another example of the invention is the use of any of the compounds described herein in the preparation of a medicament for the treatment and/or prophylaxis of (a) unstable angina, (b) an acute coronary syndrome, (c) atrial fibrillation, (d) first myocardial infarction, (e) recurrent myocardial infarction, (f) ischemic sudden death, (g) transient ischemic attack, (h) stroke, (i) atherosclerosis, (j) peripheral occlusive arterial disease, (k) venous thrombosis, (l) deep vein thrombosis, (m) thrombophlebitis, (n) arterial embolism, (o) coronary arterial thrombosis, (p) cerebral arterial thrombosis, (q) cerebral embolism, (r) kidney embolism, (s) pulmonary embolism, or (t) thrombosis resulting from medical implants, devices, or procedures in which blood is exposed to an artificial surface that promotes thrombosis. Another example of the invention is the use of any of the compounds described herein in the preparation of a medicament for the treatment and/or prophylaxis of: (a) hereditary angioedema (HAE) or (b) diabetic macular edema (DME).

Another example of the invention is the use of any of the compounds described herein for use in a method for treating a thromboembolic, inflammatory or a disease or condition in which plasma kallikrein activity is implicated as described herein, in a subject in need thereof.

Another example of the invention is the use of any of the compounds described herein for use in a method for the treatment and/or prophylaxis of (a) arterial cardiovascular thromboembolic disorders, (b) venous cardiovascular thromboembolic disorders, (c) arterial cerebrovascular thromboembolic disorders, or (d) venous cerebrovascular thromboembolic disorders, in a subject in need thereof. Another example of the invention is the use of any of the compounds described herein for use in a method for the treatment and/or prophylaxis of (a) unstable angina, (b) an acute coronary syndrome, (c) atrial fibrillation, (d) first myocardial infarction, (e) recurrent myocardial infarction, (f) ischemic sudden death, (g) transient ischemic attack, (h) stroke, (i) atherosclerosis, (j) peripheral occlusive arterial disease, (k) venous thrombosis, (l) deep vein thrombosis, (m) thrombophlebitis, (n) arterial embolism, (o) coronary arterial thrombosis, (p) cerebral arterial thrombosis, (q) cerebral embolism, (r) kidney embolism, (s) pulmonary embolism, or (t) thrombosis resulting from medical implants, devices, or procedures in which blood is exposed to an artificial surface that promotes thrombosis, in a subject in need thereof. Another example of the invention is the use of any of the compounds described herein for use in a method for the treatment and/or prophylaxis of (a) hereditary angioedema (HAE) or (b) diabetic macular edema (DME), in a subject in need thereof.

In another example, the present invention is directed to a compound as described herein, for use in a method for the treatment and/or prophylaxis of disorders, diseases or conditions as described herein, in a subject in need thereof. In another example, the present invention is directed to a compound as described herein, for use in a method for the treatment and/or prophylaxis of a thromboembolic, inflammatory disorder, or a disease or condition in which plasma kallikrein activity is implicated, as described herein, in a subject in need thereof.

In another example, the present invention is directed to a compound as described herein, for use in methods for the treatment and/or prophylaxis of thromboembolic disorder, such as arterial cardiovascular thromboembolic disorders, venous cardiovascular thromboembolic disorders, arterial cerebrovascular thromboembolic disorders, and venous cerebrovascular thromboembolic disorders, in a subject in need thereof. In another example, the present invention is directed to a compound as described herein, for use in methods for the treatment and/or prophylaxis of unstable angina, an acute coronary syndrome, atrial fibrillation, first myocardial infarction, recurrent myocardial infarction, ischemic sudden death, transient ischemic attack, stroke, atherosclerosis, peripheral occlusive arterial disease, venous thrombosis, deep vein thrombosis, thrombophlebitis, arterial embolism, coronary arterial thrombosis, cerebral arterial thrombosis, cerebral embolism, kidney embolism, pulmonary embolism, and thrombosis resulting from medical implants, devices, or procedures in which blood is exposed to an artificial surface that promotes thrombosis, in a subject in need thereof. In another example, the present invention is directed to a compound as described herein, for use in a method for the treatment and/or prophylaxis of hereditary angioedema (HAE) or diabetic macular edema (DME), in a subject in need thereof.

The present invention is further directed to a compound, composition (e.g. pharmaceutical composition), method of treatment, method of preparation or use, as herein described.

DETAILED DESCRIPTION OF THE INVENTION

1. 1,2,3,8,9,9a-hexahydro-5H-pyrrolo[1,2-a]azepin-5-one Derivatives

Factor XIa is a plasma serine protease involved in the regulation of blood coagulation. While blood coagulation is a necessary and important part of the regulation of an organism's homeostasis, abnormal blood coagulation can also have deleterious effects. For instance, thrombosis is the formation or presence of a blood clot inside a blood vessel or cavity of the heart. Such a blood clot can lodge in a blood vessel blocking circulation and causing a heart attack or stroke. Thromboembolic disorders are the leading cause of mortality and disability in the industrialized world.

Blood clotting is a process of control of the bloodstream essential for the survival of mammals. The process of clotting, and the subsequent dissolution of the clot after wound healing has taken place, commences after vascular injury, and can be divided into four phases. The first phase, vasoconstriction or vasocontraction, can cause a decrease in blood loss in the injured area. In the next phase, platelet activation by thrombin, platelets attach to the site of the vessel wall damage and form a platelet aggregate. In the third phase, formation of clotting complexes leads to massive formation of thrombin, which converts soluble fibrinogen to fibrin by cleavage of two small peptides. In the fourth phase, after wound healing, the thrombus is dissolved by the action of the key enzyme of the endogenous fibrinolysis system, plasmin.

Two alternative pathways can lead to the formation of a fibrin clot, the intrinsic and the extrinsic pathway. These pathways are initiated by different mechanisms, but in the later phase they converge to give a common final path of the clotting cascade. In this final path of clotting, clotting Factor X is activated. The activated Factor X is responsible for the formation of thrombin from the inactive precursor prothrombin circulating in the blood. The formation of a thrombus on the bottom of a vessel wall abnormality without a wound is the result of the intrinsic pathway. Fibrin clot formation as a response to tissue injury or an injury is the result of the extrinsic pathway. Both pathways comprise a relatively large number of proteins, which are known as clotting factors. The intrinsic pathway requires the clotting Factors V, VIII, IX, X, XI and XII and also prekallikrein, high molecular weight kininogen, calcium ions and phospholipids from platelets.

Factor XIa, a plasma serine protease involved in the regulation of blood coagulation, is initiated in vivo by the binding of tissue Factor (TF) to factor VII (FVII) to generate Factor VIIa (FVIIa). The resulting TF:FVIIa complex activates Factor IX (FIX) and Factor X (FX) that leads to the production of Factor Xa (FXa). The generated FXa catalyzes the transformation of prothrombin into small amounts of thrombin before this pathway is shut down by tissue factor pathway inhibitor (TFPI). The process of coagulation is then further propagated via the feedback activation of Factors V, VIII and XI by catalytic amounts of thrombin. (Gailani, D. et al., *Arterioscler. Thromb. Vasc. Biol.*, 27:2507-2513 (2007)). The resulting burst of thrombin converts fibrinogen to fibrin that polymerizes to form the structural framework of a blood clot, and activates platelets, which are a key cellular component of coagulation (Hoffman, M., *Blood Reviews*, 17:S1-S5 (2003)). FactorXIa plays a key role in propagating this amplification loop. Epidemiological studies showed that increased circulating FXI levels in humans have been associated with increased risk for venous and arterial thrombosis, including stroke (se Quan et al. supra). In contrast, patients with congenital FXI deficiency (hemophilia C) are protected from ischemic stroke and venous thromboembolism. Therefore, Factor XIa is an attractive target for antithrombotic therapy.

In addition to stimulation via tissue factor, the coagulation system can be activated particularly on negatively charged surfaces, which include not only surface structures of foreign cells (e.g. bacteria) but also artificial surfaces such as vascular prostheses, stents and extracorporeal circulation. On the surface, initially Factor XII (FXII) is activated to Factor XIIa which subsequently activates Factor XI, attached to cell surfaces, to Factor XIa. This leads to further activation of the coagulation cascade as described above. In addition, Factor XIIa also activates bound plasma prokallikrein to plasma kallikrein (PK) which, in a potentiation loop, leads to further Factor XII activation, overall resulting in amplification of the initiation of the coagulation cascade. In addition, PK is an important bradykinin-releasing protease which leads to increased endothelial permeability. Further substrates that have been described are prorenin and prourokinase, whose activation may influence the regulatory processes of the renin-angiotensin system and fibrinolysis. The activation of PK is therefore an important link between coagulative and inflammatory processes.

Embodiments

The present invention is directed to compounds of formula (I)

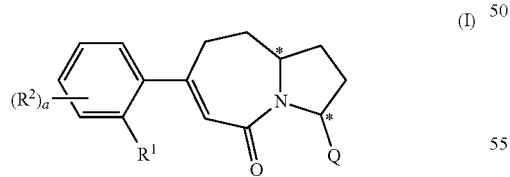

(I)

wherein a, $R^1$, $R^2$, Q, etc. are as described herein; and stereoisomers, isotopologues, and pharmaceutically acceptable salts thereof. The compounds of the present invention are useful for the treatment and/or prophylaxis of thromboembolic disorders, inflammatory disorders and diseases or conditions in which plasma kallikrein activity is implicated.

In some embodiments, the present invention is directed to compounds of formula (I) of the structure (I-A)

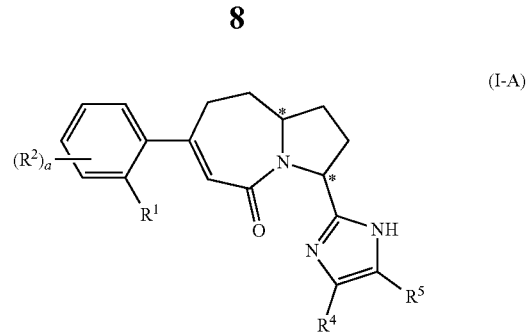

(I-A)

wherein
$R^1$ is selected from the group consisting of halogen, hydroxy, $C_{1-4}$alkyl, fluorinated $C_{1-4}$alkyl, $C_{1-4}$alkoxy, fluorinated $C_{1-4}$alkoxy, cyano, nitro, —$NR^AR^B$, —C(O)—$C_{1-4}$alkyl, $C_{3-6}$cycloalkyl, phenyl and 5 to 6 membered heterocyclyl; wherein the $C_{3-6}$cycloalkyl, phenyl or 5 to 6 membered heterocyclyl is optionally substituted with one or more substituents independently selected from the group consisting of halogen, hydroxy, cyano, $C_{1-4}$alkyl, fluorinated $C_{1-4}$alkyl, $C_{1-4}$alkoxy, fluorinated $C_{1-4}$alkoxy, —C(O)OH, —C(O)O—($C_{1-4}$alkyl), —$NR^AR^B$, —($C_{1-4}$alkylene)-$NR^AR^B$, $C_{3-7}$cycloalkyl and 5 to 6 membered heterocyclyl; and wherein $R^A$ and $R^B$ are each independently selected from the group consisting of hydrogen and $C_{1-4}$alkyl;
a is an integer from 0 to 3;
each $R^2$ is independently selected from the group consisting of chloro, fluoro, methyl and methoxy;
$R^4$ is selected from the group consisting of hydrogen, and halogen;
$R^5$ is selected from the group consisting of phenyl and 5 to 6 membered heteroaryl; wherein the phenyl or 5 to 6 membered heteroaryl is optionally substituted with one to two substituents independently selected from the group consisting of halogen, $C_{1-4}$alkyl, fluorinated $C_{1-2}$alkyl, hydroxy substituted $C_{1-2}$alkyl, —C(O)OH, —C(O)O—($C_{1-4}$alkyl), —$NR^CR^D$, —C(O)—$NR^CR^D$ and —$NR^C$—C(O)—($C_{1-2}$alkyl); and wherein $R^C$ and $R^D$ are each independently selected from the group consisting of hydrogen, $C_{1-2}$alkyl and hydroxy substituted $C_{1-4}$alkyl;
and stereoisomers, isotopologues, and pharmaceutically acceptable salts thereof. In some embodiments, the present invention is directed to compounds of formula (I) of the structure (I-B)

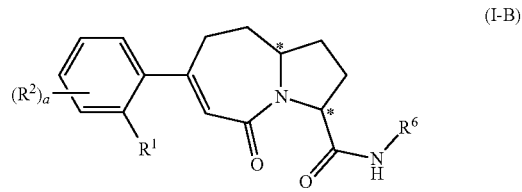

(I-B)

wherein
$R^1$ is selected from the group consisting of halogen, hydroxy, $C_{1-4}$alkyl, fluorinated $C_{1-4}$alkyl, $C_{1-4}$alkoxy, fluorinated $C_{1-4}$alkoxy, cyano, nitro, —$NR^AR^B$, —C(O)—$C_{1-4}$alkyl, $C_{3-6}$cycloalkyl, phenyl and 5 to 6 membered heterocyclyl; wherein the $C_{3-6}$cycloalkyl, phenyl or 5 to 6 membered heterocyclyl is optionally substituted with one or more substituents independently selected from the group consisting of halogen, hydroxy, cyano, $C_{1-4}$alkyl, fluorinated $C_{1-4}$alkyl, $C_{1-4}$alkoxy, fluorinated $C_{1-4}$alkoxy, —C(O)OH, —C(O)O—($C_{1-4}$alkyl), —NR$^A$R$^B$, —($C_{1-4}$alkylene)-NR$^A$R$^B$, $C_{3-7}$cycloalkyl and 5 to 6 membered heterocyclyl; and wherein R$^A$ and R$^B$ are each independently selected from the group consisting of hydrogen and $C_{1-4}$alkyl;

a is an integer from 0 to 3;

each R$^2$ is independently selected from the group consisting of chloro, fluoro, methyl and methoxy;

R$^6$ is selected from the group consisting of phenyl and 9 to 10 membered heteroaryl; wherein the phenyl or 9 to 10 membered heteroaryl is optionally substituted with one to two substituents independently selected from the group consisting of halogen, $C_{1-4}$alkyl, fluorinated $C_{1-2}$alkyl, hydroxy substituted $C_{1-2}$alkyl, —C(O)OH, —C(O)O—($C_{1-4}$alkyl), —NR$^C$R$^D$, —C(O)—NR$^E$R$^F$, and —NR$^C$—C(O)—($C_{1-2}$alkyl); wherein R$^E$ and R$^F$ are each independently selected from the group consisting of hydrogen and $C_{1-4}$alkyl;

and stereoisomers, isotopologues, and pharmaceutically acceptable salts thereof.

In some embodiments, the present invention is directed to compounds of formula (I) wherein R$^1$ is selected from the group consisting of halogen, hydroxy, $C_{1-4}$alkyl, fluorinated $C_{1-2}$alkyl, $C_{1-4}$alkoxy, fluorinated $C_{1-2}$alkoxy, $C_{3-6}$cycloalkyl, phenyl and 5 to 6 membered heterocyclyl; wherein the $C_{3-6}$cycloalkyl, phenyl or 5 to 6 membered heterocyclyl is optionally substituted with one to two substituents independently selected from the group consisting of halogen, hydroxy, $C_{1-4}$alkyl, fluorinated $C_{1-2}$alkyl, $C_{1-4}$alkoxy, fluorinated $C_{1-2}$alkoxy, —C(O)OH, and —C(O)O—($C_{1-4}$alkyl);

a is an integer from 0 to 2;

each R$^2$ is independently selected from the group consisting of chloro, fluoro, methyl and methoxy;

Q is selected from the group consisting of

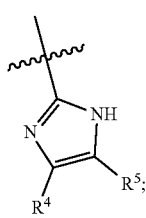

(a)

wherein R$^4$ is selected from the group consisting of hydrogen, and halogen;

wherein R$^5$ is selected from the group consisting of phenyl and 5 to 6 membered heteroaryl; wherein the phenyl or 5 to 6 membered heteroaryl is optionally substituted with one to two substituents independently selected from the group consisting of halogen, $C_{1-4}$alkyl, fluorinated $C_{1-2}$alkyl, hydroxy substituted $C_{1-2}$alkyl, —C(O)OH, —C(O)O—($C_{1-4}$alkyl), —NR$^C$R$^D$, —C(O)—NR$^C$R$^D$ and —NR$^C$—C(O)—($C_{1-2}$alkyl); and wherein R$^C$ and R$^D$ are each independently selected from the group consisting of hydrogen, $C_{1-2}$alkyl and hydroxy substituted $C_{1-4}$alkyl;

and

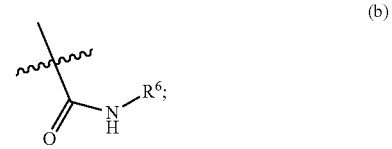

(b)

wherein R$^6$ is selected from the group consisting of phenyl and 9 to 10 membered heteroaryl; wherein the phenyl or 9 to 10 membered heteroaryl is optionally substituted with one to two substituents independently selected from the group consisting of halogen, $C_{1-4}$alkyl, fluorinated $C_{1-2}$alkyl, hydroxy substituted $C_{1-2}$alkyl, —C(O)OH, —C(O)O—($C_{1-4}$alkyl), and —C(O)—NR$^E$R$^F$; wherein R$^E$ and R$^F$ are each independently selected from the group consisting of hydrogen and $C_{1-2}$alkyl;

and stereoisomers, isotopologues, and pharmaceutically acceptable salts thereof.

In some embodiments, the present invention is directed to compounds of formula (I) wherein R$^1$ is selected from the group consisting of fluorinated $C_{1-2}$alkoxy, and 5 to 6 membered heterocyclyl; wherein the 5 to 6 membered heterocyclyl is optionally substituted with fluorinated $C_{1-2}$alkyl;

a is an integer from 1 to 2;

each R$^2$ is independently selected from the group consisting of chloro, and fluoro;

Q is selected from the group consisting of (a)

wherein R$^4$ is selected from the group consisting of hydrogen and fluoro;

wherein R$^5$ is selected from the group consisting of phenyl and 6 membered heteroaryl; wherein the phenyl or 6 membered heteroaryl is optionally substituted with one to two substituents independently selected from the group consisting of halogen, hydroxy substituted $C_{1-2}$alkyl, —C(O)OH, —NR$^C$R$^D$, —C(O)—NR$^C$R$^D$ and —NR$^C$—C(O)—($C_{1-2}$alkyl); wherein R$^C$ and R$^D$ are each independently selected from the group consisting of hydrogen, $C_{1-2}$alkyl and hydroxy substituted $C_{1-4}$alkyl;

and

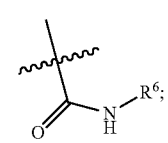

(b)

wherein R$^6$ is selected from the group consisting of phenyl and 9 to 10 membered heteroaryl; wherein the phenyl or 9 to 10 membered heteroaryl is optionally substituted with one to two substituents independently selected from the group consisting of halogen, fluorinated $C_{1-2}$alkyl, —C(O)OH) and —C(O)—NR$^E$R$^F$; wherein R$^E$ and R$^F$ are each independently selected from the group consisting of hydrogen and $C_{1-2}$alkyl;

and stereoisomers, isotopologues, and pharmaceutically acceptable salts thereof.

In some embodiments, the present invention is directed to compounds of formula (I) wherein R$^1$ is selected from the group consisting of difluoromethoxy, 4-(trifluoromethyl)-1,2,3-triazol-1-yl, and 1,2,3,4-tetrazol-1-yl;

a is an integer from 1 to 2;

each R$^2$ is independently selected from the group consisting of 2-fluoro and 3-chloro;

Q is selected from the group consisting of

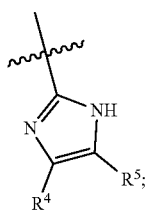

(a)

wherein R$^4$ is selected from the group consisting of hydrogen and fluoro;

wherein R$^5$ is selected from the group consisting of 2-fluoro-4-(amino-carbonyl)-phenyl, 2-fluoro-6-amino-pyridin-3-yl, 2-((2-hydroxy,2-methyl-n-propyl)-amino)-3-fluoro-pyridin-3-yl, 2-carboxy-3-fluoro-pyridin-4-yl, 2-(hydroxy-methyl)-3-fluoro-pyridin-4-yl, 2-amino-3-fluoro-pyridin-4-yl, 2-(ethyl-amino)-3-fluoro-pyridin-4-yl, and 2-(methyl-carbonyl-amino)-3-fluoro-pyridin-4-yl;

and

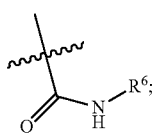

(b)

wherein R$^6$ is selected from the group consisting of 4-carboxy-phenyl, 3-fluoro-4-(amino-carbonyl)-phenyl, 2-(difluoro-methyl)-indazol-5-yl, and quinoxalin-6-yl;

and stereoisomers, isotopologues, and pharmaceutically acceptable salts thereof.

In some embodiments, the present invention is directed to compounds of formula (I) wherein R$^1$ is selected from the group consisting of 4-(trifluoromethyl)-1,2,3-triazol-1-yl, and 1,2,3,4-tetrazol-1-yl;

a is an integer from 1 to 2;

each R$^2$ is independently selected from the group consisting of 2-fluoro and 3-chloro;

Q is

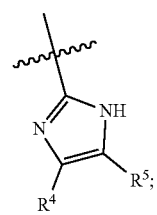

(a)

wherein R$^4$ is selected from the group consisting of hydrogen and fluoro;

wherein R$^5$ is selected from the group consisting of 2-fluoro-4-(amino-carbonyl)-phenyl, 2-fluoro-6-amino-pyridin-3-yl, 2-((2-hydroxy,2-methyl-n-propyl)-amino)-3-fluoro-pyridin-3-yl, 2-carboxy-3-fluoro-pyridin-4-yl, 2-(hydroxy-methyl)-3-fluoro-pyridin-4-yl, 2-amino-3-fluoro-pyridin-4-yl, 2-(ethyl-amino)-3-fluoro-pyridin-4-yl, and 2-(methyl-carbonyl-amino)-3-fluoro-pyridin-4-yl; and stereoisomers, isotopologues, and pharmaceutically acceptable salts thereof.

In some embodiments, the present invention is directed to compounds of formula (I) wherein R$^1$ is selected from the group consisting of difluoromethoxy, and 1,2,3,4-tetrazol-1-yl;

a is 2; the two R$^2$ are 2-fluoro and 3-chloro;

Q is

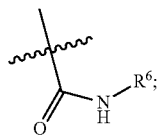

(b)

wherein R$^6$ is selected from the group consisting of 4-carboxy-phenyl, 3-fluoro-4-(amino-carbonyl)-phenyl, 2-(difluoro-methyl)-indazol-5-yl, and quinoxalin-6-yl;

and stereoisomers, isotopologues, and pharmaceutically acceptable salts thereof.

In some embodiments, the present invention is directed to compounds of formula (I) wherein R$^1$ is selected from the group consisting of difluoromethoxy, 4-(trifluoromethyl)-1,2,3-triazol-1-yl and 1,2,3,4-tetrazol-1-yl;

a is an integer from 1 to 2;

each R$^2$ is independently selected from the group consisting of 2-fluoro and 3-chloro;

Q is selected from the group consisting of

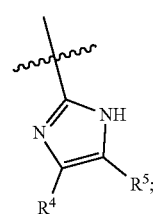

(a)

wherein R$^4$ is selected from the group consisting of hydrogen and fluoro;

wherein R⁵ is selected from the group consisting of 2-fluoro-4-(amino-carbonyl)-phenyl, 2-fluoro-6-amino-pyridin-3-yl, 2-((2-hydroxy,2-methyl-n-propyl)-amino)-3-fluoro-pyridin-3-yl, 2-carboxy-3-fluoro-pyridin-4-yl, 2-amino-3-fluoro-pyridin-4-yl, and 2-(ethyl-amino)-3-fluoro-pyridin-4-yl;
and

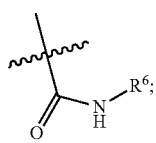

(b)

wherein R⁶ is selected from the group consisting of 3-fluoro-4-(amino-carbonyl)-phenyl, 2-(difluoromethyl)-indazol-5-yl, and quinoxalin-6-yl;
and stereoisomers, isotopologues, and pharmaceutically acceptable salts thereof.

In some embodiments, the present invention is directed to compounds of formula (I) wherein R¹ is selected from the group consisting of halogen, hydroxy, $C_{1-4}$alkyl, fluorinated $C_{1-2}$alkyl, $C_{1-4}$alkoxy, fluorinated $C_{1-2}$alkoxy, $C_{3-6}$cycloalkyl, phenyl and 5 to 6 membered heterocyclyl; wherein the $C_{3-6}$cycloalkyl, phenyl or 5 to 6 membered heterocyclyl is optionally substituted with one to two substituents independently selected from the group consisting of halogen, hydroxy, $C_{1-4}$alkyl, fluorinated $C_{1-2}$alkyl, $C_{1-4}$alkoxy, fluorinated $C_{1-2}$alkoxy, —C(O)OH, and —C(O)O—($C_{1-4}$alkyl).

In some embodiments, the present invention is directed to compounds of formula (I) wherein R¹ is selected from the group consisting of fluorinated $C_{1-2}$alkoxy, and 5 to 6 membered heterocyclyl; wherein the 5 to 6 membered heterocyclyl is optionally substituted with fluorinated $C_{1-2}$alkyl.

In some embodiments, the present invention is directed to compounds of formula (I) wherein R¹ is selected from the group consisting of difluoromethoxy, 4-(trifluoromethyl)-1,2,3-triazol-1-yl, and 1,2,3,4-tetrazol-1-yl. In some embodiments, the present invention is directed to compounds of formula (I) wherein R¹ is selected from the group consisting of difluoromethoxy, and 1,2,3,4-tetrazol-1-yl. In some embodiments, the present invention is directed to compounds of formula (I) wherein R¹ is selected from the group consisting of 4-(trifluoromethyl)-1,2,3-triazol-1-yl, and 1,2,3,4-tetrazol-1-yl.

In some embodiments, the present invention is directed to compounds of formula (I) wherein a is an integer from 0 to 2. In some embodiments, the present invention is directed to compounds of formula (I) wherein a is an integer from 1 to 3. In some embodiments, the present invention is directed to compounds of formula (I) wherein a is an integer from 1 to 2. In some embodiments, the present invention is directed to compounds of formula (I) wherein a is 0. In some embodiments, the present invention is directed to compounds of formula (I) wherein a is 1. In some embodiments, the present invention is directed to compounds of formula (I) wherein a is 2. In some embodiments, the present invention is directed to compounds of formula (I) wherein a is 3.

In some embodiments, the present invention is directed to compounds of formula (I) wherein each R² is independently selected from the group consisting of chloro, fluoro, methyl and methoxy. In some embodiments, the present invention is directed to compounds of formula (I) wherein each R² is independently selected from the group consisting of chloro, and fluoro. In some embodiments, the present invention is directed to compounds of formula (I) wherein each R² is independently selected from the group consisting of 2-fluoro and 3-chloro. In some embodiments, the present invention is directed to compounds of formula (I) wherein two R² groups are present and are 2-fluoro and 3-chloro.

In some embodiments, the present invention is directed to compounds of formula (I) wherein Q is selected from the group consisting of

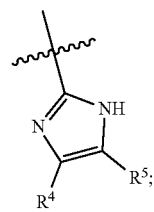

(a)

wherein R⁴ is selected from the group consisting of hydrogen, and halogen; wherein R⁵ is selected from the group consisting of phenyl and 5 to 6 membered heteroaryl; wherein the phenyl or 5 to 6 membered heteroaryl is optionally substituted with one to two substituents independently selected from the group consisting of halogen, $C_{1-4}$alkyl, fluorinated $C_{1-2}$alkyl, hydroxy substituted $C_{1-2}$alkyl, —C(O)OH, —C(O)O—($C_{1-4}$alkyl), —NR$^C$R$^D$, —C(O)—NR$^C$R$^D$ and —NR$^C$—C(O)—($C_{1-2}$alkyl); and wherein R$^C$ and R$^D$ are each independently selected from the group consisting of hydrogen, $C_{1-2}$alkyl and hydroxy substituted $C_{1-4}$alkyl; and

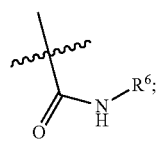

(b)

wherein R⁶ is selected from the group consisting of phenyl and 9 to 10 membered heteroaryl; wherein the phenyl or 9 to 10 membered heteroaryl is optionally substituted with one to two substituents independently selected from the group consisting of halogen, $C_{1-4}$alkyl, fluorinated $C_{1-2}$alkyl, hydroxy substituted $C_{1-2}$alkyl, —C(O)OH, —C(O)O—($C_{1-4}$alkyl), and —C(O)—NR$^E$R$^F$; wherein R$^E$ and R$^F$ are each independently selected from the group consisting of hydrogen and $C_{1-2}$alkyl.

In some embodiments, the present invention is directed to compounds of formula (I) wherein Q is selected from the group consisting of

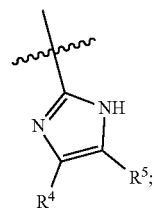

(a)

wherein R⁴ is selected from the group consisting of hydrogen and fluoro; wherein R⁵ is selected from the group consisting of phenyl and 6 membered heteroaryl; wherein the phenyl or 6 membered heteroaryl is optionally substituted with one to two substituents independently selected from the group consisting of halogen, hydroxy substituted C₁₋₂alkyl, —C(O)OH, —NR^C R^D, —C(O)—NR^C R^D and —NR^C—C(O)—(C₁₋₂alkyl); wherein R^C and R^D are each independently selected from the group consisting of hydrogen, C₁₋₂alkyl and hydroxy substituted C₁₋₄alkyl; and

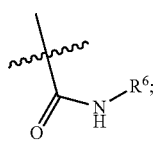
(b)

wherein R⁶ is selected from the group consisting of phenyl and 9 to 10 membered heteroaryl; wherein the phenyl or 9 to 10 membered heteroaryl is optionally substituted with one to two substituents independently selected from the group consisting of halogen, fluorinated C₁₋₂alkyl, —C(O)OH and —C(O)—NR^E R^F; wherein R^E and R^F are each independently selected from the group consisting of hydrogen and C₁₋₂alkyl.

In some embodiments, the present invention is directed to compounds of formula (I) wherein Q is selected from the group consisting of (a)

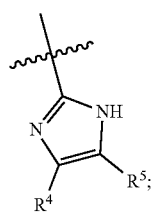
(a)

wherein R⁴ is selected from the group consisting of hydrogen and fluoro; wherein R⁵ is selected from the group consisting of 2-fluoro-4-(amino-carbonyl)-phenyl, 2-fluoro-6-amino-pyridin-3-yl, 2-((2-hydroxy,2-methyl-n-propyl)-amino)-3-fluoro-pyridin-3-yl, 2-carboxy-3-fluoro-pyridin-4-yl, 2-(hydroxy-methyl)-3-fluoro-pyridin-4-yl, 2-amino-3-fluoro-pyridin-4-yl, 2-(ethyl-amino)-3-fluoro-pyridin-4-yl, and 2-(methyl-carbonyl-amino)-3-fluoro-pyridin-4-yl; and

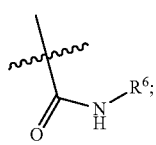
(b)

wherein R⁶ is selected from the group consisting of 4-carboxy-phenyl, 3-fluoro-4-(amino-carbonyl)-phenyl, 2-(difluoro-methyl)-indazol-5-yl, and quinoxalin-6-yl.

In some embodiments, the present invention is directed to compounds of formula (I) wherein Q is selected from the group consisting of

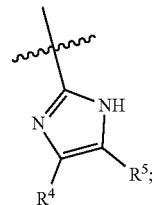
(a)

wherein R⁴ is selected from the group consisting of hydrogen and fluoro; wherein R⁵ is selected from the group consisting of 2-fluoro-4-(amino-carbonyl)-phenyl, 2-fluoro-6-amino-pyridin-3-yl, 2-((2-hydroxy,2-methyl-n-propyl)-amino)-3-fluoro-pyridin-3-yl, 2-carboxy-3-fluoro-pyridin-4-yl, 2-amino-3-fluoro-pyridin-4-yl, and 2-(ethyl-amino)-3-fluoro-pyridin-4-yl; and

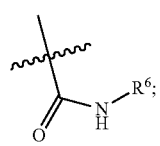
(b)

wherein R⁶ is selected from the group consisting of 3-fluoro-4-(amino-carbonyl)-phenyl, 2-(difluoro-methyl)-indazol-5-yl, and quinoxalin-6-yl.

In some embodiments, the present invention is directed to compounds of formula (I) wherein Q is

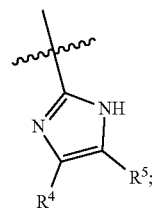
(a)

wherein R⁴ is selected from the group consisting of hydrogen and fluoro; wherein R⁵ is selected from the group consisting of 2-fluoro-4-(amino-carbonyl)-phenyl, 2-fluoro-6-amino-pyridin-3-yl, 2-((2-hydroxy,2-methyl-n-propyl)-amino)-3-fluoro-pyridin-3-yl, 2-carboxy-3-fluoro-pyridin-4-yl, 2-(hydroxy-methyl)-3-fluoro-pyridin-4-yl, 2-amino-3-fluoro-pyridin-4-yl, 2-(ethyl-amino)-3-fluoro-pyridin-4-yl, and 2-(methyl-carbonyl-amino)-3-fluoro-pyridin-4-yl.

In some embodiments, the present invention is directed to compounds of formula (I) wherein Q is

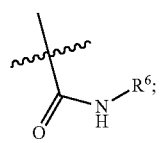
(b)

wherein R⁶ is selected from the group consisting of 4-carboxy-phenyl, 3-fluoro-4-(amino-carbonyl)-phenyl, 2-(difluoro-methyl)-indazol-5-yl, and quinoxalin-6-yl.

In some embodiments, the present invention is directed to compounds of formula (I) wherein $R^4$ is selected from the group consisting of hydrogen, and halogen. In some embodiments, the present invention is directed to compounds of formula (I) wherein $R^4$ is selected from the group consisting of hydrogen and fluoro. In some embodiments, the present invention is directed to compounds of formula (I) wherein $R^4$ is hydrogen. In some embodiments, the present invention is directed to compounds of formula (I) wherein $R^4$ is fluoro.

In some embodiments, the present invention is directed to compounds of formula (I) wherein $R^5$ is selected from the group consisting of phenyl and 5 to 6 membered heteroaryl; wherein the phenyl or 5 to 6 membered heteroaryl is optionally substituted with one to two substituents independently selected from the group consisting of halogen, $C_{1-4}$alkyl, fluorinated $C_{1-2}$alkyl, hydroxy substituted $C_{1-2}$alkyl, —C(O)OH, —C(O)O—($C_{1-4}$alkyl), —NR$^C$R$^D$, —C(O)—NR$^C$R$^D$ and —NR$^C$—C(O)—($C_{1-2}$alkyl); and wherein R$^C$ and R$^D$ are each independently selected from the group consisting of hydrogen, $C_{1-2}$alkyl and hydroxy substituted $C_{1-4}$alkyl. In some embodiments, the present invention is directed to compounds of formula (I) wherein $R^5$ is selected from the group consisting of phenyl and 6 membered heteroaryl; wherein the phenyl or 6 membered heteroaryl is optionally substituted with one to two substituents independently selected from the group consisting of halogen, hydroxy substituted $C_{1-2}$alkyl, —C(O)OH, —NR$^C$R$^D$, —C(O)—NR$^C$R$^D$ and —NR$^C$—C(O)—($C_{1-2}$alkyl); wherein R$^C$ and R$^D$ are each independently selected from the group consisting of hydrogen, $C_{1-2}$alkyl and hydroxy substituted $C_{1-4}$alkyl.

In some embodiments, the present invention is directed to compounds of formula (I) wherein $R^5$ is selected from the group consisting of 2-fluoro-4-(amino-carbonyl)-phenyl, 2-fluoro-6-amino-pyridin-3-yl, 2-((2-hydroxy,2-methyl-n-propyl)-amino)-3-fluoro-pyridin-3-yl, 2-carboxy-3-fluoro-pyridin-4-yl, 2-(hydroxy-methyl)-3-fluoro-pyridin-4-yl, 2-amino-3-fluoro-pyridin-4-yl, 2-(ethyl-amino)-3-fluoro-pyridin-4-yl, and 2-(methyl-carbonyl-amino)-3-fluoro-pyridin-4-yl. In some embodiments, the present invention is directed to compounds of formula (I) wherein $R^5$ is selected from the group consisting of 2-fluoro-4-(amino-carbonyl)-phenyl, 2-fluoro-6-amino-pyridin-3-yl, 2-((2-hydroxy,2-methyl-n-propyl)-amino)-3-fluoro-pyridin-3-yl, 2-carboxy-3-fluoro-pyridin-4-yl, 2-amino-3-fluoro-pyridin-4-yl, and 2-(ethyl-amino)-3-fluoro-pyridin-4-yl.

In some embodiments, the present invention is directed to compounds of formula (I) wherein $R^6$ is selected from the group consisting of phenyl and 9 to 10 membered heteroaryl; wherein the phenyl or 9 to 10 membered heteroaryl is optionally substituted with one to two substituents independently selected from the group consisting of halogen, $C_{1-4}$alkyl, fluorinated $C_{1-2}$alkyl, hydroxy substituted $C_{1-2}$alkyl, —C(O)OH, —C(O)O—($C_{1-4}$alkyl), and —C(O)—NR$^E$R$^F$; wherein R$^E$ and R$^F$ are each independently selected from the group consisting of hydrogen and $C_{1-2}$alkyl. In some embodiments, the present invention is directed to compounds of formula (I) wherein $R^6$ is selected from the group consisting of phenyl and 9 to 10 membered heteroaryl; wherein the phenyl or 9 to 10 membered heteroaryl is optionally substituted with one to two substituents independently selected from the group consisting of halogen, fluorinated $C_{1-2}$alkyl, —C(O)OH) and —C(O)—NR$^E$R$^F$; wherein R$^E$ and R$^F$ are each independently selected from the group consisting of hydrogen and $C_{1-2}$alkyl.

In some embodiments, the present invention is directed to compounds of formula (I) wherein $R^6$ is selected from the group consisting of 4-carboxy-phenyl, 3-fluoro-4-(amino-carbonyl)-phenyl, 2-(difluoro-methyl)-indazol-5-yl, and quinoxalin-6-yl. In some embodiments, the present invention is directed to compounds of formula (I) wherein $R^6$ is selected from the group consisting of 3-fluoro-4-(amino-carbonyl)-phenyl, 2-(difluoro-methyl)-indazol-5-yl, and quinoxalin-6-yl.

In some embodiments, the present invention is directed to one or more compounds of formula (I) independently selected from the group consisting of
4-(2-((3S,9aS)-7-(3-chloro-2-fluoro-6-(1H-tetrazol-1-yl) phenyl)-5-oxo-2,3,5,8,9,9a-hexahydro-1H-pyrrolo[1,2-a] azepin-3-yl)-1H-imidazol-5-yl)-3-fluorobenzamide;
(3S,9aS)-7-(3-chloro-2-fluoro-6-(1H-tetrazol-1-yl)phenyl)-N-(2-(difluoromethyl)-2H-indazol-5-yl)-5-oxo-2,3,5,8,9,9a-hexahydro-1H-pyrrolo[1,2-a]azepine-3-carboxamide;
3S,9aS)-7-(3-chloro-2-fluoro-6-(1H-tetrazol-1-yl)phenyl)-5-oxo-N-(quinoxalin-6-yl)-2,3,5,8,9,9a-hexahydro-1H-pyrrolo[1,2-a]azepine-3-carboxamide;
and isotopologues and pharmaceutically acceptable salts thereof.

One skilled in the art will recognize that, depending on substituent groups, the compounds of the present invention may contain one or more stereo-centers, including, for example, the two stereo-centers denoted by the star ("*") symbols in the structure of the compounds of formula (I) shown below

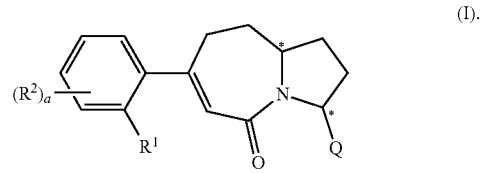

(I).

Unless otherwise noted, the starred ("*") stereo-center at the bridge carbon atom of the 1,2,3,8,9,9a-hexahydro-5H-pyrrolo[1,2-a]azepin-5-one structure shall be referred to as the "Ring" stereo-center. Similarly, the starred ("*") stereo-center at the carbon atom of the 1,2,3,8,9,9a-hexahydro-5H-pyrrolo[1,2-a]azepin-5-one structure bound to the Q substituent group shall be referred to as the "Q" stereo-center.

In some embodiments, the present invention is directed to compounds of formula (I) wherein the Ring stereo-center is present as a racemic mixture. In some embodiments, the present invention is directed to compounds of formula (I) wherein the Ring stereo-center is present in an enantiomeric excess of the corresponding R-enantiomer. In some embodiments, the present invention is directed to compounds of formula (I) wherein the Ring stereocenter is present in an enantiomeric excess of the corresponding S-enantiomer.

In some embodiments, the present invention is directed to compounds of formula (I) wherein the Ring stereo-center is present in an stereo-isomeric excess of either the R- or S-enantiomer of about 55%, about 60%, about 65%, about 70%, about 75%, about 80%, about 85%, about 90%, about 91%, about 92%, about 93%, about 94%, about 95%, about 96%, about 97%, about 98% or about 99%. Preferably, the compound of formula (I) is present in a stereo-isomeric excess at the Ring stereo-center of greater than or equal to about 80%, preferably greater than or equal to about 90%, more preferably greater than or equal to about 93%, more preferably greater than or equal to about 95%, more preferably greater than or equal to about 97%, more preferably greater than or equal to about 98%, more preferably greater than or equal to about 99%.

In some embodiments, the present invention is directed to compounds of formula (I) wherein the Q stereo-center is present as a racemic mixture. In some embodiments, the present invention is directed to compounds of formula (I) wherein the Q stereo-center is present in an enantiomeric excess of the corresponding R-enantiomer. In some embodiments, the present invention is directed to compounds of formula (I) wherein the Q stereocenter is present in an enantiomeric excess of the corresponding S-enantiomer.

In some embodiments, the present invention is directed to compounds of formula (I) wherein the Q stereo-center is present in an stereo-isomeric excess of either the R- or S-enantiomer of about 55%, about 60%, about 65%, about 70%, about 75%, about 80%, about 85%, about 90%, about 91%, about 92%, about 93%, about 94%, about 95%, about 96%, about 97%, about 98% or about 99%. Preferably, the compound of formula (I) is present in a stereo-isomeric excess at the Ring stereo-center of greater than or equal to about 80%, preferably greater than or equal to about 90%, more preferably greater than or equal to about 93%, more preferably greater than or equal to about 95%, more preferably greater than or equal to about 97%, more preferably greater than or equal to about 98%, more preferably greater than or equal to about 99%.

Additional embodiments of the present invention include those wherein the substituents selected for one or more of the variables defined herein (i.e. a, $R^1$, $R^2$, Q, etc.) are independently selected to be any individual substituent or any subset of substituents selected from the complete list as defined herein.

Additional embodiments of the present invention include those wherein the substituents selected for one or more of the variables defined herein (a, $R^1$, $R^2$, Q, etc.) are independently selected to correspond to any of the embodiments as defined herein.

In additional embodiments, the present invention is directed to any single compound or subset of compounds independently selected from the list of representative compounds in Tables 1 and 2, below.

Representative compounds of the present invention are as listed in Tables 1 and 2, below. Unless otherwise noted, the position of $R^2$ group(s) as listed in the Tables below using the following numbering scheme:

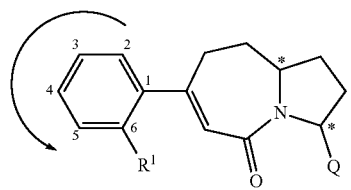

such that the $R^1$ substituent is bound at the 6-position and the $R^2$ substituents are bound at the 2-, 3-, 4- and/or 5-positions of the phenyl group.

In Tables 1 and 2 below, the column headed "Ring Stereo" lists the stereo-orientation at the Ring stereo-center; whereas the column headed "Q Stereo" lists the stereo-orientation at the Q stereo-center. Compounds prepared as racemic mixtures of the designated stereocenters are denoted as "RAC". The S* and R* designations indicate that although the compound was prepared in an excess of one of the corresponding stereoisomers, the exact stereo-configuration was not determined. The S and R designations indicate that the compound was prepared in an excess of the corresponding S or R stereoisomer, with the exact stereo-configuration as noted.

TABLE 1

Representative Compounds of Formula (I)

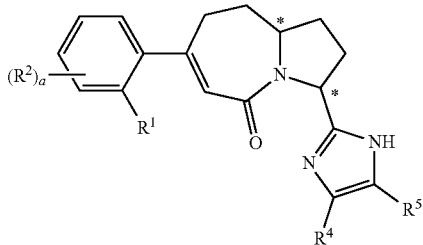

| ID No. | $R^1$ | $(R^2)_a$ | Bridge Stereo | Stereo | $R^4$ | $R^5$ |
|---|---|---|---|---|---|---|
| 1 | 1,2,3,4-tetrazol-1-yl | 2-fluoro, 3-chloro | R | S | H | 2-fluoro-4-(aminocarbonyl)-phenyl |
| 2 | 1,2,3,4-tetrazol-1-yl | 2-fluoro, 3-chloro | S | S | H | 2-fluoro-4-(aminocarbonyl)-phenyl |
| 4 | 1,2,3,4-tetrazol-1-yl | 3-chloro | RAC | S | fluoro | 2-amino-3-fluoro-pyridin-4-yl |
| 5 | 1,2,3,4-tetrazol-1-yl | 3-chloro | RAC | S | fluoro | 2-(methyl-carbonyl-amino)-3-fluoro-pyridin-4-yl |
| 6 | 4-(trifluoro-methyl)-1,2,3-triazol-1-yl | 2-fluoro, 3-chloro | S | S | H | 2-carboxy-3-fluoro-pyridin-4-yl |
| 7 | 4-(trifluoro-methyl)-1,2,3-triazol-1-yl | 3-chloro | S | S | H | 2-carboxy-3-fluoro-pyridin-4-yl |
| 8 | 1,2,3,4-tetrazol-1-yl | 3-chloro | S | S | H | 2-(ethyl-amino)-3-fluoro-pyridin-4-yl |
| 9 | 1,2,3,4-tetrazol-1-yl | 3-chloro | S | S | H | 2-amino-3-fluoro-pyridin-4-yl |
| 12 | 1,2,3,4-tetrazol-1-yl | 3-chloro | S | S | H | 2-((2-hydroxy,2-methyl-n-propyl)-amino)-3-fluoro-pyridin-3-yl |
| 13 | 1,2,3,4-tetrazol-1-yl | 3-chloro | R | S | H | 2-((2-hydroxy,2-methyl-n-propyl)-amino)-3-fluoro-pyridin-3-yl |
| 14 | 1,2,3,4-tetrazol-1-yl | 2-fluoro, 3-chloro | R* | S | H | 2-fluoro-6-amino-pyridin-3-yl |
| 15 | 1,2,3,4-tetrazol-1-yl | 2-fluoro, 3-chloro | S* | S | H | 2-fluoro-6-amino-pyridin-3-yl |
| 16 | 1,2,3,4-tetrazol-1-yl | 2-fluoro, 3-chloro | S | S | H | 2-amino-3-fluoro-pyridin-4-yl |
| 17 | 1,2,3,4-tetrazol-1-yl | 2-fluoro, 3-chloro | S | S | H | 2-(hydroxy-methyl)-3-fluoro-pyridin-4-yl |
| 22 | 1,2,3,4-tetrazol-1-yl | 3-chloro | S | R* | H | 2-fluoro-6-amino-pyridin-3-yl |
| 23 | 1,2,3,4-tetrazol-1-yl | 3-chloro | S | S* | H | 2-fluoro-6-amino-pyridin-3-yl |

TABLE 2

Representative Compounds of Formula (I)

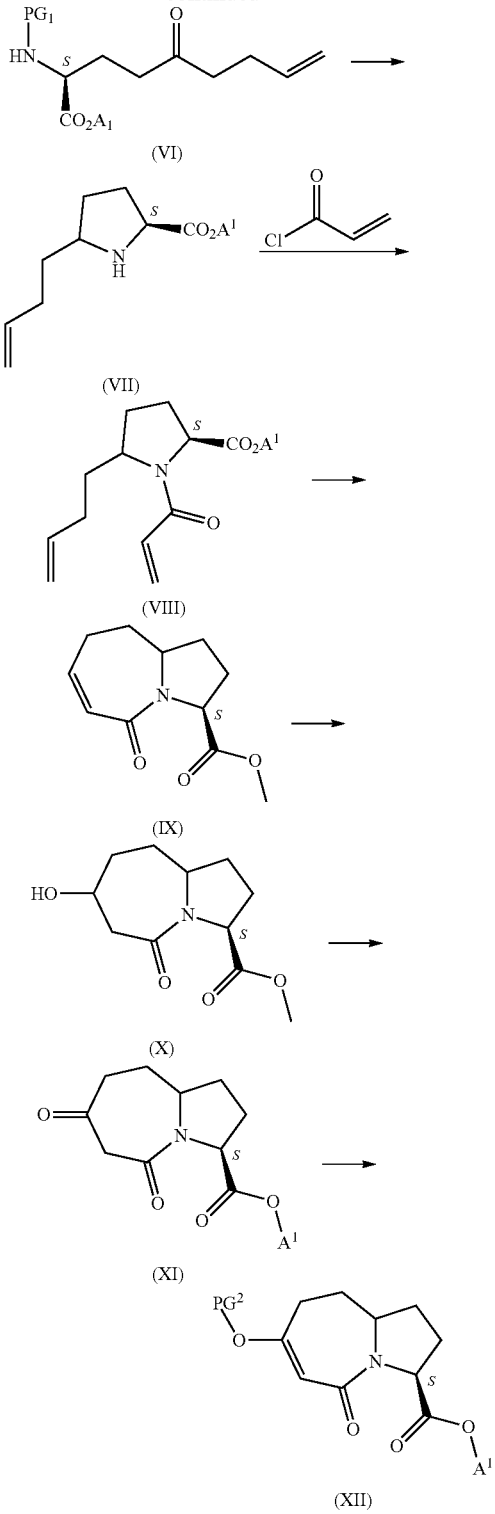

| ID No. | R¹ | (R²)ₐ | Bridge Stereo | Stereo | R⁶ |
|---|---|---|---|---|---|
| 3 | difluoro-methoxy | 2-fluoro, 3-chloro | S* | S* | 4-carboxy-phenyl |
| 10 | 1,2,3,4-tetrazol-1-yl | 2-fluoro, 3-chloro | R | S | 2-(difluoro-methyl)-indazol-5-yl |
| 11 | 1,2,3,4-tetrazol-1-yl | 2-fluoro, 3-chloro | S | S | 2-(difluoro-methyl)-indazol-5-yl |
| 18 | 1,2,3,4-tetrazol-1-yl | 2-fluoro, 3-chloro | R | S | quinoxalin-6-yl |
| 19 | 1,2,3,4-tetrazol-1-yl | 2-fluoro, 3-chloro | S | S | quinoxalin-6-yl |
| 20 | 1,2,3,4-tetrazol-1-yl | 2-fluoro, 3-chloro | R | S | 3-fluoro-4-(amino-carbonyl)-phenyl |
| 21 | 1,2,3,4-tetrazol-1-yl | 2-fluoro, 3-chloro | S | S | 3-fluoro-4-(amino-carbonyl)-phenyl |

2. General Synthesis Schemes

Compounds of formula (I) of the present invention may be prepared as described in the general synthesis schemes and Examples which follow hereinafter, selecting and substituting suitable reagents and conditions, as would be well within the skill of persons versed in the art. Additionally, the preparation of any starting materials used in the schemes and synthesis examples which follow hereinafter is well within the skill of persons versed in the art.

Compounds of formula (I) may be prepared from the intermediate compound of formula (XII)

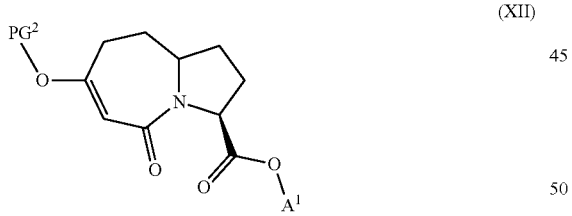

(XII)

wherein A¹ is $C_{1-4}$alkyl, preferably methyl or ethyl; and wherein PG² is a suitably selected oxygen protecting group such as Tf, and the like. Compounds of formula (XII) may be prepared as described in Scheme 1, below.

Scheme 1

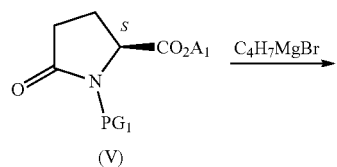

(V)

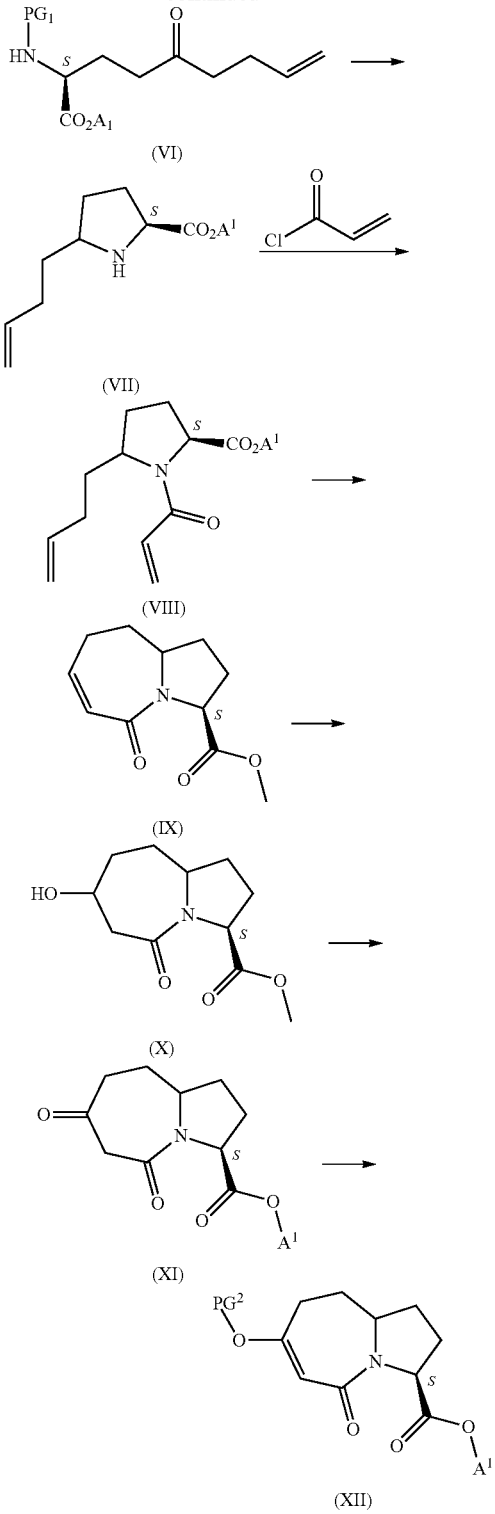

Accordingly, a suitably substituted compound of formula (V), wherein A¹ is a suitably selected $C_{1-4}$alkyl such as methyl, ethyl, and the like, and wherein PG¹ is a suitably selected nitrogen protecting group such as Boc, and the like, a known compound or compound prepared by known methods is reacted with butenyl magnesium bromide, a known compound; in a suitably selected solvent such as THF, 2-Me-THF, and the like; at a reduced temperature, such as about −78° C.; to yield the corresponding compound of formula (VI).

The compound of formula (VI) is reacted with a suitably selected reducing agent such as a mixture of BF$_3$·Et$_2$O and triphenyl silane, triethylsilane, and the like; in a suitably selected solvent such as DCM, chloroform, and the like; at a reduced temperature for example at about −78° C., with warming to about room temperature; to yield the corresponding compound of formula (VII).

The compound of formula (VII) is reacted with acryloyl chloride, a known compound; in the presence of a suitably selected organic amine base such as TEA, DIPEA, pyridine, and the like; in a suitably selected solvent such as THF, DMF, and the like; at a reduced temperature for example at about −78° C., with warming to about room temperature; to yield the corresponding compound of formula (VIII).

The compound of formula (VIII) is subjected to ring closure conditions; to yield the corresponding compound of formula (IX). For example, the compound of formula (VIII) may be reacted with a suitably selected catalyst such as Grubbs catalyst, Grubbs 2$^{nd}$ generation catalyst, Hoveyda-Grubbs Catalyst®, and Zhan catalyst, and the like; in a suitably selected solvent such as DCM, CHCl$_3$, and the like; at an elevated temperature, for example at about 50° C.; to yield the corresponding compound of formula (IX).

The compound of formula (IX) is reacted with bis(pinacolato)diborane, a known compound; in the presence of catalyst such as CuCl, Cu$_2$O, and the like; in the presence of a suitably selected ligand such as BINAP, and the like; in the presence of a suitably selected base such as NaOt-Bu, KOt-Bu, and the like; in a suitably selected solvent or mixture of solvents, such as a mixture of THF/MeOH, and the like;

and then reacted with peroxide, a known compound; at about room temperature; to yield the corresponding compound of formula (X).

The compound of formula (X) is reacted with a suitably selected agent such as PCC, MnO$_2$, Swern oxidation reagents, and the like; in a suitably selected solvent such as DCM, CHCl$_3$, and the like; at about room temperature; to yield the corresponding compound of formula (XI).

The compound of formula (XI) is reacted to install an oxygen protecting group; to yield the corresponding compound of formula (XII). For example, the compound of formula (XI) may be reacted with N-phenyl-trifluoromethane sulfonimide, a known compound; in the presence of a suitably selected organic amine base such as TEA, and the like; in a suitably selected solvent such as DCM, and the like; at about room temperature; to yield the corresponding compound of formula (XII) wherein PG$^2$ is Tf.

One skilled in the art will recognize that compounds of formula (XII) wherein the ring stereo-center is present in a stereo-isomeric excess of the corresponding R- or S-stereo-isomer may be similarly prepared as described in Scheme 1 above.

The resulting stereo-isomerically enriched compound of formula (XII) is then reacted as described in Schemes 2 below, to yield the corresponding compound of formula (I) wherein the ring stereo-center is present in a stereo-isomeric excess of the corresponding R- or S-stereo-isomer.

Compounds of formula (I-B) may be prepared from the corresponding compounds of formula (XII) as described in Scheme 2, below.

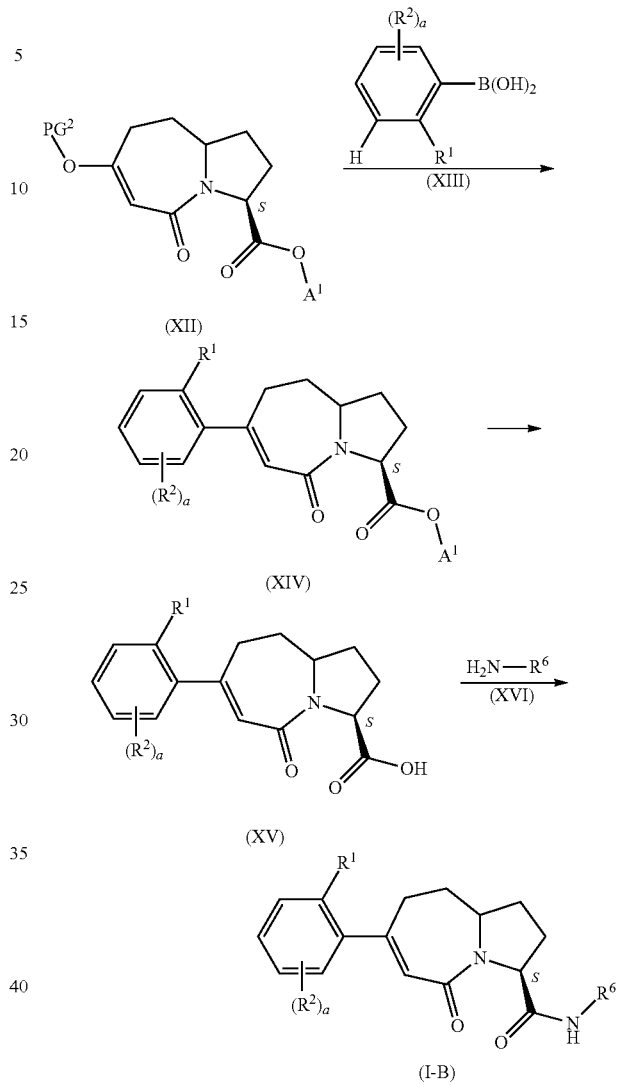

Scheme 2

Accordingly, a suitably substituted compound of formula (XII) is reacted with a suitably substituted compound of formula (XIII), a known compound or compound prepared by known methods, in the presence of a suitably selected catalyst such as Pd(PPh$_3$)$_4$, PdCl$_2$(dppf), Pd$_2$(dba)$_3$, and the like; in the presence of a suitably selected base such as K$_2$CO$_3$, Cs$_2$CO$_3$, K$_3$PO$_4$, and the like; in a suitably selected solvent such as 1,4-dioxane, DMF, toluene, and the like; to yield the corresponding compound of formula (XIV).

The compound of formula (XIV) is reacted with a suitably selected base such as LiOH, NaOH, KOH, and the like; in a suitably selected solvent or mixture of solvents such as a mixture of THF/MeOH/H$_2$O and the like; to yield the corresponding compound of formula (XV).

The compound of formula (XV) is reacted with a suitably substituted compound of formula (XVI), a known compound or compound prepared by known methods; in the presence of a suitably selected coupling agent such as EDCl, HATU, PyBOP, and the like; in the presence of a suitably selected organic amine base such as pyridine, DIEA, Et$_3$N, and the like; neat or in a suitably selected solvent such as DMF, DCM, THF, and the like; to yield the corresponding compound of formula (I-B).

Compounds of formula (I-A) may be prepared as described in Scheme 3, below.

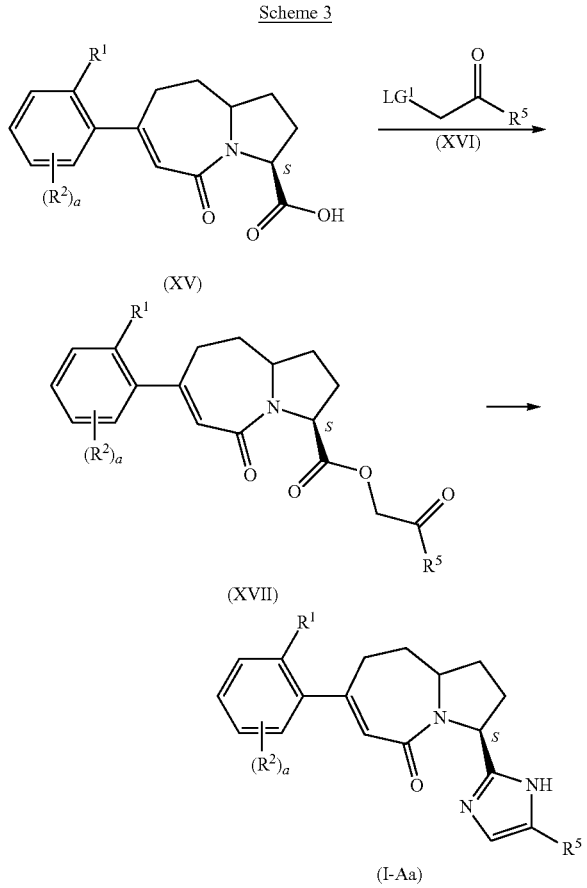

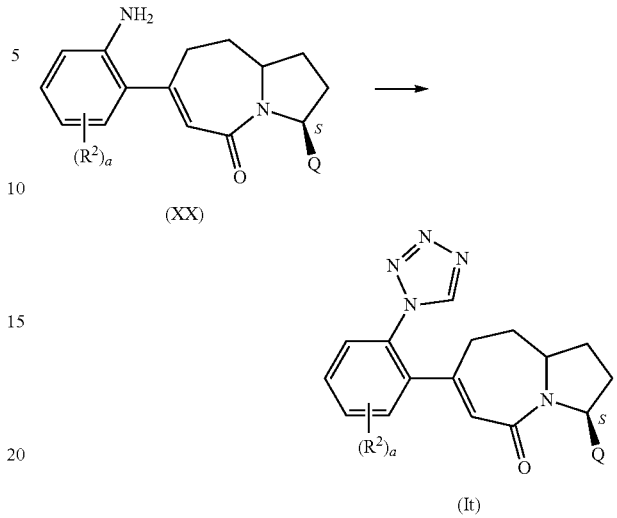

Accordingly, a suitably substituted compound of formula (XV), prepared for example as described herein, is reacted with a suitably substituted compound of formula (XVI), wherein $LG^1$ is a suitably selected leaving group such as Br, Cl, and the like, a known compound or compound prepared by known methods; in the presence of a suitably selected base such as $K_2CO_3$, $Na_2CO_3$, and the like; in a suitably selected solvent such as DMF, ACN, and the like; at about room temperature; to yield the corresponding compound of formula (XVII).

The compound or formula (XVII) is reacted to effect ring closure, according to known method, for example by reacting with $NH_4OAc$; in the presence of AcOH; in a suitably selected solvent such as toluene, and the like; at an elevated temperature, for example at about 110° C.; to yield the corresponding compound of formula (I-Aa).

Compounds of formula (I) wherein $R^4$ is halogen may be prepared as described in herein, by reacting a suitably substituted compound of formula (I-Aa) with a suitably selected halogenating agent such as NCS (for chloro), NBS (for bromo), NIS (for iodo), Selectfluor (forfluoro), and the like, in a suitably selected solvent such as DCM, DCE, ACN, THF, $Et_2O$, and the like; to yield the corresponding compound of formula (I-A) wherein $R^4$ is the corresponding halogen.

Compounds of formula (I) wherein $R^1$ is 1,2,3,4-tetrazol-1-yl may alternatively be prepared as described in Scheme 4, below.

Accordingly, a suitably substituted compound of formula (XX), a compound of formula (I) wherein $R^1$ is $NH_2$, prepared as described herein, is reacted with a suitably selected source of azides such as $TMSN_3$, $NaN_3$, and the like; in the presence of trimethoxymethyl in acetic acid; at an elevated temperature, for example to a temperature of about 80° C.; to yield the corresponding compound of formula (It).

One skilled in the art will recognize that compounds of formula (I) wherein $R^1$ is a nitrogen bound ring structure (other than 1,2,3,4-tetrazol-1-yl exemplified above) may be similarly prepared, by reacting a suitably substituted compound of formula (XX), prepared as described herein, with a suitably selected reagent, to yield the desired ring closure at the terminal $NH_2$ group, according to known methods, as would be readily recognized by those skilled in the art.

One skilled in the art will further recognize that various substituent groups and/or functional groups on said substituent groups (for example —OH, —$NH_2$, etc.) may be protected prior to any reaction step described above, and then de-protected at a later step in the synthesis, as would be desirable or necessary, according to methods well known to those skilled in the art.

As more extensively provided in this written description, terms such as "reacting" and "reacted" are used herein in reference to a chemical entity that is any one of: (a) the actually recited form of such chemical entity, and (b) any of the forms of such chemical entity in the medium in which the compound is being considered when named.

One skilled in the art will recognize that, where not otherwise specified, the reaction step(s) is performed under suitable conditions, according to known methods, to provide the desired product. One skilled in the art will further recognize that, in the specification and claims as presented herein, wherein a reagent or reagent class/type (e.g. base, solvent, etc.) is recited in more than one step of a process, the individual reagents are independently selected for each reaction step and may be the same of different from each other. For example wherein two steps of a process recite an organic or inorganic base as a reagent, the organic or inorganic base selected for the first step may be the same or different than the organic or inorganic base of the second step.

Further, one skilled in the art will recognize that wherein a reaction step of the present invention may be carried out in a variety of solvents or solvent systems, said reaction step may also be carried out in a mixture of the suitable solvents or solvent systems.

One skilled in the art will recognize that wherein a reaction step of the present invention may be carried out in a variety of solvents or solvent systems, said reaction step may also be carried out in a mixture of the suitable solvents or solvent systems.

One skilled in the art will further recognize that the reaction or process step(s) as herein described are allowed to proceed for a sufficient period of time until the reaction is complete, as determined by any method known to one skilled in the art, for example, chromatography (e.g. HPLC). In this context a "completed reaction or process step" shall mean that the reaction mixture contains a significantly diminished amount of the starting material(s)/reagent(s) and a significantly reduced amount of the desired product(s), as compared to the amounts of each present at the beginning of the reaction.

To provide a more concise description, some of the quantitative expressions given herein are not qualified with the term "about". It is understood that whether the term "about" is used explicitly or not, every quantity given herein is meant to refer to the actual given value, and it is also meant to refer to the approximation to such given value that would reasonably be inferred based on the ordinary skill in the art, including approximations due to the experimental and/or measurement conditions for such given value.

To provide a more concise description, some of the quantitative expressions herein are recited as a range from about amount X to about amount Y. It is understood that wherein a range is recited, the range is not limited to the recited upper and lower bounds, but rather includes the full range from about amount X through about amount Y, or any amount or range therein.

Examples of suitable solvents, bases, reaction temperatures, and other reaction parameters and components are provided in the detailed descriptions which follow herein. One skilled in the art will recognize that the listing of said examples is not intended, and should not be construed, as limiting in any way the invention set forth in the claims which follow thereafter.

As used herein, unless otherwise noted, the term "leaving group" shall mean a charged or uncharged atom or group which departs during a substitution or displacement reaction. Suitable examples include, but are not limited to, Br, Cl, I, mesylate, tosylate, and the like.

During any of the processes for preparation of the compounds of the present invention, it may be necessary and/or desirable to protect sensitive or reactive groups on any of the molecules concerned. This may be achieved by means of conventional protecting groups, such as those described in Protective Groups in Organic Chemistry, ed. J. F. W. McOmie, Plenum Press, 1973; and T. W. Greene & P. G. M. Wuts, Protective Groups in Organic Synthesis, John Wiley & Sons, 1991. The protecting groups may be removed at a convenient subsequent stage using methods known from the art.

As used herein, unless otherwise noted, the term "nitrogen protecting group" shall mean a group which may be attached to a nitrogen atom to protect said nitrogen atom from participating in a reaction and which may be readily removed following the reaction. Suitable nitrogen protecting groups include, but are not limited to carbamates—groups of the formula —C(O)O—R wherein R is for example methyl, ethyl, t-butyl, benzyl, phenylethyl, $CH_2=CH-CH_2-$, and the like; amides—groups of the formula —C(O)—R' wherein R' is for example methyl, phenyl, trifluoromethyl, and the like; N-sulfonyl derivatives—groups of the formula —$SO_2$—R" wherein R" is for example tolyl, phenyl, trifluoromethyl, 2,2,5,7,8-pentamethylchroman-6-yl-, 2,3,6-trimethyl-4-methoxybenzene, and the like. Other suitable nitrogen protecting groups may be measured in texts such as T. W. Greene & P. G. M. Wuts, Protective Groups in Organic Synthesis, John Wiley & Sons, 1991.

As used herein, unless otherwise noted, the term "oxygen protecting group" shall mean a group which may be attached to an oxygen atom to protect said oxygen atom from participating in a reaction and which may be readily removed following the reaction. Suitable oxygen protecting groups include, but are not limited to, acetyl, benzoyl, t-butyl-dimethylsilyl, trimethylsilyl (TMS), MOM, THP, and the like. Other suitable oxygen protecting groups may be measured in texts such as T. W. Greene & P. G. M. Wuts, Protective Groups in Organic Synthesis, John Wiley & Sons, 1991.

Where the processes for the preparation of the compounds according to the invention give rise to mixture of stereoisomers, these isomers may be separated by conventional techniques such as preparative chromatography. The compounds may be prepared in racemic form, or individual enantiomers may be prepared either by enantiospecific synthesis or by resolution. The compounds may, for example, be resolved into their component enantiomers by standard techniques, such as the formation of diastereomeric pairs by salt formation with an optically active acid, such as (−)-di-p-toluoyl-D-tartaric acid and/or (+)-di-p-toluoyl-L-tartaric acid followed by fractional crystallization and regeneration of the free base. The compounds may also be resolved by formation of diastereomeric esters or amides, followed by chromatographic separation and removal of the chiral auxiliary. Alternatively, the compounds may be resolved using a chiral HPLC column.

Additionally, chiral HPLC against a standard may be used to determine percent enantiomeric excess (% ee). The enantiomeric excess may be calculated as follows $$[(Rmoles-Smoles)/(Rmoles+Smoles)] \times 100\%$$

where Rmoles and Smoles are the R and S mole fractions in the mixture such that Rmoles+Smoles=1. The enantiomeric excess may alternatively be calculated from the specific rotations of the desired enantiomer and the prepared mixture as follows:

$$ee=([\alpha\text{-obs}]/[\alpha\text{-max}]) \times 100.$$

3. Utility

The compounds of the present invention are useful for the treatment and/or prophylaxis of thromboembolic disorders, inflammatory disorders and diseases or conditions in which factor XIa and/or plasma kallikrein activity is implicated.

In some embodiments, the present invention is directed to methods for the treatment and/or prophylaxis of a thromboembolic disorder comprising administering to a patient in need of such treatment and/or prophylaxis a therapeutically effective amount of a least one of the compounds as described herein, or a stereoisomer, isotopologue, or pharmaceutically acceptable salt thereof.

As used herein, the term "thromboembolic disorders" includes arterial cardiovascular thromboembolic disorders, venous cardiovascular or cerebrovascular thromboembolic disorders, and thromboembolic disorders in the chambers of the heart or in the peripheral circulation. The term "thromboembolic disorders" as used herein also includes specific disorders selected from, but not limited to, unstable angina or other acute coronary syndromes, atrial fibrillation, first or recurrent myocardial infarction, ischemic sudden death, transient ischemic attack, stroke, atherosclerosis, peripheral occlusive arterial disease, venous thrombosis, deep vein thrombosis, thrombophlebitis, arterial embolism, coronary arterial thrombosis, cerebral arterial thrombosis, cerebral embolism, kidney embolism, pulmonary embolism, and thrombosis resulting from medical implants, devices, or procedures in which blood is exposed to an artificial surface that promotes thrombosis. The medical implants or devices include, but are not limited to: prosthetic valves, artificial valves, indwelling catheters, stents, blood oxygenators, shunts, vascular access ports, ventricular assist devices and artificial hearts or heart chambers, and vessel grafts. The procedures include, but are not limited to: cardiopulmonary bypass, percutaneous coronary intervention, and hemodialysis. In some embodiments, the term "thromboembolic disorders" includes acute coronary syndrome, stroke, deep vein thrombosis, and pulmonary embolism. In some embodiments, the "thromboembolic disorders" include hereditary angioedema (HAE) and diabetic macular edema (DME).

In some embodiments, the present invention is directed to methods for the treatment and/or prophylaxis of an inflammatory disorder comprising: administering to a patient in need of such treatment and/or prophylaxis a therapeutically effective amount of at least one of the compounds of the present invention or a stereoisomer, isotopologue, or pharmaceutically acceptable salt thereof. Examples of the inflammatory disorders include, but are not limited to, sepsis, acute respiratory distress syndrome, and systemic inflammatory response syndrome.

In some embodiments, the present invention is directed to methods for the treatment and/or prophylaxis of a disease or condition in which plasma kallikrein activity is implicated, comprising administering to a patient in need of such treatment and/or prophylaxis a therapeutically effective amount of at least one of the compounds of the present invention or a stereoisomer, isotopologue, or pharmaceutically acceptable salt thereof. The diseases or conditions in which plasma kallikrein activity is implicated include, but are not limited to, impaired visual acuity, diabetic retinopathy, diabetic macular edema, hereditary angioedema, diabetes, pancreatitis, nephropathy, cardiomyopathy, neuropathy, inflammatory bowel disease, arthritis, inflammation, septic shock, hypotension, cancer, adult respiratory distress syndrome, disseminated intravascular coagulation, and cardiopulmonary bypass surgery.

In some embodiments, the present invention provides a method for treating the primary prophylaxis of a thromboembolic disorder. In some embodiments, the present invention provides a method for the primary prophylaxis of a thromboembolic disorder wherein the thromboembolic disorder is selected from unstable angina, an acute coronary syndrome, atrial fibrillation, myocardial infarction, ischemic sudden death, transient ischemic attack, stroke, atherosclerosis, peripheral occlusive arterial disease, venous thrombosis, deep vein thrombosis, thrombophlebitis, arterial embolism, coronary arterial thrombosis, cerebral arterial thrombosis, cerebral embolism, kidney embolism, pulmonary embolism, and thrombosis resulting from medical implants, devices, or procedures in which blood is exposed to an artificial surface that promotes thrombosis. In another embodiment, the present invention provides a method for the primary prophylaxis of a thromboembolic disorder, wherein the thromboembolic disorder is selected from acute coronary syndrome, stroke, venous thrombosis, and thrombosis resulting from medical implants and devices.

In some embodiments, the present invention provides a method for the secondary prophylaxis of a thromboembolic disorder. In some embodiments, the present invention provides a method for the secondary prophylaxis of a thromboembolic disorder. wherein the thromboembolic disorder is selected from unstable angina, an acute coronary syndrome, atrial fibrillation, recurrent myocardial infarction, transient ischemic attack, stroke, atherosclerosis, peripheral occlusive arterial disease, venous thrombosis, deep vein thrombosis, thrombophlebitis, arterial embolism, coronary arterial thrombosis, cerebral arterial thrombosis, cerebral embolism, kidney embolism, pulmonary embolism, and thrombosis resulting from medical implants, devices, or procedures in which blood is exposed to an artificial surface that promotes thrombosis. In another embodiment, the present invention provides a method for the secondary prophylaxis of a thromboembolic disorder, wherein the thromboembolic disorder is selected from acute coronary syndrome, stroke, atrial fibrillation and venous thrombosis.

One skilled in the art will recognize that wherein the present invention is directed to methods of prophylaxis, the subject in need thereof (i.e. a subject in need of prophylaxis) shall include any subject or patient (preferably a mammal, more preferably a human) who has experienced or exhibited at least one symptom of the disorder, disease or condition to be prevented. Further, a subject in need thereof may additionally be a subject (preferably a mammal, more preferably a human) who has not exhibited any symptoms of the disorder, disease or condition to be prevented, but who has been deemed by a physician, clinician or other medical profession to be at risk of developing said disorder, disease or condition. For example, the subject may be deemed at risk of developing a disorder, disease or condition (and therefore in need of prophylaxis or prophylactic treatment) as a consequence of the subject's medical history, including, but not limited to, family history, pre-disposition, co-existing (comorbid) disorders or conditions, genetic testing, and the like.

The compounds of the present invention are preferably administered alone to a mammal in a therapeutically effective amount. However, the compounds of the invention can also be administered in combination with an additional therapeutic agent, as defined below, to a mammal in a therapeutically effective amount. When administered in a combination, the combination of compounds is preferably, but not necessarily, a synergistic combination. Synergy, for example, may occur when the effect (in this case, inhibition of the desired target) of the compounds when administered in combination is greater than the additive effect of the compounds when administered alone as a single agent. In general, a synergistic effect is most clearly demonstrated at suboptimal concentrations of the compounds. Synergy can be in terms of lower cytotoxicity, increased anticoagulant effect, or some other beneficial effect of the combination compared with the individual components. Possible favorable outcomes of treatment with a synergistic combination include, but are not limited to, (a) increased efficacy of the therapeutic effect, (b) ability to administer decreased dosage while increasing or maintaining efficacy (which in turn may also result in decreased toxicity and/or adverse side effects), (c) minimized or slowed development of drug resistance, (d) selective synergism against the biological target (or efficacy synergism) versus host (toxicity antagonism).

In some embodiments of the present invention, the compound of formula (I) may be administered in combination with one or more anticoagulant, anti-thrombin agent, antiplatelet agent, fibrinolytic, hypolipidemic agent, antihypertensive agent, and/or anti-ischemic agent. Suitable examples include, but are not limited to warfarin, heparin, aprotinin, a synthetic pentasaccharide, a boroarginine derivative, a boropeptide, heparin, hirudin, argatroban, a thromboxane-A2-receptor antagonist, a thromboxane-A2-synthetase inhibitor, a PDE-III inhibitor, a PDE V inhibitor, an ADP receptor antagonist, an antagonist of the purinergic receptor P2Y1, an antagonist of the purinergic receptor P2Y12, tissue plasminogen activator and modified forms thereof, anistreplase, urokinase, streptokinase, tenecteplase, lanoteplase, a PAI-I inhibitor, an alpha-2-antiplasmin inhibitor, an anisoylated plasminogen streptokinase activator complex, a HMG-CoA reductase inhibitor, a squalene synthetase inhibitor, a fibrate, a bile acid sequestrant, an ACAT inhibitor, a MTP inhibitor, a lipooxygenase inhibitor, a cholesterol absorption inhibitor, a cholesterol ester transfer protein inhibitor, an alpha adrenergic blocker, a beta adrenergic blocker, a calcium channel blocker, a diuretic, a renin inhibitor, an angiotensin-converting enzyme inhibitor, an angiotensin-II-receptor antagonist, an ET receptor antagonist, a Dual ET/A11 antagonist, a neutral endopeptidase inhibitor, a vasopeptidase inhibitor, a Class I agent, a Class II agent, a Class III agent, a Class IV agent, an IAch inhibitor, an IKur inhibitor and a cardiac glycoside.

By "administered in combination" or "combination therapy" it is meant that the compound of the present invention and one or more additional therapeutic agents are administered concurrently or consecutively to the subject (preferably mammal, more preferably human) being treated. When administered in combination each component may be administered at the same time or sequentially in any order at different points in time. Thus, each component may be administered separately but sufficiently closely in time so as to provide the desired therapeutic effect. Chou, Theoretical Basis, Experimental Design, and Computerized Simulation of Synergism and Antagonism in Drug Combination Studies, Pharmacol Rev., 2006, vol. 58, 621-681.

4. Pharmaceutical Compositions

The present invention further comprises pharmaceutical compositions containing a compound of formula (I) with a pharmaceutically acceptable carrier. Pharmaceutical compositions containing one or more of the compounds of the invention described herein as the active ingredient can be prepared by intimately mixing the compound or compounds with a pharmaceutical carrier according to conventional pharmaceutical compounding techniques. The carrier may take a wide variety of forms depending upon the desired route of administration (e.g., oral, parenteral). Thus, for liquid oral preparations such as suspensions, elixirs and solutions, suitable carriers and additives include water, glycols, oils, alcohols, flavoring agents, preservatives, stabilizers, coloring agents and the like, for solid oral preparations, such as powders, capsules and tablets, suitable carriers and additives include starches, sugars, diluents, granulating agents, lubricants, binders, disintegrating agents and the like. Solid oral preparations may also be coated with substances such as sugars or be enteric-coated so as to modulate major site of absorption. For parenteral administration, the carrier will usually consist of sterile water and other ingredients may be added to increase solubility or preservation. Injectable suspensions or solutions may also be prepared utilizing aqueous carriers along with appropriate additives.

To prepare the pharmaceutical compositions of this invention, one or more compounds of the present invention as the active ingredient is intimately admixed with a pharmaceutical carrier according to conventional pharmaceutical compounding techniques, which carrier may take a wide variety of forms depending of the form of preparation desired for administration, e.g., oral or parenteral such as intramuscular. In preparing the compositions in oral dosage form, any of the usual pharmaceutical media may be employed. Thus, for liquid oral preparations, such as for example, suspensions, elixirs and solutions, suitable carriers and additives include water, glycols, oils, alcohols, flavoring agents, preservatives, coloring agents and the like; for solid oral preparations such as, for example, powders, capsules, caplets, gelcaps and tablets, suitable carriers and additives include starches, sugars, diluents, granulating agents, lubricants, binders, disintegrating agents and the like.

Because of their ease in administration, tablets and capsules represent the most advantageous oral dosage unit form, in which case solid pharmaceutical carriers are obviously employed. If desired, tablets may be sugar coated or enteric coated by standard techniques. For parenterals, the carrier will usually comprise sterile water, through other ingredients, for example, for purposes such as aiding solubility or for preservation, may be included. Injectable suspensions may also be prepared, in which case appropriate liquid carriers, suspending agents and the like may be employed. The pharmaceutical compositions herein will contain, per dosage unit, e.g., tablet, capsule, powder, injection, teaspoonful and the like, an amount of the active ingredient necessary to deliver an effective dose as described above. The pharmaceutical compositions herein will contain, per unit dosage unit, e.g., tablet, capsule, powder, injection, suppository, teaspoonful and the like, of from about 0.01 mg to about 1000 mg or any amount or range therein, and may be given at a dosage of from about 0.05 mg/day to about 1000 mg/day, or any amount or range therein, about 0.1 mg/day to about 500 mg/day, or any amount or range therein, preferably from about 1 mg/day to about 300 mg/day, or any amount or range therein.

The dosages, however, may be varied depending upon the requirement of the patients, the severity of the condition being treated and the compound being employed. The use of either daily administration or post-periodic dosing may be employed.

Preferably these compositions are in unit dosage forms such as tablets, pills, capsules, powders, granules, sterile parenteral solutions or suspensions, metered aerosol or liquid sprays, drops, ampoules, autoinjector devices or suppositories; for oral parenteral, intranasal, sublingual or rectal administration, or for administration by inhalation or insufflation. Alternatively, the composition may be presented in a form suitable for once-weekly or once-monthly administration; for example, an insoluble salt of the active compound, such as the decanoate salt, may be adapted to provide a depot preparation for intramuscular injection. For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid pre-formulation composition containing a homogeneous mixture of a compound of the present invention, or a pharmaceutically acceptable salt thereof. When referring to these pre-formulation compositions as homogeneous, it is meant that the active ingredient is dispersed evenly throughout the composition so that the composition may be readily subdivided into equally effective dosage forms such as tablets, pills and capsules. This solid pre-formulation composition is then subdivided into unit dosage forms of the type described above containing from about 0.01 mg to about 1,000 mg, or any amount or range therein, of the active ingredient of the present invention. The tablets or pills of the novel composition can be coated or otherwise compounded to provide a dosage form yielding the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of material can be used for such enteric layers or coatings, such materials including a number of polymeric acids with such materials as shellac, cetyl alcohol and cellulose acetate.

The liquid forms in which the novel compositions of the present invention may be incorporated for administration orally or by injection include, aqueous solutions, suitably flavored syrups, aqueous or oil suspensions, and flavored emulsions with edible oils such as cottonseed oil, sesame oil, coconut oil or peanut oil, as well as elixirs and similar pharmaceutical vehicles. Suitable dispersing or suspending agents for aqueous suspensions, include synthetic and natural gums such as tragacanth, acacia, alginate, dextran, sodium carboxymethylcellulose, methylcellulose, polyvinyl-pyrrolidone or gelatin.

The method of the treatment and/or prophylaxis of thromboembolic disorders described in the present invention may also be carried out using a pharmaceutical composition comprising any of the compounds as defined herein and a pharmaceutically acceptable carrier. The pharmaceutical composition may contain between about 0.01 mg and about 1000 mg of the compound, or any amount or range therein, preferably from about 0.05 mg to about 300 mg of the compound, or any amount or range therein, more preferably from about 0.1 mg to about 100 mg of the compound, or any amount or range therein, more preferably from about 0.1 mg to about 50 mg of the compound, or any amount or range therein; and may be constituted into any form suitable for the mode of administration selected. Carriers include necessary and inert pharmaceutical excipients, including, but not limited to, binders, suspending agents, lubricants, flavorants, sweeteners, preservatives, dyes, and coatings. Compositions suitable for oral administration include solid forms, such as pills, tablets, caplets, capsules (each including immediate release, timed release and sustained release formulations), granules, and powders, and liquid forms, such as solutions, syrups, elixirs, emulsions, and suspensions. Forms useful for parenteral administration include sterile solutions, emulsions and suspensions.

Advantageously, compounds of the present invention may be administered in a single daily dose, or the total daily dosage may be administered in divided doses of two, three or four times daily. Furthermore, compounds for the present invention can be administered in intranasal form via topical use of suitable intranasal vehicles, or via transdermal skin patches well known to those of ordinary skill in that art. To be administered in the form of a transdermal delivery system, the dosage administration will, of course, be continuous rather than intermittent throughout the dosage regimen.

For instance, for oral administration in the form of a tablet or capsule, the active drug component can be combined with an oral, non-toxic pharmaceutically acceptable inert carrier such as ethanol, glycerol, water and the like. Moreover, when desired or necessary, suitable binders; lubricants, disintegrating agents and coloring agents can also be incorporated into the mixture. Suitable binders include, without limitation, starch, gelatin, natural sugars such as glucose or beta-lactose, corn sweeteners, natural and synthetic gums such as acacia, tragacanth or sodium oleate, sodium stearate, magnesium stearate, sodium benzoate, sodium acetate, sodium chloride and the like. Disintegrators include, without limitation, starch, methyl cellulose, agar, bentonite, xanthan gum and the like.

The liquid forms may include suitably flavored suspending or dispersing agents such as the synthetic and natural gums, for example, tragacanth, acacia, methyl-cellulose and the like. For parenteral administration, sterile suspensions and solutions are desired. Isotonic preparations which generally contain suitable preservatives are employed when intravenous administration is desired.

To prepare a pharmaceutical composition of the present invention, a compound of formula (I) as the active ingredient is intimately admixed with a pharmaceutical carrier according to conventional pharmaceutical compounding techniques, which carrier may take a wide variety of forms depending of the form of preparation desired for administration (e.g. oral or parenteral). Suitable pharmaceutically acceptable carriers are well known in the art. Descriptions of some of these pharmaceutically acceptable carriers may be measured in The Handbook of Pharmaceutical Excipients, published by the American Pharmaceutical Association and the Pharmaceutical Society of Great Britain. Methods of formulating pharmaceutical compositions have been described in numerous publications such as Pharmaceutical Dosage Forms: Tablets, Second Edition, Revised and Expanded, Volumes 1-3, edited by Lieberman et al; Pharmaceutical Dosage Forms: Parenteral Medications, Volumes 1-2, edited by Avis et al; and Pharmaceutical Dosage Forms: Disperse Systems, Volumes 1-2, edited by Lieberman et al; published by Marcel Dekker, Inc.

Compounds of the present invention may be administered in any of the foregoing compositions and according to dosage regimens established in the art whenever treatment or prophylaxis of thromboembolic disorders, inflammatory disorders or diseases or conditions in which plasma kallikrein activity is implicated is required.

The daily dosage of the products may be varied over a wide range from about 0.01 mg to about 1,000 mg per adult human per day, or any amount or range therein. For oral administration, the compositions are preferably provided in the form of tablets containing, 0.01, 0.05, 0.1, 0.5, 1.0, 2.5, 5.0, 10.0, 15.0, 25.0, 50.0, 100, 150, 200, 250 and 500 milligrams of the active ingredient for the symptomatic adjustment of the dosage to the patient to be treated. An effective amount of the drug may be ordinarily supplied at a dosage level of from about 0.005 mg/kg to about 10 mg/kg of body weight per day, or any amount or range therein. Preferably, the range is from about 0.01 to about 5.0 mg/kg of body weight per day, or any amount or range therein, more preferably, from about 0.1 to about 1.0 mg/kg of body weight per day, or any amount or range therein, more preferably, from about 0.1 to about 0.5 mg/kg of body weight per day, or any amount or range therein. The compounds may be administered on a regimen of 1 to 4 times per day.

Optimal dosages to be administered may be readily determined by those skilled in the art, and will vary with the particular compound used, the mode of administration, the strength of the preparation, and the advancement of the disease condition. In addition, factors associated with the particular patient being treated, including patient age, weight, diet and time of administration, will result in the need to adjust dosages.

One skilled in the art will recognize that, both in vivo and in vitro trials using suitable, known and generally accepted cell and/or animal models are predictive of the ability of a test compound to treat or prevent a given disorder.

One skilled in the art will further recognize that human clinical trials including first-in-human, dose ranging and efficacy trials, in healthy patients and/or those suffering from a given disorder, may be completed according to methods well known in the clinical and medical arts.

5. Combination Therapy

One or more additional pharmacologically active agents may be administered in combination with the compounds of the invention. The additional active agent (or agents) is intended to mean a pharmaceutically active agent (or agents) that is active in the body, including pro-drugs that convert to pharmaceutically active form after administration, which is different from the compound of formula (I), and also includes free-acid, free-base and pharmaceutically acceptable salts of said additional active agents when such forms are sold commercially or are otherwise chemically possible. Generally, any suitable additional active agent or agents, including but not limited to antihypertensive agents, additional diuretics, anti-atherosclerotic agents such as a lipid modifying compound, anti-diabetic agents and/or anti-obesity agents may be used in any combination with the compound of formula (I) in a single dosage formulation (a fixed dose drug combination), or may be administered to the patient in one or more separate dosage formulations which allows for concurrent or sequential administration of the active agents (co-administration of the separate active agents).

Examples of additional active agents which may be employed include but are not limited to angiotensin converting enzyme inhibitors (e.g, alacepril, benazepril, captopril, ceronapril, cilazapril, delapril, enalapril, enalaprilat, fosinopril, imidapril, lisinopril, moveltipril, perindopril, quinapril, ramipril, spirapril, temocapril, or trandolapril); angiotensin receptor antagonists also known as angiotensin receptor blockers or ARBs (e.g., losartan i.e., COZAAR®, valsartan, candesartan, olmesartan, telmesartan, eprosartan, irbesartan and any of these drugs used in combination with hydrochlorothiazide such as HYZAAR®); diuretics, e.g. hydrochlorothiazide (HCTZ); potassium sparing diuretics such as amiloride HCl, spironolactone, epleranone, triamterene, each with or without HCTZ; neutral endopeptidase inhibitors (e.g., thiorphan and phosphoramidon); aldosterone antagonists; aldosterone synthase inhibitors; renin inhibitors (e.g. urea derivatives of di- and tri-peptides (See U.S. Pat. No. 5,116,835), amino acids and derivatives (U.S. Pat. Nos. 5,095,119 and 5,104,869), amino acid chains linked by non-peptidic bonds (U.S. Pat. No. 5,114,937), di- and tri-peptide derivatives (U.S. Pat. No. 5,106,835), peptidyl amino diols (U.S. Pat. Nos. 5,063,208 and 4,845,079) and peptidyl beta-aminoacyl aminodiol carbamates (U.S. Pat. No. 5,089,471); also, a variety of other peptide analogs as disclosed in the following U.S. Pat. Nos. 5,071,837; 5,064,965; 5,063,207; 5,036,054; 5,036,053; 5,034,512 and 4,894,437, and small molecule renin inhibitors (including diol sulfonamides and sulfinyls (U.S. Pat. No. 5,098,924), N-morpholino derivatives (U.S. Pat. No. 5,055,466), N-heterocyclic alcohols (U.S. Pat. No. 4,885,292) and pyrrolimidazolones (U.S. Pat. No. 5,075,451); also, pepstatin derivatives (U.S. Pat. No. 4,980,283) and fluoro- and chloro-derivatives of statone-containing peptides (U.S. Pat. No. 5,066,643); enalkrein; RO 42-5892 (CAS Registry Number 126222-34-2, also known as remikiren); A 65317 (CAS Registry Number 119625-78-4); CP 80794 (CAS Registry Number 119625-78-4, also known as terlakiren)); ES 1005 (CAS Registry Number 115404-79-0); ES 8891 (CAS Registry Number 129445-88-1); SQ 34017 (CAS Registry Number 695226-77-8); aliskiren (2(S),4(S),5(S),7(S)—N-(2-carbamoyl-2-methylpropyl)-5-amino-4-hydroxy-2,7-diisopropyl-8-[4-methoxy-3-(3-methoxypropoxy)-phenyl]-octanamide hemifumarate); endothelin receptor antagonists; vasodilators (e.g. nitroprusside); calcium channel blockers (e.g., amlodipine, nifedipine, verapamil, diltiazem, felodipine, gallopamil, niludipine, nimodipine, nicardipine); potassium channel activators (e.g., nicorandil, pinacidil, cromakalim, minoxidil, aprilkalim, loprazolam); sympatholitics; beta-adrenergic blocking drugs (e.g., acebutolol, atenolol, betaxolol, bisoprolol, carvedilol, metoprolol, metoprolol tartate, nadolol, propranolol, sotalol, timolol); alpha adrenergic blocking drugs (e.g., doxazocin, prazocin or alpha methyldopa); central alpha adrenergic agonists; peripheral vasodilators (e.g. hydralazine); lipid lowering agents, e.g., HMG-CoA reductase inhibitors such as simvastatin and lovastatin which are marketed as ZOCOR® and MEVACOR® in lactone pro-drug form and function as inhibitors after administration, and pharmaceutically acceptable salts of dihydroxy open ring acid HMG-CoA reductase inhibitors such as atorvastatin (particularly the calcium salt sold in LIPITOR®), rosuvastatin (particularly the calcium salt sold in CRESTOR®), pravastatin (particularly the sodium salt sold in PRAVACHOL®), and fluvastatin (particularly the sodium salt sold in LESCOL®); a cholesterol absorption inhibitor such as ezetimibe (ZETIA®), and ezetimibe in combination with any other lipid lowering agents such as the HMG-CoA reductase inhibitors noted above and particularly with simvastatin (VYTORIN®) or with atorvastatin calcium; niacin in immediate-release or controlled release forms, and particularly niacin in combination with a DP antagonist such as laropiprant (TREDAPTIVE®) and/or with an HMG-CoA reductase inhibitor; niacin in immediate-release or controlled release forms, and particularly niacin in combination with a DP antagonist such as laropiprant (TREDAPTIVE®) and/or with an HMG-CoA reductase inhibitor; niacin receptor agonists such as acipimox and acifran, as well as niacin receptor partial agonists; metabolic altering agents including insulin sensitizing agents and related compounds for the treatment of diabetes such as biguanides (e.g., metformin), meglitinides (e.g., repaglinide, nateglinide), sulfonylureas (e.g., chlorpropamide, glimepiride, glipizide, glyburide, tolazamide, tolbutamide), thiazolidinediones also referred to as glitazones (e.g., pioglitazone, rosiglitazone), alpha glucosidase inhibitors (e.g., acarbose, miglitol), dipeptidyl peptidase inhibitors, (e.g., sitagliptin (JANUVIA®), alogliptin, vildagliptin, saxagliptin, linagliptin, dutogliptin, gemigliptin), ergot alkaloids (e.g., bromocriptine), combination medications such as JANUMET® (sitagliptin with metformin), and injectable diabetes medications such as exenatide and pramlintide acetate; or with other drugs beneficial for the prevention or the treatment of the above-mentioned diseases including but not limited to diazoxide; and including the free-acid, free-base, and pharmaceutically acceptable salt forms of the above active agents where chemically possible. Compounds which can be alternatively or additionally administered in combination with the compounds of the present invention include, but are not limited to, anticoagulants, anti-thrombin agents, anti-platelet agents, fibrinolytics, hypolipidemic agents, antihypertensive agents, and anti-ischemic agents.

Anticoagulant agents (or coagulation inhibitory agents) that may be used in combination with the compounds of this invention include warfarin, heparin (either unfractionated heparin or any commercially available low molecular weight heparin, for example enoxaparin and dalteparin), aprotinin, synthetic pentasaccharide inhibitors of Factor Xa such as fondaparinux and idraparinux, direct Factor Xa inhibitors such as rivaroxaban, apixaban, betrixaban, edoxaban, otamixaban, direct acting thrombin inhibitors including hirudin, dabigatran, argatroban, ximelagatran, melagatran, lepirudin, desirudin, and bivalirudin, as well as other factor VIIa inhibitors, VIIIa inhibitors, IXa inhibitors, Xa inhibitors, XIa inhibitors, fibrinogen receptor antagonists (including abciximab, eptifibatide and tirofiban), TAFI inibitors, and others known in the art. Factor IXa inhibitors include synthetic active-site blocked competitive inhibitors, oral inhibitors and RNA aptamers. These are described in Howard, E L, Becker K C, Rusconi, C P, Becker R C. Factor IXa Inhibitors as Novel Anticoagulents. Arterioscler Thromb Vasc Biol, 2007; 27: 722-727.

The term "anti-platelet agents" or "platelet inhibitory agents", as used herein, denotes agents that inhibit platelet function, for example, by inhibiting the aggregation, adhesion or granular secretion of platelets. Such agents include, but are not limited to, the various known non-steroidal anti-inflammatory drugs (NSAIDS) such as aspirin, ibuprofen, naproxen, sulindac, indomethacin, mefenamate, droxicam, diclofenac, sulfinpyrazone, and piroxicam, including pharmaceutically acceptable salts or prodrugs thereof. Of the NSAIDS, aspirin (acetylsalicylic acid or ASA), and piroxicam are preferred. Other suitable platelet inhibitory agents include IIb/IIIa antagonists (e.g., tirofiban, eptifibatide, and abciximab), thromboxane-A2-receptor antagonists (e.g., ifetroban), thromboxane-A2-synthetase inhibitors, phosphodiesterase-III (PDE-III) inhibitors (e.g., dipyridamole, cilostazol), and PDE V inhibitors (such as sildenafil), and pharmaceutically acceptable salts or prodrugs thereof.

The term "anti-platelet agents" or "platelet inhibitory agents", as used herein, is also intended to include ADP (adenosine diphosphate) receptor antagonists, preferable antagonists of the purinergic receptors P2Y1 and P2Y12 with P2Y12 being even more preferred. Preferred P2Y12 receptor antagonists include ticlopidine, prasugrel, clopidogrel, elinogrel, ticagrelor and cangrelor, including pharmaceutically acceptable salts or prodrugs thereof. Clopidogrel is an even more preferred agent. Ticlopidine and clopidogrel are also preferred compounds since they are known to be gentle on the gastro-intestinal tract in use. The compounds of the present invention may also be dosed in combination with aprotinin.

The term "thrombin inhibitors" or "anti-thrombin agents", as used herein, denotes inhibitors of the serine protease thrombin. By inhibiting thrombin, various thrombin-mediated processes, such as thrombin-mediated platelet activation (that is, for example, the aggregation of platelets, and/or the granular secretion of plasminogen activator inhibitor-1 and/or serotonin), endothelial cell activation, inflammatory reactions, and/or fibrin formation are disrupted. A number of thrombin inhibitors are known to one of skill in the art and these inhibitors are contemplated to be used in combination with the present compounds. Such inhibitors include, but are not limited to, boroarginine derivatives, boropeptides, heparins, hirudin, dabigatran and argatroban, including pharmaceutically acceptable salts and prodrugs thereof.

Boroarginine derivatives and boropeptides include N-acetyl and peptide derivatives of boronic acid, such as C-terminal alpha-aminoboronic acid derivatives of lysine, ornithine, arginine, homoarginine and corresponding isothiouronium analogs thereof. The term "hirudin", as used herein, includes suitable derivatives or analogs of hirudin, referred to herein as hirulogs, such as disulfatohirudin.

The term "thrombin receptor antagonists", also known as protease activated receptor (PAR) antagonists or PAR-1 antagonists, are useful in the treatment of thrombotic, inflammatory, atherosclerotic and fibroproliferative disorders, as well as other disorders in which thrombin and its receptor play a pathological role. Thrombin receptor antagonist peptides have been identified based on structure-activity studies involving substitutions of amino acids on thrombin receptors. In Bernatowicz et al, J Med. Chem., vol. 39, pp. 4879-4887 (1996), tetra- and pentapeptides are disclosed as being potent thrombin receptor antagonists, for example N-trans-cinnamoyl-p-fluoroPhe-p-guanidinoPhe-Leu-Arg-$NH_2$ and N-trans-cinnamoyl-p-fluoroPhe-p-guanidinoPhe-Leu-Arg-Arg-$NH_2$. Peptide thrombin receptor antagonists are also disclosed in WO 94/03479. Substituted tricyclic thrombin receptor antagonists are disclosed in U.S. Pat. Nos. 6,063,847, 6,326,380 and WO 01/96330. Other thrombin receptor antagonists include those disclosed in U.S. Pat. Nos. 7,304,078; 7,235,567; 7,037,920; 6,645,987; and EP Patent Nos. EP1495018 and EP1294714.

The term thrombolytic (or fibrinolytic) agents (or thrombolytics or fibrinolytics), as used herein, denotes agents that lyse blood clots (thrombi). Such agents include tissue plasminogen activator (TPA, natural or recombinant) and modified forms thereof, anistreplase, urokinase, streptokinase, tenecteplase (TNK), lanoteplase (nPA), factor VIIa inhibitors, PAI-I inhibitors (i.e., inactivators of tissue plasminogen activator inhibitors), alpha-2-antiplasmin inhibitors, and anisoylated plasminogen streptokinase activator complexes, including pharmaceutically acceptable salts or prodrugs thereof. The term anistreplase, as used herein, refers to anisoylated plasminogen streptokinase activator complexes. The term urokinase, as used herein, is intended to denote both dual and single chain urokinase, the latter also being referred to herein as prourokinase. Examples of suitable anti-arrhythmic agents for use in combination with the present compounds include: Class I agents (such as propafenone); Class II agents (such as carvedilol and propranolol); Class III agents (such as sotalol, dofetilide, aminodarone, azimilide and ibutilide); Class IV agents (such as ditiazem and verapamil); IAch inhibitors, and IKur inhibitors (e.g., compounds such as those disclosed in WO01/40231).

6. Definitions

As used herein, unless otherwise noted, "halogen" shall mean chloro, bromo, fluoro and iodo, preferably bromo, fluoro or chloro, more preferably fluoro or chloro.

As used herein, unless otherwise noted, the term "oxo" shall mean a functional group of the structure =O (i.e. a substituent oxygen atom connected to another atom by a double bond).

As used herein, unless otherwise noted, the term "$C_{X-Y}$alkyl" wherein X and Y are integers, whether used alone or as part of a substituent group, include straight and branched chains containing between X and Y carbon atoms. For example, $C_{1-4}$alkyl radicals include straight and branched chains of between 1 and 4 carbon atoms, including methyl, ethyl, propyl, isopropyl, butyl, isobutyl, sec-butyl and t-butyl.

As used herein, unless otherwise noted, the terms "—($C_{X-Y}$alkylene)- and —$C_{X-Y}$alkylene-" wherein X and Y are integers, shall denote any $C_{X-Y}$alkyl carbon chain as herein defined, wherein said $C_{X-Y}$alkyl chain is divalent and is further bound through two points of attachment, preferably through two terminal carbon atoms.

As used herein, unless otherwise noted, the term "hydroxy substituted $C_{1-4}$alkyl" shall mean any $C_{1-4}$alkyl group as defined above substituted with at least one hydroxy (—OH) groups, preferably one to three, more preferably one to two hydroxy groups. Suitable examples include but are not limited to —$CH_2OH$, —$CH_2CH_2OH$, —$CH(OH)CH_3$, —$CH(OH)CH_2OH$, —$CH_2CH_2CH_2OH$, —$C(CH_2OH)_3$, and the like.

As used herein, unless otherwise noted, the term "fluorinated $C_{1-4}$alkyl" shall mean any $C_{1-4}$alkyl group as defined above substituted with one or more fluoro groups, preferably one to three fluoro group. Suitably examples include, but are not limited to —$CH_2F$, —$CHF_2$, —$CF_3$, —$CH_2$—$CF_3$, —$CF_2$—$CH_3$, —$CH_2$—$CH_2$—$CH_2F$, —$CH_2$—$CH_2$—$CF_3$, —$C(CH_3)_2CF_3$, —$C(CF_3)_3$, and the like.

As used herein, unless otherwise noted, "$C_{X-Y}$alkoxy" wherein X and Y are integers, shall mean an oxygen ether radical of the above described straight or branched chain $C_{X-Y}$alkyl groups containing between X and Y carbon atoms. For example, $C_{1-4}$alkoxy shall include methoxy, ethoxy, n-propoxy, isopropoxy, n-butyloxy, iso-butyloxy, sec-butyloxy and tert-butyloxy.

As used herein, unless otherwise noted, the term "fluorinated $C_{1-4}$alkoxy" shall mean any $C_{1-4}$alkoxy group as defined above substituted with one or more fluoro groups, preferably one to three fluoro group. Suitably examples include, but are not limited to —$OCH_2F$, —$OCHF_2$, —$OCF_3$, —O—$CH_2$—$CF_3$, —O—$CF_2$—$CH_3$, —O—$CH_2$—$CH_2$—$CH_2F$, —O—$CH_2$—$CH_2$—$CF_3$, —O—$C(CH_3)_2CF_3$, —O—$C(CF_3)_3$, and the like.

As used herein, unless otherwise noted, the term "$C_{X-Y}$cycloalkyl", wherein X and Y are integers, shall mean any stable X- to Y-membered monocyclic, bicyclic, polycyclic, bridged or spiro-cyclic saturated ring system, preferably a monocyclic, bicyclic, bridged or spiro-cyclic saturated ring system. For example, the term "$C_{3-7}$cycloalkyl" includes, but is not limited to cyclopropyl, cyclobutyl, cyclopentyl, cyclohexyl, cycloheptyl, bicyclo[2.2.1]hept-2-yl, and the like.

As used herein, unless otherwise noted, the term "heteroaryl" shall denote any five or six membered monocyclic aromatic ring structure containing at least one heteroatom selected from the group consisting of O, N and S, optionally containing one to three additional heteroatoms independently selected from the group consisting of O, N and S; or nine or ten membered bicyclic aromatic ring structure containing at least one heteroatom selected from the group consisting of O, N and S, optionally containing one to four additional heteroatoms independently selected from the group consisting of O, N and S. The heteroaryl may be bound through any ring atom which results in a stable structure. Suitable examples include, but are not limited to, furanyl, thienyl, furazanyl, oxazolyl, imidazolyl, pyrrolyl, pyrazolyl, thiazolyl, isoxazolyl, isothiazolyl, triazolyl, thiadiazolyl, oxadiazolyl, pyrazyl, pyridyl, pyridazinyl, pyrimidinyl, pyrazinyl, triazinyl, indolyl, indolizinyl, isoindolinyl, indazolyl, benzofuranyl, benzothienyl, benzimidazolyl, benzthiazolyl, purinyl, quinolizinyl, quinolinyl, isoquinolinyl, isothiazolyl, cinnolinyl, phthalazinyl, quinazolinyl, quinoxalinyl, naphthyridinyl, pteridinyl, imidazo[1,2-a]pyridin-7-yl, [1,2,4]triazolo[4,3-a]pyridin-7-yl, and the like.

As used herein, unless otherwise noted, the term "5 to 6 membered heteroaryl" shall denote any five or six membered monocyclic aromatic ring structure containing at least one heteroatom selected from the group consisting of O, N and S, optionally containing one to three additional heteroatoms independently selected from the group consisting of O, N and S. Suitably examples include, but are not limited to furyl, thienyl, pyrrolyl, oxazolyl, thiazolyl, imidazolyl, pyrazolyl, isoxazolyl, isothiazolyl, oxadiazolyl, triazolyl, thidiazolyl, tetrazolyl, pyranyl, pyridinyl, pyridazinyl, pyrimidinyl, pyrazinyl, triazinyl, dioxinyl, oxazinyl, isoxazinyl, oxathiazinyl, oxadiazinyl, and the like In some embodiments of the present invention, the 5 to 6 membered heteroaryl is a 5 membered heteroaryl. In some embodiments of the present invention, the 5 to 6 membered heteroaryl is a 6 membered heteroaryl.

In some embodiments of the present invention, the 5 to 6 membered heteroaryl is a 5 to 6 membered nitrogen containing heteroaryl. In some embodiments of the present invention, the 5 to 6 membered heteroaryl is a 5 membered nitrogen containing heteroaryl. In some embodiments of the present invention, the 5 to 6 membered heteroaryl is a 6 membered nitrogen containing heteroaryl.

The term "5 to 6 membered nitrogen containing heteroaryl" shall denote any five or six membered monocyclic aromatic ring structure containing at least one N atom, optionally containing one to three additional heteroatoms independently selected from the group consisting of O, N and S. Suitably examples include, but are not limited to pyrrolyl, oxazolyl, thiazolyl, imidazolyl, pyrazolyl, isoxazolyl, isothiazolyl, oxadiazolyl, triazolyl, thidiazolyl, tetrazolyl, pyridinyl, pyridazinyl, pyrimidinyl, pyrazinyl, triazinyl, oxazinyl, isoxazinyl, oxathiazinyl, oxadiazinyl, and the like.

The term "5 membered heteroaryl" shall denote any five membered monocyclic aromatic ring structure containing at least one heteroatom selected from the group consisting of O, N and S, optionally containing one to three additional heteroatoms independently selected from the group consisting of O, N and S; whereas the term and "5 membered nitrogen containing heteroaryl" shall denote any five membered monocyclic aromatic ring structure containing at least N atom, optionally containing one to three additional heteroatoms independently selected from the group consisting of O, N and S.

The term "6 membered heteroaryl" shall denote any six membered monocyclic aromatic ring structure containing at least one heteroatom selected from the group consisting of O, N and S, optionally containing one to three additional heteroatoms independently selected from the group consisting of O, N and S; whereas the term and "6 membered nitrogen containing heteroaryl" shall denote any six membered monocyclic aromatic ring structure containing at least N atom, optionally containing one to three additional heteroatoms independently selected from the group consisting of O, N and S.

Unless otherwise noted, any heteroaryl (regardless of the number of ring atoms, the number and identity of ring heteroatoms, etc.) may be bound through any ring atom which results in a stable structure.

As used herein, unless otherwise noted, the term "9 to 10 membered heteroaryl" shall denote any nine or ten membered bicyclic aromatic ring structure containing at least one heteroatom selected from the group consisting of O, N and S, optionally containing one to four additional heteroatoms independently selected from the group consisting of O, N and S. The heteroaryl may be bound through any ring atom which results in a stable structure. Suitable examples include, but are not limited to, indolyl, indolizinyl, isoindolinyl, indazolyl, benzofuranyl, benzothienyl, benzimidazolyl, benzthiazolyl, purinyl, quinolizinyl, quinolinyl, isoquinolinyl, isothiazolyl, cinnolinyl, phthalazinyl, quinazolinyl, quinoxalinyl, naphthyridinyl, pteridinyl, imidazo[1,2-a]pyridin-7-yl, [1,2,4]triazolo[4,3-a]pyridin-7-yl, and the like.

In some embodiments of the present invention, the 9 to 10 membered heteroaryl is a 9 membered heteroaryl. In some embodiments of the present invention, the 9 to 10 membered heteroaryl is a 10 membered heteroaryl.

In some embodiments of the present invention, the 9 to 10 membered heteroaryl is a 9 to 10 membered nitrogen containing heteroaryl. In some embodiments of the present invention, the 9 to 10 membered heteroaryl is a 9 membered nitrogen containing heteroaryl. In some embodiments of the present invention, the 9 to 10 membered heteroaryl is a 10 membered nitrogen containing heteroaryl.

The term "9 to 10 membered nitrogen containing heteroaryl" shall denote any nine or ten membered bicyclic aromatic ring structure containing at least one N atom, optionally containing one to four additional heteroatoms independently selected from the group consisting of O, N and S. The heteroaryl may be bound through any ring atom which results in a stable structure. Suitable examples include, but are not limited to, indolyl, indolizinyl, isoindolinyl, indazolyl, benzimidazolyl, benzthiazolyl, purinyl, quinolizinyl, quinolinyl, isoquinolinyl, isothiazolyl, cinnolinyl, phthalazinyl, quinazolinyl, quinoxalinyl, naphthyridinyl, pteridinyl, imidazo[1,2-a]pyridin-7-yl, [1,2,4]triazolo[4,3-a]pyridin-7-yl, and the like.

The term "9 membered heteroaryl" shall denote any nine membered bicyclic aromatic ring structure containing at least one heteroatom selected from the group consisting of O, N and S, optionally containing one to three additional heteroatoms independently selected from the group consisting of O, N and S; whereas the term and "9 membered nitrogen containing heteroaryl" shall denote any nine membered bicyclic aromatic ring structure containing at least N atom, optionally containing one to three additional heteroatoms independently selected from the group consisting of O, N and S.

The term "10 membered heteroaryl" shall denote any ten membered bicyclic aromatic ring structure containing at least one heteroatom selected from the group consisting of O, N and S, optionally containing one to three additional heteroatoms independently selected from the group consisting of O, N and S; whereas the term and "10 membered nitrogen containing heteroaryl" shall denote any ten membered bicyclic aromatic ring structure containing at least N atom, optionally containing one to three additional heteroatoms independently selected from the group consisting of O, N and S.

Unless otherwise noted, any heteroaryl (regardless of the number of ring atoms, the number and identity of ring heteroatoms, etc.) may be bound through any ring atom which results in a stable structure.

When a particular group is "substituted" (e.g. $C_{X-Y}$alkyl, heteroaryl, etc.), that group may have one or more substituents, preferably from one to five substituents, more preferably from one to three substituents, most preferably from one to two substituents, independently selected from the list of substituents.

With reference to substituents, the term "independently" means that when more than one of such substituents is possible, such substituents may be the same or different from each other.

Under standard nomenclature used throughout this disclosure, the terminal portion of the designated side chain is described first, followed by the adjacent functionality toward the point of attachment. Thus, for example, a "phenyl-($C_1$-$C_6$alkylene)-amino-carbonyl-($C_1$-$C_6$alkylene)-" substituent refers to a group of the formula

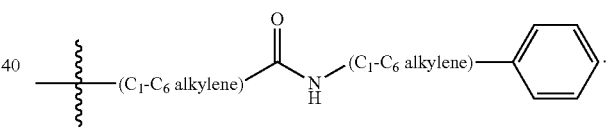

Abbreviations used in the specification, particularly the Schemes and Examples, are as listed in the Table A, below:

TABLE A

| | Abbreviations | |
|---|---|---|
| Ac | = | Acetyl (i.e. —C(O)CH$_3$) |
| AcOH | = | Acetic Acid |
| ACN or MeCN | = | Acetonitrile |
| aq. | = | Aqueous |
| BF$_3$•Et$_2$O | = | Boron trifluoride diethyl etherate |
| BINAP | = | (2,2'-Bis(diphenylphosphino)-1,1'-binaphthyl) |
| Boc or BOC | = | tert-Butoxyloxycarbonyl (i.e. —C(O)—O—C(CH$_3$)$_3$) |
| B(O-iPr)$_3$ | = | Tri(isopropyl) Borate |
| BSA | = | Bovine Serum Albumin |
| CHAPS | = | 3-[(3-Cholamidopropyl)dimethylammonio]-1-propanesulfonate |
| dba | = | dibenzylideneacetone |
| DCE | = | 1,2-Dichloroethane |
| DCM | = | Dichloromethane |
| DEA | = | Diethanolamine |
| DIEA or DIPEA | = | Diisopropylethyl Amine |
| DME | = | Diabetic Macular Edema |
| DMF | = | N,N-Dimethylformamide |
| DMSO | = | Dimethylsulfoxide |
| dppf | = | 1,1'-Bis(diphenylphosphino)ferrocene |

TABLE A-continued

| Abbreviations | | |
|---|---|---|
| EA or EtOAc | = | Ethyl Acetate |
| EDCI | = | 1-Ethyl-3-(3-dimethylaminopropyl) carbodiimide |
| Ee | = | Enantiomeric Excess |
| ER | = | End Point Read (assay) |
| equiv. | = | Equivalents |
| ES or ESI | = | Electrospray ionization |
| Et | = | Ethyl |
| EtOH | = | Ethanol |
| Et$_2$O | = | Diethyl Ether |
| FA | = | Formic Acid |
| FXIa | = | Factor XIa |
| Grubbs 2$^{nd}$ generation catalyst | = | (1,3-Bis(2,4,6-trimethylphenyl)-2-imidazolidinylidene)dichloro(phenylmethylene)(tricyclohexylphosphine)ruthenium |
| HAE | = | Hereditary Angioedema |
| HATU | = | (1-[Bis(dimethylamino)methylene]-1H-1,2,3-triazolo[4,5-b]pyridinium 3-oxide hexafluorophosphate |
| Hex | = | Hexanes |
| HOAc | = | Acetic Acid |
| HPLC | = | High Performance Liquid Chromatography |
| IPA | = | Isopropyl Alcohol |
| KIN | = | Kinetic Read (assay) |
| KOAc | = | Potassium Acetate |
| KOt-Bu | = | Potassium tert-Butoxide |
| LC-MS or LC/MS | = | Liquid chromatography-mass spectrometry |
| Me | = | Methyl |
| MeOH | = | Methanol |
| 2-Me-THF | = | 2-Methyl-tetrahydrofuran |
| MOM | = | Methoxy methyl |
| Ms or mesyl | = | Methylsulfonyl (i.e. —SO$_2$—CH$_3$) |
| NaOt-Bu | = | Sodium tert-Butoxide |
| NBS | = | N-Bromosuccinimide |
| n-BuLi | = | n-Butyl Lithium |
| NCS | = | N-Chlorosuccinimide |
| NH$_4$OAc | = | Ammonium Acetate |
| NIS | = | N-Iodosuccinimide |
| NMR | = | Nuclear Magnetic Resonance |
| OMs or mesylate | = | Methanesulfonate (i.e. —O—SO$_2$—CH$_3$) |
| OTf or tritiate | = | Trifluoromethanesulfonyl (i.e. —O—SO═—CF$_3$) |
| OTs or tosylate | = | p-Toluenesulfonate (i.e. —O—SO$_2$—(p-methylphenyl)) |
| Pd(dppf)Cl$_2$ or PdCl$_2$(dppf) | = | [1,1'-Bis(diphenylphosphino)ferrocene] Palladium (II) Dichloride |
| PdCl$_2$(PPh$_3$)$_2$ or Pd(PPh$_3$)$_2$Cl$_2$ | = | Bis(triphenylphosphine)palladium (II) Dichloride |
| Pd$_2$(dba)$_3$ | = | Tris(dibenzylideneacetone)dipalladium(0) |
| Pd(PPh$_3$)$_4$ | = | Tetrakis(triphenylphosphine)palladium(0) |
| PE | = | Petroleum ether |
| Ph | = | Phenyl |
| PK | = | Plasma Kallikrein |
| PPh$_3$ | = | Triphenylphosphine |
| PyBOP | = | (Benzotriazol-1-yloxytripyrrolidinophosphonium hexafluorophosphate) |
| RFU | = | Relative Fluorescence Unit |
| sat. | = | Saturated |
| Selectfluor | = | 1-Chloromethyl-4-fluoro-1,4-diazoniabicyclo[2.2.2]octane bis |
| SFC (purification) | = | Supercritical Fluid Chromatography (purification) |
| TBAF | = | Tetra-n-butylammonium fluoride |
| t-BuOK or KOt-Bu | = | Potassium tert-Butoxide |
| TEA or Et$_3$N | = | Triethylamine |
| Tf or triflyl | = | Trifluoromethylsulfonyl (i.e. —SO$_2$—CF$_3$) |
| TFA | = | Trifluoroacetic acid |
| TFAA | = | Trifluoroacetic anhydride |
| THF | = | Tetrahydrofuran |
| THP | = | Tetrahydropyranyl |
| TLC | = | Thin Layer Chromatography |
| TMS | = | Trimethysilyl |
| TMSN$_3$ | = | Trimethylsilyl azide |
| Tris (buffer) | = | 2-Amino-2-(hydroxymethyl)-1,3-propanediol |
| Ts or tosyl | = | —SO$_2$—(p-methylphenyl) |
| TsCl | = | Tosyl Chloride |

As used herein, the "*" symbol or notation shall denote the presence of a stereogenic center.

Where the compounds according to this invention have at least one chiral center, they may accordingly exist as enantiomers. Where the compounds possess two or more chiral centers, they may additionally exist as diastereomers. It is to be understood that all such isomers and mixtures thereof are encompassed within the scope of the present invention. It is further understood that atropisomers (a specific type of stereoisomer resulting from steric or other hinderances to rotation) are also encompassed within the scope of the present invention.

Preferably, wherein the compound is present as an enantiomer, the enantiomer is present at an enantiomeric excess of greater than or equal to about 80%, more preferably, at an enantiomeric excess of greater than or equal to about 90%, more preferably still, at an enantiomeric excess of greater than or equal to about 95%, more preferably still, at an enantiomeric excess of greater than or equal to about 98%, most preferably, at an enantiomeric excess of greater than or equal to about 99%. Similarly, wherein the compound is present as a diastereomer or stereoisomer, the diastereomer or stereoisomer is present at a diastereomeric or stereoisomeric excess of greater than or equal to about 80%, more preferably, at a diastereomeric or stereoisomeric excess of greater than or equal to about 90%, more preferably still, at a diastereomeric or stereoisomeric excess of greater than or equal to about 95%, more preferably still, at a diastereomeric or stereoisomeric excess of greater than or equal to about 98%, most preferably, at a diastereomeric or stereoisomeric excess of greater than or equal to about 99%.

In some embodiments, the present invention is directed to compounds of formula (I) in an enantiomeric excess of one of the R- or S-enantiomers (at the $R^3$ stereocenter denoted with the "*"). In some embodiments of the present invention, the compound of formula (I) is present in an enantiomeric excess of one of the R- or S-enantiomers (at the $R^3$ stereocenter denoted with the "*") of about 55%, about 60%, about 65%, about 70%, about 75%, about 80%, about 85%, about 90%, about 91%, about 92%, about 93%, about 94%, about 95%, about 96%, about 97%, about 98% or about 99%. Preferably the compound of formula (I) is present in an enantiomeric excess of one of the R- or S-enantiomers (at the $R^3$ stereocenter denoted with the "*") of greater than or equal to about 80%, preferably greater than or equal to about 90%, more preferably greater than or equal to about 93%, more preferably greater than or equal to about 95%, more preferably greater than or equal to about 97%, more preferably greater than or equal to about 98%, more preferably greater than or equal to about 99%.

In some embodiments, the present invention is directed to compounds of formula (I) in a diastereomeric or stereoisomeric excess of one of the possible diastereomers or stereoisomers. In some embodiments of the present invention, the compound of formula (I) is present in a diastereomeric or stereoisomeric excess of one of the possible diastereomers or stereoisomers, of about 55%, about 60%, about 65%, about 70%, about 75%, about 80%, about 85%, about 90%, about 91%, about 92%, about 93%, about 94%, about 95%, about 96%, about 97%, about 98% or about 99%. Preferably, the compound of formula (I) is present in a diastereomeric or stereoisomeric excess of one of the possible diastereomers or stereoisomers of greater than or equal to about 80%, preferably greater than or equal to about 90%, more preferably greater than or equal to about 93%, more preferably greater than or equal to about 95%, more preferably greater than or equal to about 97%, more preferably greater than or equal to about 98%, more preferably greater than or equal to about 99%.

Furthermore, some of the crystalline forms for the compounds of the present invention may exist as polymorphs and as such are intended to be included in the present invention. In addition, some of the compounds of the present invention may form solvates with water (i.e., hydrates) or common organic solvents, and such solvates are also intended to be encompassed within the scope of this invention.

As used herein, unless otherwise noted, the term "isotopologues" shall mean molecules that differ only in their isotopic composition. More particularly, an isotopologue of a molecule differs from the parent molecule in that it contains at least one atom which is an isotope (i.e. has a different number of neutrons from its parent atom).

For example, isotopologues of water include, but are not limited to, "light water" (HOH or $H_2O$), "semi-heavy water" with the deuterium isotope in equal proportion to protium (HDO or $^1H^2HO$), "heavy water" with two deuterium isotopes of hydrogen per molecule ($d_2O$ or $^2H_2O$), "super-heavy water" or tritiated water ($T_2O$ or $^3H_2O$), where the hydrogen atoms are replaced with tritium ($^3H$) isotopes, two heavy-oxygen water isotopologues ($H_2^{18}O$ and $H_2^{17}O$) and isotopologues where the hydrogen and oxygen atoms may each independently be replaced by isotopes, for example the doubly labeled water isotopologue $d_2^{18}O$.

It is intended that within the scope of the present invention, any one or more element(s), in particular when mentioned in relation to a compound of formula (I), shall comprise all isotopes and isotopic mixtures of said element(s), either naturally occurring or synthetically produced, either with natural abundance or in an isotopically enriched form. For example, a reference to hydrogen includes within its scope $^1H$, $^2H$ (D), and $^3H$ (T). Similarly, references to carbon and oxygen include within their scope respectively $^{12}C$, $^{13}C$ and $^{14}C$ and $^{16}O$ and $^{18}O$. The isotopes may be radioactive or non-radioactive.

Radiolabelled compounds of formula (I) may comprise one or more radioactive isotope(s) selected from the group of $^3H$, $^{11}C$, $^{18}F$, $^{122}I$, $^{123}I$, $^{125}I$, $^{131}I$, $^{75}Br$, $^{76}Br$, $^{77}Br$ and $^{82}Br$. Preferably, the radioactive isotope is selected from the group of $^3H$ $^{11}C$ and $^{18}F$.

As used herein, unless otherwise noted, the term "isotopomer" shall mean isomers with isotopic atoms, having the same number of each isotope of each element but differing in their position. Isotopomers include both constitutional isomers and stereoisomers solely based on isotopic location. For example, $CH_3CHDCH_3$ and $CH_3CH_2CH_2D$ are a pair of constitutional isotopomers of n-propane, whereas (R)-$CH_3CHDOH$ and (S)-$CH_3CHDOH$ or (Z)-$CH_3CH=CHD$ and (E)-$CH_3CH=CHD$ are examples of isotopic stereoisomers of ethanol and n-propene, respectively.

It is further intended that the present invention includes the compounds described herein, including all isomers thereof (including, but not limited to stereoisomers, enantiomers, diastereomers, tautomers, isotopologues, and the like).

As used herein, unless otherwise noted, the term "isolated form" shall mean that the compound is present in a form which is separate from any solid mixture with another compound(s), solvent system or biological environment. In an embodiment of the present invention, the compound of formula (I) is present in an isolated form.

As used herein, unless otherwise noted, the term "substantially pure form" shall mean that the mole percent of impurities in the isolated compound is less than about 5 mole percent, preferably less than about 2 mole percent, more preferably, less than about 0.5 mole percent, most preferably, less than about 0.1 mole percent. In an embodiment of the present invention, the compound of formula (I) is present as a substantially pure form.

As used herein, unless otherwise noted, the term "substantially free of a corresponding salt form(s)" when used to described the compound of formula (I) shall mean that mole percent of the corresponding salt form(s) in the isolated base of formula (I) is less than about 5 mole percent, preferably less than about 2 mole percent, more preferably, less than about 0.5 mole percent, most preferably less than about 0.1 mole percent. In an embodiment of the present invention, the compound of formula (I) is present in a form which is substantially free of corresponding salt form(s).

For use in medicine, the salts of the compounds of this invention refer to non-toxic "pharmaceutically acceptable salts". Other salts may, however, be useful in the preparation of compounds according to this invention or of their pharmaceutically acceptable salts. Suitable pharmaceutically acceptable salts of the compounds include acid addition salts which may, for example, be formed by mixing a solution of the compound with a solution of a pharmaceutically acceptable acid such as hydrochloric acid, sulfuric acid, fumaric acid, maleic acid, succinic acid, acetic acid, benzoic acid, citric acid, tartaric acid, carbonic acid or phosphoric acid. Furthermore, where the compounds of the invention carry an acidic moiety, suitable pharmaceutically acceptable salts thereof may include alkali metal salts, e.g., sodium or potassium salts; alkaline earth metal salts, e.g., calcium or magnesium salts; and salts formed with suitable organic ligands, e.g., quaternary ammonium salts. Thus, representative pharmaceutically acceptable salts include, but are not limited to, the following: acetate, benzenesulfonate, benzoate, bicarbonate, bisulfate, bitartrate, borate, bromide, calcium edetate, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isothionate, lactate, lactobionate, laurate, malate, maleate, mandelate, mesylate, methylbromide, methylnitrate, methylsulfate, mucate, napsylate, nitrate, N-methylglucamine ammonium salt, oleate, pamoate (embonate), palmitate, pantothenate, phosphate/diphosphate, polygalacturonate, salicylate, stearate, sulfate, subacetate, succinate, tannate, tartrate, teoclate, tosylate, triethiodide and valerate.

Representative acids which may be used in the preparation of pharmaceutically acceptable salts include, but are not limited to, the following: acids including acetic acid, 2,2-dichloroacetic acid, acylated amino acids, adipic acid, alginic acid, ascorbic acid, L-aspartic acid, benzenesulfonic acid, benzoic acid, 4-acetamidobenzoic acid, (+)-camphoric acid, camphorsulfonic acid, (+)-(1S)-camphor-10-sulfonic acid, capric acid, caproic acid, caprylic acid, cinnamic acid, citric acid, cyclamic acid, dodecylsulfuric acid, ethane-1,2-disulfonic acid, ethanesulfonic acid, 2-hydroxy-ethanesulfonic acid, formic acid, fumaric acid, galactaric acid, gentisic acid, glucoheptonic acid, D-gluconic acid, D-glucoronic acid, L-glutamic acid, α-oxo-glutaric acid, glycolic acid, hippuric acid, hydrobromic acid, hydrochloric acid, (+)-L-lactic acid, (±)-DL-lactic acid, lactobionic acid, maleic acid, (±)-L-malic acid, malonic acid, (±)-DL-mandelic acid, methanesulfonic acid, naphthalene-2-sulfonic acid, naphthalene-1,5-disulfonic acid, 1-hydroxy-2-naphthoic acid, nicotinic acid, nitric acid, oleic acid, orotic acid, oxalic acid, palmitic acid, pamoic acid, phosphoric acid, L-pyroglutamic acid, salicylic acid, 4-amino-salicylic acid, sebacic acid, stearic acid, succinic acid, sulfuric acid, tannic acid, (+)-L-tartaric acid, thiocyanic acid, p-toluenesulfonic acid and undecylenic acid.

Representative bases which may be used in the preparation of pharmaceutically acceptable salts include, but are not limited to, the following: bases including ammonia, L-arginine, benethamine, benzathine, calcium hydroxide, choline, deanol, diethanolamine, diethylamine, 2-(diethylamino)-ethanol, ethanolamine, ethylenediamine, N-methyl-glucamine, hydrabamine, 1H-imidazole, L-lysine, magnesium hydroxide, 4-(2-hydroxyethyl)-morpholine, piperazine, potassium hydroxide, 1-(2-hydroxyethyl)-pyrrolidine, secondary amine, sodium hydroxide, triethanolamine, tromethamine and zinc hydroxide.

The present invention includes within its scope prodrugs of the compounds of this invention. In general, such prodrugs will be functional derivatives of the compounds which are readily convertible in vivo into the required compound. Thus, in the methods of treatment of the present invention, the term "administering" shall encompass the treatment of the various disorders described with the compound specifically disclosed or with a compound which may not be specifically disclosed, but which converts to the specified compound in vivo after administration to the patient. Conventional procedures for the selection and preparation of suitable prodrug derivatives are described, for example, in "Design of Prodrugs", ed. H. Bundgaard, Elsevier, 1985.

The term "subject" as used herein, refers to an animal, preferably a mammal, most preferably a human, who has been the object of treatment, observation or experiment. Preferably, the subject has experienced and/or exhibited at least one symptom of the disease or disorder to be treated and/or prevented.

The term "therapeutically effective amount" as used herein, means that amount of active compound or pharmaceutical agent that elicits the biological or medicinal response in a tissue system, animal or human that is being sought by a researcher, veterinarian, medical doctor or other clinician, which includes alleviation of the symptoms of the disease or disorder being treated.

As used herein, the term "composition" is intended to encompass a product comprising the specified ingredients in the specified amounts, as well as any product which results, directly or indirectly, from combinations of the specified ingredients in the specified amounts.

As used herein, unless otherwise noted, the terms "treating", "treatment" and the like, shall include the management and care of a subject or patient, preferably a mammal, more preferably a human, for the purpose of combating a disease, condition, or disorder and includes the administration of a compound of the present invention to prevent the onset of the symptoms or complications, alleviate the symptoms or complications, slow the progression of the disease or disorder, or eliminate the disease, condition, or disorder. The terms "treating" or "treatment" further include: (a) inhibiting the disease-state, i.e., arresting its development, and/or (b) relieving the disease-state, i.e., causing regression of the disease state.

As used herein, "prevention" covers the preventive treatment of a subclinical disease-state in a mammal, particularly in a human, aimed at reducing the probability of the occurrence of a clinical disease-state. Patients are selected for preventative therapy based on factors that are known to increase risk of suffering a clinical disease state compared to the general population.

As used herein, "prophylaxis" is the protective treatment of a disease state to reduce and/or minimize the risk and/or reduction in the risk of recurrence of a disease state by administering to a patient a therapeutically effective amount of at least one of the compounds of the present invention or a stereoisomer, isotopologue, or a pharmaceutically acceptable salt, thereof. Patients may be selected for prophylaxis therapy based on factors that are known to increase risk of suffering a clinical disease state compared to the general population. For prophylaxis treatment, conditions of the clinical disease state may or may not be presented yet. "Prophylaxis" treatment can be divided into (a) primary prophylaxis and (b) secondary prophylaxis. Primary prophylaxis is defined as treatment to reduce or minimize the risk of a disease state in a patient that has not yet presented with a clinical disease state, whereas secondary prophylaxis is defined as minimizing or reducing the risk of a recurrence or second occurrence of the same or similar clinical disease state.

As used herein, "risk reduction" covers therapies that lower the incidence of development of a clinical disease state. As such, primary and secondary prevention therapies are examples of risk reduction.

As used herein, the terms "combination" and "pharmaceutical combination" refer to either: 1) a fixed dose combination in one dosage unit form, or 2) a non-fixed dose combination, optionally packaged together for combined administration.

Examples

The following Examples are set forth to aid in the understanding of the invention and are not intended and should not be construed to limit in any way the invention set forth in the claims which follow thereafter.

Unless otherwise indicated in the examples, all temperature is expressed in Centigrade (° C.). All reactions were conducted under an inert atmosphere at ambient temperature unless otherwise noted. Unless otherwise specified, reaction solutions were stirred at room temperature under a $N_{2(g)}$ or $Ar_{(g)}$ atmosphere. Reagents employed without synthetic details are commercially available or made according to known methods, for example according to literature procedures. When solutions were "concentrated to dryness", they were concentrated using a rotary evaporator under reduced pressure, when solutions were dried, they were typically dried over a drying agent such as $MgSO_4$ or $Na_2SO_4$. Where a synthesis product is listed as having been isolated as a residue, it will be understood by those skilled in the art that the term "residue" does not limit the physical state in which the product was isolated and may include, for example, a solid, an oil, a foam, a gum, a syrup, and the like.

In obtaining the compounds described in the examples below and the corresponding analytical data, the following experimental and analytical protocols were followed unless otherwise indicated.

LC-MS: Unless otherwise indicated, the analytical LC-MS system used consisted of a Shimadzu LCMS-2020 with electrospray ionization (ESI) in positive ion detection mode with 20ADXR pump, SIL-20ACXR autosampler, CTO-20AC column oven, M20A PDA Detector and LCMS 2020 MS detector. The column was a HALO a C18 30*5.0 mm, 2.7 μm. The mobile phase A was water containing 0.05% TFA and mobile phase B was acetonitrile containing 0.05% TFA. The gradient was from 5% mobile phase B to 100% (95%) in 2.0 min, hold 0.7 min, then revert to 5% mobile phase B over 0.05 min and maintain for 0.25 min. The Column Oven (CTO-20AC) was operated at a 40.0° C. The flow rate was 1.5 mL/min, and the injection volume was 1 μl. PDA (SPD-M20A) detection was in the range 190-400 nm. The MS detector, which was configured with electrospray ionization as ionizable source; Acquisition mode: Scan; Nebulizing Gas Flow: 1.5 L/min; Drying Gas Flow: 15 L/min; Detector Voltage: Tuning Voltage±0.2 kv; DL Temperature: 250° C.; Heat Block Temperature: 250° C.; Scan Range: 90.00-900.00 m/z. ELSD (Alltech 3300) detector Parameters: Drift Tube Temperature: 60±5° C.; N2 Flow-Rate: 1.8±0.2 L/min. Mobile phase gradients were optimized for the individual compounds. Calculated mass corresponds to the exact mass.

Preparative HPLC: Unless otherwise noted, preparative HPLC purifications were performed with Waters Auto purification system (2545-2767) with a 2489 UV detector. The column was selected from one of the following: Waters C18, 19×150 mm, 5 μm; XBridge Prep OBD C18 Column, 30×150 mm 5 μm; XSelect CSH Prep C18 OBD Column, 5 μm, 19*150 mm; XBridge Shield RP18 OBD Column, 30×150 mm, 5 μm; Xselect CSH Fluoro Phenyl, 30×150 mm, 5 μm; or YMC-Actus Triart C18, 30×150 mm, 5 μm. The mobile phases consisted of mixtures of acetonitrile (5-95%) in water containing 0.1% FA or 10 mmol/L $NH_4HCO_3$. Flow rates were maintained at 25 mL/min, the injection volume was 1200 μL, and the UV detector used two channels 254 nm and 220 nm. Mobile phase gradients were optimized for the individual compounds.

Chiral chromatography: Chiral analytical chromatography was performed on one of Chiralpak AS, AD, Chiralcel OD, OJ Chiralpak IA,IB,IC,ID,IE,IF,IG,IH columns (Daicel Chemical Industries, Ltd.) (R,R)-Whelk-O1, (S,S)-Whelk-O1 columns (Regis technologies, Inc.) CHIRAL Cellulose-SB, SC, SA columns (YMC Co., Ltd.) as noted, at different column size (50×4.6 mm, 100×4.6 mm, 150×4.6 mm, 250×4.6 mm, 50×3.0 mm, 100×3.0 mm), with percentage of either ethanol in hexane (% EtOH/Hex) or isopropanol in hexane (% IPA/Hex) as isocratic solvent systems, or using supercritical fluid (SFC) conditions.

Normal phase flash chromatography: Unless otherwise noted, normal phase flash column chromatography (FCC) was performed on silica gel with pre-packaged silica gel columns (such as RediSep©), using ethyl acetate (EtOAc)/hexanes, ethyl acetate (EtOAc)/Petroleum ether (b.p. 60-90° C.), $CH_2Cl_2$/MeOH, or $CH_2Cl_2$/10% 2N $NH_3$ in MeOH, as eluent.

$^1$H NMR: Unless otherwise noted, $^1$H NMR spectra were acquired using 400 MHz spectrometers (or 300 MHz spectrometers) in DMSO-$d_6$ solutions. The nuclear magnetic resonance (NMR) spectral characteristics refer to chemical shifts (δ) are expressed in parts per million (ppm). Tetramethylsilane (TMS) was used as internal reference in DMSO-$d_6$ solutions, and residual $CH_3OH$ peak or TMS was used as internal reference in $CD_3OD$ solutions. Coupling constants (J) are reported in hertz (Hz). The nature of the shifts as to multiplicity is reported as s (singlet), d (doublet), t (triplet), q (quartet), dd (double doublet), dt (double triplet), m (multiplet), br (broad).

Synthesis Examples: Intermediates

Intermediate 1: (3S,9S)-7-(2-Amino-5-chlorophenyl)-5-oxo-2,3,5,8,9,9a-hexahydro-1H-pyrrolo[1,2-a]azepine-3-carboxylic acid

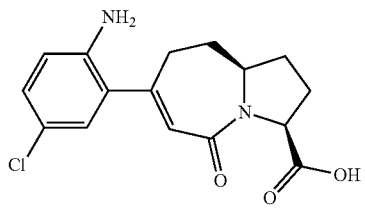 [SMILES: Nc1ccc(Cl)cc1C1=CC(=O)N2[C@@H](CC1)CC[C@H]2C(=O)O]

Step 1: (S)-2-((Tert-butoxycarbonyl)amino)-5-oxonon-8-enoate

To a solution of Mg (6.5 g, 246.95 mmol, 6.0 equiv.) in THF (300 mL) was added 4-bromo-1-butene (6.7 g, 49.25 mmol) and the mixture was stirred at room temperature for 10 min. An additional portion of 4-bromo-1-butene was then added (10.0 g, 74.07 mmol) and the resulting mixture was stirred for an additional 2 h. The resulting solution was added to a solution of 1-(tert-butyl) 2-methyl (R)-5-oxopyrrolidine-1,2-dicarboxylate (10.0 g, 41.11 mmol, 1.0 equiv.) in THF (300 mL) at −78° C. The mixture was maintained under nitrogen with stirring at −78° C. for 4 h. The reaction was quenched with $NH_4Cl$ solution (150 mL), then extracted with ethyl acetate (3×400 mL). The combined extracts were washed with water, dried over $Na_2SO_4$, filtered and purified by silica gel chromatography (0-30% EA/PE) to yield methyl (S)-2-((tert-butoxycarbonyl)amino)-5-oxonon-8-enoate as a yellow oil. LC/MS: mass calculated for $C_{15}H_{25}NO_5$: 299.17, measured: 322.10 [M+Na]$^+$.

Step 2: Methyl (2S)-5-(but-3-en-1-yl)pyrrolidine-2-carboxylate

To a solution of methyl (S)-2-((tert-butoxycarbonyl)amino)-5-oxonon-8-enoate (8.0 g, 26.72 mmol, 1.0 equiv.) in DCM (100 mL) at −78° C. were added boron trifluoride etherate (22.8 g, 160.65 mmol, 6.0 equiv.) and triphenylsilane (20.9 g, 80.26 mmol, 3.0 equiv.). The mixture was maintained under nitrogen with stirring at −78° C. for 0.5 h, then warmed to room temperature stirred for 2 h. The reaction mixture was cooled to −78° C. and the reaction quenched with $NaHCO_3$ solution (40 mL), then extracted with DCM (3×300 mL). The combined extracts were washed with water, dried over $Na_2SO_4$, filtered and purified by silica gel chromatography (0-10% MeOH/DCM) to yield methyl (2S)-5-(but-3-en-1-yl)pyrrolidine-2-carboxylate as a yellow oil. LC/MS: mass calculated for $C_{10}H_{17}NO_2$: 183.13, measured: 184.10 [M+H]$^+$.

Step 3: Methyl (2S,5S)-1-acryloyl-5-(but-3-en-1-yl)pyrrolidine-2-carboxylate To a solution of methyl (2S)-5-(but-3-en-1-yl)pyrrolidine-2-carboxylate (4.0 g, 21.83 mmol, 1.0 equiv.) in THF (80 mL) at −78° C. were added TEA (11.0 g, 108.71 mmol, 5.0 eq.) and acryloyl chloride (2.0 g, 22.10 mmol, 1.0 equiv.). The mixture was maintained under nitrogen with stirring at −78° C. for 0.5 h, then warmed to room temperature with stirring for 2 h under $N_2$. The reaction was quenched with $NH_4Cl$ solution (40 mL), then extracted with ethyl acetate (3×100 mL). The combined extracts were washed with water, dried over $Na_2SO_4$, filtered and purified by silica gel chromatography (0-50% EA/PE) to yield methyl (2S,5S)-1-acryloyl-5-(but-3-en-1-yl)pyrrolidine-2-carboxylate as a yellow oil. LC/MS: mass calculated $C_{13}H_{19}NO_3$: 237.14, measured: 238.30 [M+H]$^+$.

Step 4: Methyl (3S,9S)-5-oxo-2,3,5,8,9,9a-hexahydro-1H-pyrrolo[1,2-a]azepine-3-carboxylate To a solution of methyl (2S,5S)-1-acryloyl-5-(but-3-en-1-yl)pyrrolidine-2-carboxylate (4.5 g, 18.96 mmol, 1.0 equiv.) in DCM (100 mL) was added Grubbs catalyst 2nd generation (3.2 g, 3.76 mmol, 0.2 equiv.). The mixture was maintained under nitrogen stirred at 50° C. overnight under $N_2$. After cooling to room temperature, the reaction was quenched with water (50 mL), extracted with ethyl acetate (3×200 mL). The combined extracts were washed with water, dried over $Na_2SO_4$, filtered and purified by silica gel chromatography (0-10% MeOH/DCM) to yield methyl (3S,9S)-5-oxo-2,3,5,8,9,9a-hexahydro-1H-pyrrolo[1,2-a]azepine-3-carboxylate as a yellow oil. LC/MS: mass calculated $C_{11}H_{15}NO_3$: 209.11, measured: 210.25 [M+H]$^+$.

Step 5: Methyl (3S,9R)-7-hydroxy-5-oxooctahydro-1H-pyrrolo[1,2-a]azepine-3-carboxylate To a mixture of cuprous chloride (0.3 g, 3.03 mmol, 0.2 equiv.) and BINAP (1.9 g, 3.05 mmol, 0.2 equiv.) in THF (50 mL) was added sodium tert-butoxide (0.29 g, 3.02 mmol, 0.2 equiv.) under $N_2$, and the mixture stirred for 30 min. Bis(pinacolato)diboron (4.7 g, 18.51 mmol, 1.2 eq.) was added and the mixture was stirred for 5 min. To the resulting mixture was then added methyl (3S,9S)-5-oxo-2,3,5,8,9,9a-hexahydro-1H-pyrrolo[1,2-a]azepine-3-carboxylate (3.2 g, 15.29 mmol, 1.0 equiv.) in THF (10 mL), followed by addition of methanol (0.98 g, 30.59 mmol, 2.0 equiv.). The mixture was stirred at room temperature overnight under $N_2$. The mixture was then cooled to 0° C. To the mixture was then added $H_2O_2$ (17.3 g, 152.58 mmol, 10.0 eq) dropwise. The mixture maintained under nitrogen with stirring at room temperature for 3 h under $N_2$. The reaction mixture was quenched with water (50 mL), then extracted with ethyl acetate (3×200 mL). The combined extracts were washed with water, dried over $Na_2SO_4$, filtered and purified by silica gel chromatography (0-10% MeOH/DCM) to yield methyl (3S,9R)-7-hydroxy-5-oxooctahydro-1H-pyrrolo[1,2-a]azepine-3-carboxylate as a yellow oil. LC/MS: mass calculated $C_{11}H_{17}NO_4$: 227.12, measured: 228.10 [M+H]$^+$.

Step 6: Methyl (3S,9R)-5,7-dioxooctahydro-1H-pyrrolo[1,2-a]azepine-3-carboxylate To a solution of methyl (3S,9R)-7-hydroxy-5-oxooctahydro-1H-pyrrolo[1,2-a]azepine-3-carboxylate (1.5 g, 6.60 mmol, 1.0 equiv.) in DCM (150 mL) was added pyridinium chlorochromate (2.8 g, 12.99 mmol, 2.0 equiv.) and the mixture was stirred at room temperature overnight. The reaction was quenched with water (50 mL), then extracted with ethyl acetate (3×100 mL). The combined extracts were washed with water, dried over $Na_2SO_4$, filtered and purified by silica gel chromatography (0-10% MeOH/DCM) to yield methyl (3S,9R)-5,7-dioxooctahydro-1H-pyrrolo[1,2-a]

azepine-3-carboxylate as a yellow solid. LC/MS: mass calculated $C_{11}H_{15}NO_4$: 225.10, measured: 226.10 [M+H]⁺.

Step 7: Methyl (3S,9aR)-5-oxo-7-(((trifluoromethyl)sulfonyl)oxy)-2,3,5,8,9,9a-hexahydro-1H-pyrrolo[1,2-a]azepine-3-carboxylate To a solution of methyl (3S,9aR)-5,7-dioxooctahydro-1H-pyrrolo[1,2-a]azepine-3-carboxylate (1.0 g, 4.74 mmol, 1.0 equiv.) in DCM (30 mL) was added N-phenyl-bis(trifluoromethanesulfonimide) (5.1 g, 14.28 mmol, 3.0 equiv.) followed by addition of triethylamine (1.9 g, 18.78 mmol, 4.0 equiv.). The resulting mixture was stirred at room temperature overnight. The reaction was quenched with water (20 mL), then extracted with ethyl acetate (3×100 mL). The combined extracts were washed with water, dried over $Na_2SO_4$, filtered and purified by silica gel chromatography (0-30% EA/PE) to yield methyl (3S,9R)-5-oxo-7-(((trifluoromethyl)sulfonyl)oxy)-2,3,5,8,9,9a-hexahydro-1H-pyrrolo[1,2-a]azepine-3-carboxylate as yellow oil. LC/MS: mass calculated $C_{12}H_{14}F_3NO_6S$: 357.05, measured: 358.20 [M+H]⁺.

Step 8: Methyl (3S,9aS)-7-(2-amino-5-chlorophenyl)-5-oxo-2,3,5,8,9,9a-hexahydro-1H-pyrrolo[1,2-a]azepine-3-carboxylate To a solution of ethyl methyl To a mixture of methyl (3S,9R)-5-oxo-7-(((trifluoromethyl)sulfonyl)oxy)-2,3,5,8,9,9a-hexahydro-1H-pyrrolo[1,2-a]azepine-3-carboxylate (902 mg, 2.52 mmol, 1.0 equiv.) and $Pd(dppf)Cl_2$ (192 mg, 0.25 mmol, 0.1 equiv.) in 1,4-dioxane (20 mL) and $H_2O$ (2 mL) was added 4-chloro-2-(4,4,5,5-tetramethyl-1,3,2-dioxaborolan-2-yl)aniline (768 mg, 3.03 mmol, 1.2 equiv.), followed by the addition of $K_2CO_3$ (1.0 g, 7.58 mmol, 3.0 equiv.). The resulting mixture was maintained under nitrogen with stirring at 90° C. for 4 h. After cooling to room temperature, the reaction was quenched with water (50 mL). The resulting mixture was extracted with ethyl acetate (3×50 mL). The organic layers were combined, dried over anhydrous sodium sulfate, filtered, and concentrated. The resulting residue was purified by silica gel chromatography (0-10% MeOH/DCM) to yield the methyl (3S,9S)-7-(2-amino-5-chlorophenyl)-5-oxo-2,3,5,8,9,9a-hexahydro-1H-pyrrolo[1,2-a]azepine-3-carboxylate as yellow oil. LC/MS: mass calculated for $C_{17}H_{19}ClN_2O_3$: 334.11, measured: 335.15 [M+H]⁺.

Step 9: (3S,9S)-7-(2-Amino-5-chlorophenyl)-5-oxo-2,3,5,8,9,9a-hexahydro-1H-pyrrolo[1,2-a]azepine-3-carboxylic acid To a solution of methyl (3S,9S)-7-(2-amino-5-chlorophenyl)-5-oxo-2,3,5,8,9,9a-hexahydro-1H-pyrrolo[1,2-a]azepine-3-carboxylate (732 mg, 2.19 mmol, 1.0 equiv.) in THF (10 mL) and $H_2O$ (5 mL) was added lithium hydroxide (262 mg, 10.94 mmol, 5.0 equiv.). The reaction was stirred at room temperature for 2 h. The mixture was adjusted to pH 4, then extracted with ethyl acetate (3×100 mL). The organic layers were combined, dried over anhydrous sodium sulfate, filtered and concentrated to yield the (3S,9S)-7-(2-amino-5-chlorophenyl)-5-oxo-2,3,5,8,9,9a-hexahydro-1H-pyrrolo[1,2-a]azepine-3-carboxylic acid as a yellow oil. LC/MS: mass calculated for $C_{16}H_{17}ClN_2O_3$: 320.09, measured: 321.20 [M+H]⁺.

Intermediate 2: (6-amino-3-chloro-2-fluorophenyl)boronic acid

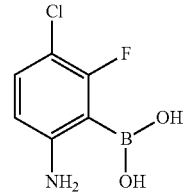 [SMILES: Nc1ccc(Cl)c(F)c1B(O)O]

Step 1: N-(4-Chloro-3-fluorophenyl)-2,2,2-trifluoroacetamide

To a mixture of 4-chloro-3-fluorobenzenamine (20 g, 137.398 mmol, 1.00 equiv) and $Na_2CO_3$ (24.7 g, 233.58 mmol, 1.70 equiv) in $Et_2O$ (400 mL) was added TFAA (34.6 g, 164.88 mmol, 1.20 equiv) dropwise with stirring at −10° C. The mixture was allowed to warm to room temperature overnight, then diluted with hexane (400 mL) and filtered. The filtrate was washed with saturated sodium bicarbonate solution (2×200 mL), brine (2×200 mL), dried over $Na_2SO_4$, and filtered. The filtrate was concentrated to yield N-(4-chloro-3-fluorophenyl)-2,2,2-trifluoroacetamide as white solid.

Step 2: (6-Amino-3-chloro-2-fluorophenyl)boronic acid

To a mixture of N-(4-chloro-3-fluorophenyl)-2,2,2-trifluoroacetamide (30 g, 124.19 mmol, 1.00 equiv) in THF (500 mL) under $N_2$ was added n-BuLi (99 mL, 248.38 mmol, 2.00 equiv, 2.5 M in hexane) dropwise with stirring at −78° C., and the resulting mixture stirred at −78° C. for 15 min. The reaction was then allowed to warm to −50° C., over 1 h. The resulting clear brown solution was cooled to −78° C., and then $B(O-iPr)_3$ (51.3 g, 273.21 mmol, 2.20 equiv) was added dropwise. The reaction was stirred at −78° C. for 10 mm, and then the reaction was allowed to warm to room temperature. The resulting orange suspension was stirred at room temperature for 4 h, then cooled in ice bath and quenched with 1 M HCl (300 mL). The resulting mixture was stirred at room temperature overnight, then extracted with EtOAc (300 mL×3), dried over $Na_2SO_4$, and filtered. The filtrate concentrated. The resulting residue was recrystallized (EtOAc/PE: 1/10) to yield 6-amino-3-chloro-2-fluorophenylboronic acid as white solid.

Intermediate 3: N-(4-(2-Bromoacetyl)-3-fluoropyridin-2-yl)-N-ethylacetamide

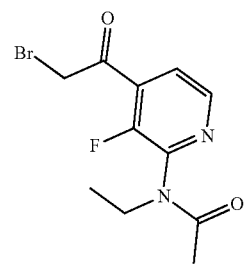 [SMILES: CCN(C(C)=O)c1nccc(C(=O)CBr)c1F]

Step 1: N-(4-(1-ethoxyvinyl)-3-fluoropyridin-2-yl)-N-ethylacetamide

Under an insert atmosphere of nitrogen, a mixture of N-ethyl-N-(3-fluoro-4-iodopyridin-2-yl)acetamide (800 mg, 2.60 mmol, 1.00 equiv), tributyl(1-ethoxyvinyl)stannane (1.2 g, 3.32 mmol, 1.3 equiv), and Pd(PPh$_3$)$_2$Cl$_2$ (182 mg, 0.260 mmol, 0.1 equiv) in 1,4-dioxane (15 mL) was stirred at 90° C. for 2 h, then concentrated. The residue was applied onto a silica gel column (80 g, EtOAc/PE: 1/10) to yield N-(4-(1-ethoxyvinyl)-3-fluoropyridin-2-yl)-N-ethylacetamide as yellow oil.

Step 2: N-(4-(2-bromoacetyl)-3-fluoropyridin-2-yl)-N-ethylacetamide

To a mixture of N-(4-(1-ethoxyvinyl)-3-fluoropyridin-2-yl)-N-ethylacetamide (600 mg, 2.38 mmol, 1.0 equiv) in THF (8 mL) with H$_2$O (4 mL) was added NBS (423 mg, 2.38 mmol, 1.0 equiv) and stirred at room temperature for 30 min. The reaction was quenched with water (50 mL) and extracted with ethyl acetate (100 mL×3). The combined organic layer was washed with brine, dried over Na$_2$SO$_4$, and concentrated to yield N-(4-(2-bromoacetyl)-3-fluoropyridin-2-yl)-N-ethylacetamide as a yellow solid.

Intermediate 4: N-(4-(2-Bromoacetyl)-3-fluoropyridin-2-yl)-N-(2-((tert-butyldimethylsilyl)oxy)-2-methylpropyl)acetamide

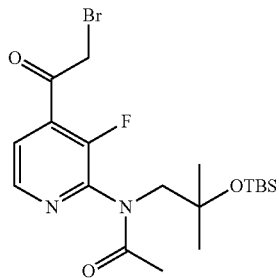 [SMILES: CC(=O)N(CC(C)(C)O[Si](C)(C)C(C)(C)C)c1nccc(C(=O)CBr)c1F]

Step 1: 1-((3-fluoro-4-iodopyridin-2-yl)amino)-2-methylpropan-2-ol

To a solution of 2,3-difluoro-4-iodopyridine (2.0 g, 8.30 mmol, 1.0 equiv.) in DMSO (6 mL) was added 2-amino-2-methyl-1-propanol (4.4 g, 49.80 mmol, 6.0 equiv.). The reaction mixture was stirred at 100° C. for 4 h, then quenched with water. The reaction mixture was extracted with EA. The organic layers were combined, washed with brine, dried and concentrated under vacuum to yield 2-((3-fluoro-4-iodopyridin-2-yl)amino)-2-methylpropan-1-ol as yellow oil. LC/MS: mass calculated for C$_9$H$_{12}$FIN$_2$O: 310.00, measured: 311.00 [M+H]$^+$

Step 2: N-(2-((tert-butyldimethylsilyl)oxy)-2-methylpropyl)-3-fluoro-4-iodopyridin-2-amine To a mixture of 1-((3-fluoro-4-iodopyridin-2-yl)amino)-2-methylpropan-2-ol (2.2 g, 7.06 mmol, 1.0 equiv.) in dichloromethane (21 mL) was added 2,6-dimethylpyridine (1.6 mL, 14.12 mmol, 2.0 equiv) and trifluoromethanesulfonic acid tert-butyldimethylsilyl ester (2.8 g, 10.59 mmol, 1.5 equiv.) at 0° C. The solution was stirred at room temperature for 1 h. To the solution was added water and the resulting mixture extracted twice with DCM. The combined organic layers were washed with brine, dried over Na$_2$SO$_4$ and concentrated under vacuum. The resulting residue was purified by silica gel chromatography (0-30% EA/PE) to yield N-(2-((tert-butyldimethylsilyl)oxy)-2-methylpropyl)-3-fluoro-4-iodopyridin-2-amine as a white solid. LC/MS: mass calculated for C$_{15}$H$_{26}$FIN$_2$OSi: 424.08, measured: 425.10 [M+H]$^+$.

Step 3: N-(2-((tert-butyldimethylsilyl)oxy)-2-methylpropyl)-N-(3-fluoro-4-iodopyridin-2-yl)acetamide A mixture of N-(2-((tert-butyldimethylsilyl)oxy)-2-methylpropyl)-3-fluoro-4-iodopyridin-2-amine (2.5 g, 5.89 mmol, 1.0 equiv.) in acetic anhydride (30 mL) was stirred at 110° C. overnight. The mixture was concentrated under vacuum. The residue was dissolved in EA and washed by NaHCO$_3$ saturated solution. The combined organic layers were washed with brine, dried over Na$_2$SO$_4$ and concentrated under vacuum. The resulting residue was purified by silica gel chromatography (0-50% EA/PE) to yield N-(2-((tert-butyldimethylsilyl)oxy)-2-methylpropyl)-N-(3-fluoro-4-iodopyridin-2-yl)acetamide as a white solid. LC/MS: mass calculated for C$_{17}$H$_{28}$FIN$_2$O$_2$Si: 466.09, measured: 467.10 [M+H]$^+$.

Step 4: N-(2-((tert-butyldimethylsilyl)oxy)-2-methylpropyl)-N-(3-fluoro-4-iodopyridin-2-yl)acetamide To a mixture of N-(2-((tert-butyldimethylsilyl)oxy)-2-methylpropyl)-N-(3-fluoro-4-iodopyridin-2-yl)acetamide (1.0 g, 2.14 mmol, 1.0 equiv.) in 1,4-dioxane (10 mL) was added tributyl(1-ethoxyvinyl)stannane (0.87 mL, 2.57 mmol, 1.2 equiv) and Pd(PPh$_3$)$_4$ (248 mg, 0.21 mmol, 0.1 equiv.). The flask was evacuated and flushed three times with nitrogen. The resulting solution was stirred at 100° C. for 3 h under nitrogen. After cooling to room temperature, to the reaction mixture was added water and the resulting mixture was extracted twice with EA. The combined organic layers were washed with brine, dried over Na$_2$SO$_4$ and concentrated under vacuum. The residue was purified by Al$_2$O$_3$ column (0-20% EA/PE) to yield N-(2-((tert-butyldimethylsilyl)oxy)-2-methylpropyl)-N-(3-fluoro-4-iodopyridin-2-yl)acetamide as a yellow oil. LC/MS: mass calculated for C$_{21}$H$_{35}$FN$_2$O$_3$Si: 410.24, measured: 411.40 [M+H]$^+$.

Step 5: N-(4-(2-bromoacetyl)-3-fluoropyridin-2-yl)-N-(2-((tert-butyldimethylsilyl)oxy)-2-methylpropyl)acetamide To a mixture of N-(2-((tert-butyldimethylsilyl)oxy)-2-methylpropyl)-N-(4-(1-ethoxyvinyl)-3-fluoropyridin-2-yl)acetamide (800 mg, 1.95 mmol, 1.0 equiv.) in THF (9 mL) and water (3 mL) was added N-bromosuccinimide (347 mg, 1.95 mmol, 1.0 equiv.). The solution was stirred at room temperature for 0.5 h. To the reaction mixture was added water, and the resulting mixture was extracted twice with EA. The combined organic layers were washed with brine, dried over Na$_2$SO$_4$ and concentrated under vacuum to yield N-(4-(2-bromoacetyl)-3-fluoropyridin-2-yl)-N-(2-((tert-butyldimethylsilyl)oxy)-2-methylpropyl)acetamide as a yellow solid. LC/MS: mass calculated for C$_{19}$H$_{30}$BrFN$_2$O$_3$Si: 460.12, measured: 463.30 [M+H+2]$^+$.

Intermediate 5: 2-Bromo-4-chloro-1-(difluoromethoxy)-3-fluorobenzene

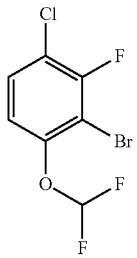

Step 1: 2-bromo-4-chloro-3-fluorophenol

To a solution of 2-bromo-3-fluorophenol (5.0 g, 26.18 mmol, 1.0 equiv.) in ACN (200 ml) at 0° C. was added NCS (3.5 g, 26.21 mmol, 1.0 equiv.) and TFA (3.3 ml). The reaction mixture was stirred overnight at room temperature. The reaction mixture was concentrated. The residue was purified by silica gel chromatography (0-20% EA/PE) to yield 2-bromo-4-chloro-3-fluorophenol as a yellow oil. LC/MS: mass calculated for $C_6H_3BrClFO$: 223.90, measured: 222.90[M+H]$^-$

Step 2: 2-bromo-4-chloro-1-(difluoromethoxy)-3-fluorobenzene

To a solution of 2-bromo-4-chloro-3-fluorophenol (3.7 g, 16.41 mmol, 1.0 equiv.) in DMF (60 ml) was added $Cs_2CO_3$ (10.7 g, 32.84 mmol, 2.0 equiv.) and sodium 2-chloro-2,2-difluoroacetate (5.0 g, 32.80 mmol, 2.0 equiv.). The reaction was stirred overnight at 90° C. After cooling to room temperature, the reaction mixture was poured into water (100 mL), then extracted with EA (3×100 mL). The organic layers were combined, washed with water (100 ml) and brine (100 ml), dried over $Na_2SO_4$, filtered and concentrated. The residue obtained was purified by silica gel chromatography (0-20% EA/PE) to yield 2-bromo-4-chloro-1-(difluoromethoxy)-3-fluorobenzene as a colorless oil. $^1$H NMR (300 MHz, Chloroform-d) δ 7.38 (dd, J=9.0, 7.8 Hz, 1H), 7.05-6.99 (m, 1H), 6.55 (t, J=72.5 Hz, 1H).

Intermediate 6: 4-(2-Bromoacetyl)-3-fluorobenzamide

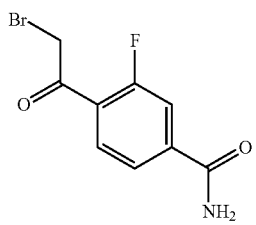

Step 1: 4-(1-ethoxyvinyl)-3-fluorobenzamide

Under an inert atmosphere of nitrogen, a mixture of 4-bromo-3-fluorobenzamide (1.0 g, 4.59 mmol, 1.0 equiv), tributyl(1-ethoxyvinyl)stannane (2.2 g, 6.09 mmol, 1.3 equiv), Pd(PPh$_3$)$_4$ (530 mg, 0.46 mmol, 0.1 equiv) in 1,4-dioxane (15 mL) was stirred at 90° C. for overnight, then concentrated under reduced pressure. The resulting residue was applied onto a silica gel column (80 g, EtOAc/PE: 1/10) to yield 4-(1-ethoxyvinyl)-3-fluorobenzamide as yellow oil.

Step 2: 4-(2-bromoacetyl)-3-fluorobenzamide

To a mixture of 4-(1-ethoxyvinyl)-3-fluorobenzamide (800 mg, 3.82 mmol, 1.0 equiv) in THF (10 mL) with H$_2$O (5 mL) was added NBS (681 mg, 3.83 mmol, 1.0 equiv) and the resulting mixture stirred at room temperature for 30 min. The reaction was quenched with water (50 mL), and the resulting mixture extracted with ethyl acetate (100 mL×3). The combined organic layer was washed with brine, dried over Na$_2$SO$_4$ and concentrated to yield 4-(2-bromoacetyl)-3-fluorobenzamide as a yellow solid.

Synthesis Examples: Compounds of Formula (1)

Example 1: (3S,9S*)-3-(5-(6-amino-2-fluoropyridin-3-yl)-1H-imidazol-2-yl)-7-(3-chloro-2-fluoro-6-(1H-tetrazol-1-yl)phenyl)-1,2,3,8,9,9a-hexahydro-5H-pyrrolo[1,2-a]azepin-5-one

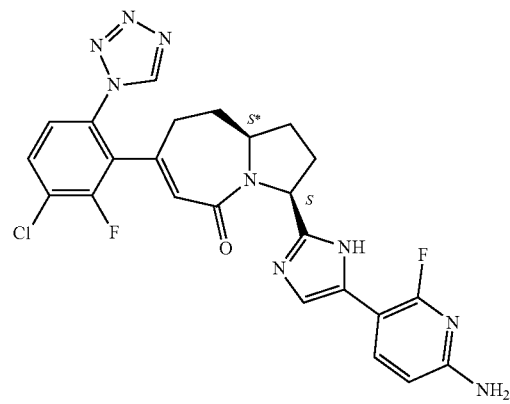

(ID No. 15)

Step 1: 2-(6-acetamido-2-fluoropyridin-3-yl)-2-oxoethyl (3S,9S)-7-(6-amino-3-chloro-2-fluorophenyl)-5-oxo-2,3,5,8,9,9a-hexahydro-1H-pyrrolo[1,2-a]azepine-3-carboxylate To a solution of (3S,9S)-7-(6-amino-3-chloro-2-fluorophenyl)-5-oxo-2,3,5,8,9,9a-hexahydro-1H-pyrrolo[1,2-a]azepine-3-carboxylic acid (351 mg, 1.04 mmol, 1.0 equiv.) in DMF (10 mL) was added cesium carbonate (197 mg, 0.61 mmol, 0.6 equiv.) and the resulting mixture was stirred at room temperature for 0.5 h. To the resulting mixture was then added N-(5-(2-bromoacetyl)-6-fluoropyridin-2-yl)acetamide (343 mg, 1.25 mmol, 1.2 equiv.). The mixture was stirred at room temperature for 2 h. The reaction was quenched with water (20 mL), and the resulting mixture was extracted with ethyl acetate (3×30 mL). The combined extracts were washed with water, dried over Na$_2$SO$_4$, filtered and purified by silica gel chromatography (0-10% MeOH/DCM) to yield 2-(6-acetamido-2-fluoropyridin-3-yl)-2-oxoethyl (3S,9S)-7-(6-amino-3-chloro-2-fluorophenyl)-5-oxo- 2,3,5,8,9,9a-hexahydro-1H-pyrrolo[1,2-a]azepine-3-carboxylate as a yellow oil. LC/MS: mass calculated for $C_{25}H_{23}ClF_2N_4O_5$: 532.13, measured: 533.10 [M+H]$^+$.

Step 2: N-(5-(2-((3S,9S)-7-(6-amino-3-chloro-2-fluorophenyl)-5-oxo-2,3,5,8,9,9a-hexahydro-1H-pyrrolo[1,2-a]azepin-3-yl)-1H-imidazol-5-yl)-6-fluoropyridin-2-yl)acetamide To a solution of 2-(6-acetamido-2-fluoropyridin-3-yl)-2-oxoethyl (3S,9S)-7-(6-amino-3-chloro-2-fluorophenyl)-5-oxo-2,3,5,8,9,9a-hexahydro-1H-pyrrolo[1,2-a]azepine-3-carboxylate (435 mg, 0.82 mmol, 1.0 equiv.) in toluene (10 mL) and acetic acid (1 mL) was added ammonium acetate (629 mg, 9.98 mmol, 10.0 equiv.). The resulting mixture was stirred at 90° C. for 3 h. After cooling to room temperature, the reaction was quenched with water (20 mL), and the resulting mixture extracted with ethyl acetate (3×50 mL). The organic layers were combined, dried over anhydrous sodium sulfate, filtered and concentrated. The residue obtained was purified by silica gel chromatography (0-10% methanol/DCM) to yield the N-(5-(2-((3S,9S)-7-(6-amino-3-chloro-2-fluorophenyl)-5-oxo-2,3,5,8,9,9a-hexahydro-1H-pyrrolo[1,2-a]azepin-3-yl)-1H-imidazol-5-yl)-6-fluoropyridin-2-yl)acetamide a yellow solid. LC/MS: mass calculated for $C_{25}H_{23}ClF_2N_6O_2$: 512.15, measured: 513.35 [M+H]$^+$ Step 3: N-(5-(2-((3S,9S)-7-(3-chloro-2-fluoro-6-(1H-tetrazol-1-yl)phenyl)-5-oxo-2,3,5,8,9,9a-hexahydro-1H-pyrrolo[1,2-a]azepin-3-yl)-1H-imidazol-5-yl)-6-fluoropyridin-2-yl)acetamide To a solution of N-(5-(2-((3S,9S)-7-(6-amino-3-chloro-2-fluorophenyl)-5-oxo-2,3,5,8,9,9a-hexahydro-1H-pyrrolo[1,2-a]azepin-3-yl)-1H-imidazol-5-yl)-6-fluoropyridin-2-yl)acetamide (352 mg, 0.69 mmol, 1.0 equiv.) in acetic acid (10 mL) was added azidotrimethylsilane (791 mg, 6.87 mmol, 10.0 equiv.), trimethoxymethane (728 mg, 6.86 mmol, 10.0 equiv.). The reaction mixture was then stirred at 65° C. for 3 h. The reaction was quenched with water (30 mL), and the resulting mixture extracted with ethyl acetate (3×30 mL). The organic layers were combined, dried over anhydrous sodium sulfate, filtered and concentrated. The residue obtained was purified by silica gel chromatography (0-10% methanol/DCM) to yield the N-(5-(2-((3S,9S)-7-(3-chloro-2-fluoro-6-(1H-tetrazol-1-yl)phenyl)-5-oxo-2,3,5,8,9,9a-hexahydro-1H-pyrrolo[1,2-a]azepin-3-yl)-1H-imidazol-5-yl)-6-fluoropyridin-2-yl)acetamide as a yellow solid. LC/MS: mass calculated for $C_{26}H_{22}ClF_2N_9O_2$: 565.16, measured: 566.35 [M+H]$^+$.

Step 4: N-(5-(2-((3S,9S)-7-(3-chloro-2-fluoro-6-(1H-tetrazol-1-yl)phenyl)-5-oxo-2,3,5,8,9,9a-hexahydro-1H-pyrrolo[1,2-a]azepin-3-yl)-1H-imidazol-5-yl)-6-fluoropyridin-2-yl)acetamide To a solution of (3S)-3-(5-(6-amino-2-fluoropyridin-3-yl)-1H-imidazol-2-yl)-7-(3-chloro-2-fluoro-6-(1H-tetrazol-1-yl)phenyl)-1,2,3,8,9,9a-hexahydro-5H-pyrrolo[1,2-a]azepin-5-one (230 mg, 0.41 mmol, 1.0 equiv.) in THF (1 mL) was added 4 N HCl solution (1 mL). The resulting mixture was stirred at 50° C. for 3 h. After cooling to room temperature, the reaction mixture was diluted with water and then extracted with EA. The organic layers were combined, dried over anhydrous sodium sulfate, filtered and concentrated to dryness under reduced pressure to yield a residue, which was purified by C18 column (eluent: 5% to 50% (v/v) $CH_3CN$ and $H_2O$ with 0.05% $NH_4HCO_3$) and chiral-HPLC using a Column: CHIRALPAK IA-3, 4.6*50 mm; 3 um; Mobile Phase A: MtBE (0.1% DEA):EtOH=80:20, Mobile Phase B:; Flow rate: 1 mL/min to yield (3S,9S*)-3-(5-(6-amino-2-fluoropyridin-3-yl)-1H-imidazol-2-yl)-7-(3-chloro-2-fluoro-6-(1H-tetrazol-1-yl)phenyl)-1,2,3,8,9,9a-hexahydro-5H-pyrrolo[1,2-a]azepin-5-one as a white solid. LC/MS: mass calculated for $C_{24}H_{20}ClF_2N_9O$: 523.14, measured (ES, m/z): 524.15 [M+H]$^+$. $^1$H NMR (300 MHz, DMSO-d$_6$) δ 11.81 (br, 1H), 9.81 (s, 1H), 7.84-8.03 (m, 2H), 7.65 (d, J=8.7 Hz, 1H), 6.98-7.06 (m, 1H), 6.37 (d, J=8.2 Hz, 1H), 6.18-6.26 (m, 2H), 5.72 (s, 1H), 5.03 (d, J=6.1 Hz, 1H), 3.43-3.63 (m, 1H), 2.61-2.80 (m, 1H), 2.23-2.39 (m, 1H), 1.87-2.20 (m, 6H). $^{19}$F NMR (282 MHz, DMSO-d$_6$) δ −70.04, −70.76, −114.02.

Example 2: 4-((3S*,9aS*)-7-(3-chloro-6-(difluoromethoxy)-2-fluorophenyl)-5-oxo-2,3,5,8,9,9a-hexahydro-1H-pyrrolo[1,2-a]azepine-3-carboxamido)benzoic acid

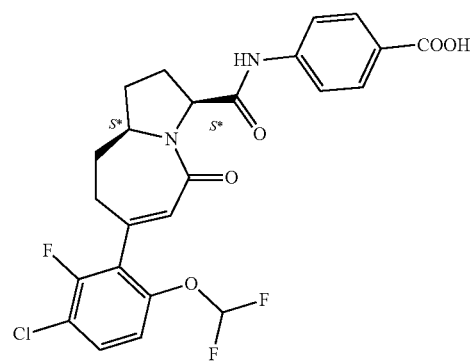

(ID No. 3)

Step 1: methyl (3*S)-5-oxo-7-(4,4,5,5-tetramethyl-1,3,2-dioxaborolan-2-yl)-2,3,5,8,9,9a-hexahydro-1H-pyrrolo[1,2-a]azepine-3-carboxylate To a solution of methyl (3S*)-5-oxo-7-(((trifluoromethyl)sulfonyl)oxy)-2,3,5,8,9,9a-hexahydro-1H-pyrrolo[1,2-a]azepine-3-carboxylate (500 mg, 1.40 mmol, 1.0 equiv.) in 1,4-dioxane (10 ml) was added KOAc (275 mg g, 2.80 mmol, 2.0 equiv.), 4,4,4',4',5,5,5',5'-octamethyl-2,2'-bi(1,3,2-dioxaborolane) (533 mg, 2.10 mmol, 1.5 equiv.), and Pd(dppf)Cl$_2$ (102 mg, 0.14 mmol, 0.1 equiv.) under N$_2$. The reaction mixture was then stirred for 4 h at 90° C. After cooling to room temperature, the resulting mixture was concentrated to yield methyl (3*S)-5-oxo-7-(4,4,5,5-tetramethyl-1,3,2-dioxaborolan-2-yl)-2,3,5,8,9,9a-hexahydro-1H-pyrrolo[1,2-a]azepine-3-carboxylate as a yellow oil, which was used in the next step without further purification. LC/MS: mass calculated for $C_{12}H_{14}F_3NO_6S$: 335.19, measured: 336.20[M+H]$^+$ Step 2: methyl (3*S)-7-(3-chloro-6-(difluoromethoxy)-2-fluorophenyl)-5-oxo-2,3,5,8,9,9a-hexahydro-1H-pyrrolo[1,2-a]azepine-3-carboxylate To a solution of 2-bromo-4-chloro-1-(difluoromethoxy)-3-fluorobenzene (500 mg, 1.82 mmol, 1.0 equiv.) in 1,4- dioxane/H$_2$O (12 ml, 4/1) was added ((3S*)-3-(methoxycarbonyl)-5-oxo-2,3,5,8,9,9a-hexahydro-1H-pyrrolo[1,2-a]azepin-7-yl)boronic acid (459 mg, 1.81 mmol, 1.0 equiv.), K$_3$PO$_4$ (770 mg, 3.63 mmol, 2.0 equiv.), and Pd(dppf)Cl$_2$ (133 mg, 0.18 mmol, 0.1 equiv.) under N$_2$. The reaction mixture was stirred for 4 h at 90° C. After cooling to room temperature, the reaction was quenched with water (50 ml). The resulting mixture was extracted with EA (3×50 mL). The organic layers were combined, dried over Na$_2$SO$_4$, filtered and concentrated. The residue was purified by silica gel chromatography (0-50% EA/PE) to yield methyl (3*S)-7-(3-chloro-6-(difluoromethoxy)-2-fluorophenyl)-5-oxo-2,3,5,8,9,9a-hexahydro-1H-pyrrolo[1,2-a]azepine-3-carboxylate as a yellow oil. LC/MS: mass calculated for C$_{18}$H$_{17}$ClF$_3$NO$_4$: 403.08, measured: 404.20[M+H]$^+$.

Step 3: (3*S)-7-(3-chloro-6-(difluoromethoxy)-2-fluorophenyl)-5-oxo-2,3,5,8,9,9a-hexahydro-1H-pyrrolo[1,2-a]azepine-3-carboxylic acid To a solution of methyl (3*S)-7-(3-chloro-6-(difluoromethoxy)-2-fluorophenyl)-5-oxo-2,3,5,8,9,9a-hexahydro-1H-pyrrolo[1,2-a]azepine-3-carboxylate (540 mg, 1.34 mmol, 1.0 equiv) in THF/H$_2$O (8 ml, 3/1) at 0° C. was added LiOH (64 mg, 2.67 mmol, 2.0 equiv). The mixture was then stirred for 1 h at room temperature. The resulting solution was concentrated and then diluted with water (20 ml). The water layers were adjusted to pH 4-5 with 2N HCl and extracted with EA (3×50 mL). The organic layers were combined, dried over Na$_2$SO$_4$, filtered and concentrated under reduced pressure. The residue was purified by reverse C18 column (10-60% H$_2$O (0.05% TFA)/ACN) to yield (3*S)-7-(3-chloro-6-(difluoromethoxy)-2-fluorophenyl)-5-oxo-2,3,5,8,9,9a-hexahydro-1H-pyrrolo[1,2-a]azepine-3-carboxylic acid as a yellow oil. LC/MS: mass calculated for C$_{17}$H$_{15}$ClF$_3$NO$_4$: 389.06, measured: 390.20[M+H]$^+$.

Step 4: tert-butyl 4-((3*S)-7-(3-chloro-6-(difluoromethoxy)-2-fluorophenyl)-5-oxo-2,3,5,8,9,9a-hexahydro-1H-pyrrolo[1,2-a]azepine-3-carboxamido)benzoate To a solution of (3*S)-7-(3-chloro-6-(difluoromethoxy)-2-fluorophenyl)-5-oxo-2,3,5,8,9,9a-hexahydro-1H-pyrrolo[1,2-a]azepine-3-carboxylic acid (220 mg, 0.56 mmol, 1.0 equiv.) in pyridine (8 ml) was added tert-butyl 4-aminobenzoate (164 mg, 0.85 mmol, 1.5 equiv.) and EDCl (216 mg, 1.13 mmol, 2.0 equiv.) under N$_2$. The reaction mixture was then stirred for 3 h at room temperature. The resulting mixture was concentrated under reduced pressure. The resulting residue was purified by reverse C18 column (15-80% H$_2$O (0.05% TFA)/ACN) to yield tert-butyl 4-((3*S)-7-(3-chloro-6-(difluoromethoxy)-2-fluorophenyl)-5-oxo-2,3,5,8,9,9a-hexahydro-1H-pyrrolo[1,2-a]azepine-3-carboxamido)benzoate as an off-white solid. LC/MS: mass calculated for C$_{28}$H$_{28}$ClF$_3$N$_2$O$_5$: 564.16, measured: 565.20 [M+H]$^+$.

Step 5: 4-((3*S,9*S)-7-(3-chloro-6-(difluoromethoxy)-2-fluorophenyl)-5-oxo-2,3,5,8,9,9a-hexahydro-1H-pyrrolo[1,2-a]azepine-3-carboxamido)benzoic acid To a solution of tert-butyl 4-((3*S)-7-(3-chloro-6-(difluoromethoxy)-2-fluorophenyl)-5-oxo-2,3,5,8,9,9a-hexahydro-1H-pyrrolo[1,2-a]azepine-3-carboxamido)benzoate (250 mg, 0.49 mmol, 1.0 equiv.) in DCM (10 ml) at 0° C. was added TFA (2 ml). The resulting mixture was then stirred for 3 h at room temperature. The resulting mixture was concentrated and purified by reverse C18 column (15-80% H$_2$O (0.05% TFA)/ACN) and then Prep-Chiral-HPLC using a (R, R) WHELK-01, 4.6*50 mm, 3.5 um column (eluent: Hex (0.1% TFA):EtOH=80:20), Flow rate: 1 mL/min to yield 4-((3*S,9*S)-7-(3-chloro-6-(difluoromethoxy)-2-fluorophenyl)-5-oxo-2,3,5,8,9,9a-hexahydro-1H-pyrrolo[1,2-a]azepine-3-carboxamido)benzoic acid as a white solid.

LC/MS: mass calculated for C$_{24}$H$_{20}$ClF$_3$N$_2$O$_5$: 508.10, measured (ES, m/z): 509.05 [M+H]$^+$. $^1$H NMR (300 MHz, DMSO-d$_6$) δ 12.74 (br, 1H), 10.51 (s, 1H), 7.94-7.85 (m, 2H), 7.69-7.71 (m, 2H), 7.66 (t, J=8.7 Hz, 1H), 7.29-7.31 (m, 1H), 7.16 (d, J=8.7 Hz, 1H), 5.89 (d, J=1.5 Hz, 1H), 4.64-4.54 (m, 1H), 4.12-3.70 (m, 1H), 2.85-2.71 (m, 1H), 2.46-2.32 (m, 1H), 2.27-2.13 (m, 4H), 2.13-1.95 (m, 1H), 1.90-1.77 (m, 1H). $^{19}$F NMR (282 MHz, DMSO-d$_6$) δ −82.29, −114.88.

Additional representative compounds of formula (I) of the present invention were similarly prepared according to the procedures as described in the Schemes and Examples herein, selecting and substituting suitably selected reagents and reactants, as would be readily recognized by those skilled in the art.

Example 3: (3S,9aS)-3-(5-(2-amino-3-fluoropyridin-4-yl)-1H-imidazol-2-yl)-7-(5-chloro-2-(1H-tetrazol-1-yl)phenyl)-1,2,3,8,9,9a-hexahydro-5H-pyrrolo[1,2-a]azepin-5-one (ID No. 9)

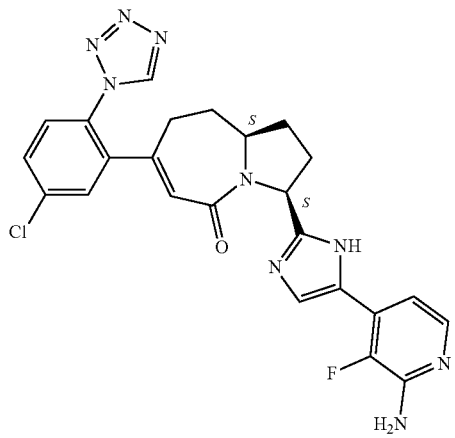

LC/MS: mass calculated for C$_{24}$H$_{21}$ClFN$_9$O: 505.15, measured (ES, m/z): 506.15 [M+H]$^+$. $^1$H NMR (300 MHz, DMSO-d$_6$) δ 12.18 (br, 1H), 9.84 (s, 1H), 7.67-7.80 (m, 4H), 7.41-7.46 (m, 1H), 7.06 (t, J=5.1 Hz, 1H), 6.01-6.05 (m, 2H), 5.62 (d, J=1.5 Hz, 1H), 5.08-5.10 (m, 1H), 3.61-3.68 (m, 1H), 2.63-2.75 (m, 1H), 1.89-2.29 (m, 7H). $^{19}$F NMR (282 MHz, DMSO-d$_6$) δ −142.41.

Example 4: (3S,9aS)-7-(5-chloro-2-(1H-tetrazol-1-yl)phenyl)-3-(5-(2-(ethylamino)-3-fluoropyridin-4-yl)-1H-imidazol-2-yl)-1,2,3,8,9,9a-hexahydro-5H-pyrrolo[1,2-a]azepin-5-one (ID No. 8)

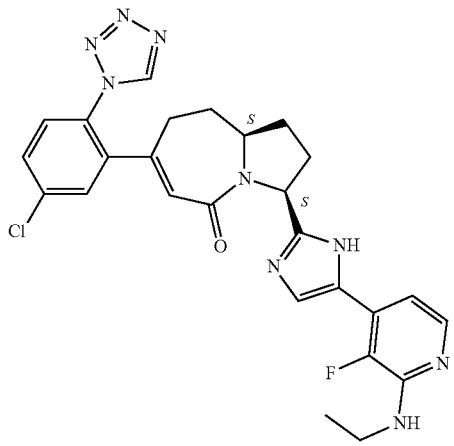

LC/MS: mass calculated for C$_{26}$H$_{25}$ClFN$_9$O: 533.19, measured (ES, m/z): 534.15 [M+H]$^+$. $^1$H NMR (300 MHz, DMSO-d$_6$) δ 12.19 (br, 1H), 9.84 (s, 1H), 7.67-7.85 (m, 4H), 7.40-7.47 (m, 1H), 7.03 (t, J=5.1 Hz, 1H), 6.44-6.48 (m, 1H), 5.61 (d, J=1.4 Hz, 1H), 5.07-5.13 (m, 1H), 3.60-6.70 (m, 1H), 3.33-3.42 (m, 2H), 2.64-2.74 (m, 1H), 1.84-2.28 (m, 7H), 1.15 (t, J=7.1 Hz, 3H). $^{19}$F NMR (282 MHz, DMSO-d$_6$) δ −143.60.

Example 5: (3S)-3-(5-(2-amino-3-fluoropyridin-4-yl)-4-fluoro-1H-imidazol-2-yl)-7-(5-chloro-2-(1H-tetrazol-1-yl)phenyl)-1,2,3,8,9,9a-hexahydro-5H-pyrrolo[1,2-a]azepin-5-one (ID No. 4)

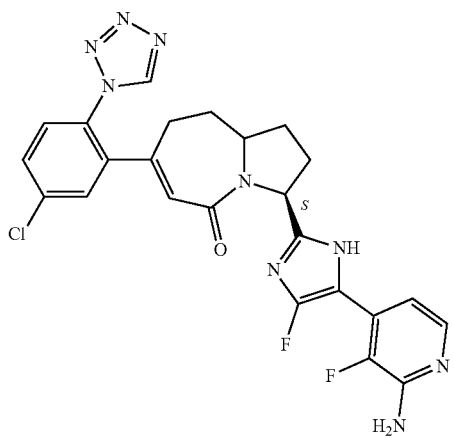

LC/MS: mass calculated for C$_{24}$H$_{20}$ClF$_2$N$_9$O: 523.14, measured (ES, m/z): 524.15 [M+H]$^+$. $^1$H NMR (300 MHz, DMSO-d$_6$) δ 12.44 (br, 1H), 9.84 (s, 1H), 7.59-7.83 (m, 4H), 6.62-6.71 (m, 1H), 6.27-6.33 (m, 2H), 5.57 (d, J=1.3 Hz, 1H), 5.00-5.09 (m, 1H), 3.57-3.66 (m, 1H), 2.58-2.70 (m, 1H), 2.03-2.32 (m, 4H), 1.84-1.96 (m, 3H).

Example 6: N-(4-(2-((3S)-7-(5-chloro-2-(1H-tetrazol-1-yl)phenyl)-5-oxo-2,3,5,8,9,9a-hexahydro-1H-pyrrolo[1,2-a]azepin-3-yl)-4-fluoro-1H-imidazol-5-yl)-3-fluoropyridin-2-yl)acetamide (ID No. 5)

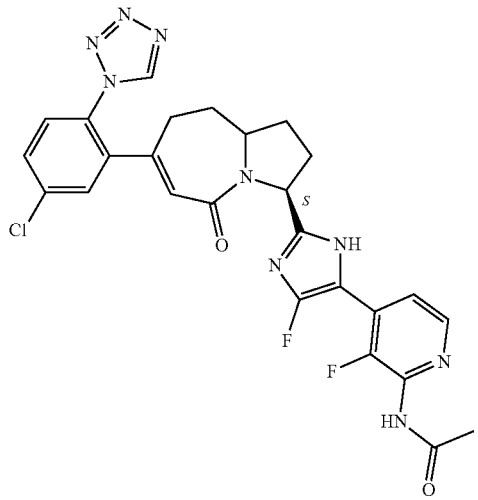

LC/MS: mass calculated for C$_{26}$H$_{22}$ClF$_2$N$_9$O$_2$: 565.16, measured (ES, m/z): 566.10 [M+H]$^+$. $^1$H NMR (300 MHz, DMSO-d$_6$) δ 12.65 (br, 1H), 10.20 (br, 1H), 9.84 (s, 1H), 8.11-8.18 (m, 1H), 7.67-7.81 (m, 3H), 7.42 (t, J=5.3 Hz, 1H), 5.57 (d, J=1.4 Hz, 1H), 5.00-5.06 (m, 1H), 3.57-3.65 (m, 1H), 2.63-2.72 (m, 1H), 2.08-2.31 (m, 7H), 1.78-1.95 (m, 3H).

Example 7: 4-(2-((3S,9aR)-7-(3-chloro-2-fluoro-6-(1H-tetrazol-1-yl)phenyl)-5-oxo-2,3,5,8,9,9a-hexahydro-1H-pyrrolo[1,2-a]azepin-3-yl)-1H-imidazol-5-yl)-3-fluorobenzamide (ID No.1)

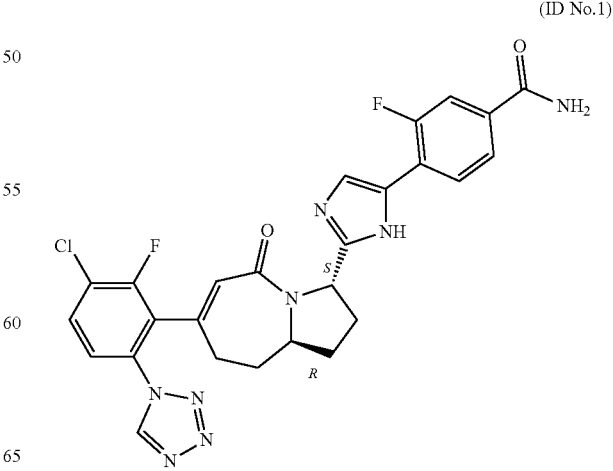

LC/MS: mass calculated for $C_{26}H_{21}ClF_2N_8O_2$: 550.14, measured (ES, m/z): 551.15 [M+H]⁺. ¹H NMR (400 MHz, DMSO-$d_6$) δ 12.15 (br, 1H), 9.79 (s, 1H), 7.97-8.07 (m, 2H), 7.80-7.85 (m, 1H), 7.68-7.75 (m, 2H), 7.58-7.61 (m, 1H), 7.36-7.50 (m, 2H), 5.50 (s, 1H), 5.16 (d, J=8.2 Hz, 1H), 4.17 (s, 1H), 3.71-3.78 (m, 1H), 2.61-2.70 (m, 2H), 2.20-2.32 (m, 2H), 1.95-2.11 (m, 3H).

Example 8: 4-(2-((3S,9aS)-7-(3-chloro-2-fluoro-6-(1H-tetrazol-1-yl)phenyl)-5-oxo-2,3,5,8,9,9a-hexahydro-1H-pyrrolo[1,2-a]azepin-3-yl)-1H-imidazol-5-yl)-3-fluorobenzamide LC/MS: mass calculated for $C_{24}H_{21}ClFN_9O$: 505.15, measured (ES, m/z): 506.15 [M+H]⁺. ¹H NMR (400 MHz, DMSO-$d_6$) δ 11.81 (br, 1H), 9.83 (s, 1H), 7.93-8.02 (m, 1H), 7.68-7.81 (m, 3H), 6.89-7.06 (m, 1H), 6.14-6.45 (m, 3H), 5.52-5.62 (m, 1H), 5.01-5.08 (m, 1H), 3.56-3.72 (m, 1H), 2.61-2.73 (m, 1H), 1.78-2.36 (m, 7H). ¹⁹F NMR (376 MHz, DMSO-$d_6$) δ −70.78.

Example 10: (3R,9aS)-3-(5-(6-amino-2-fluoropyridin-3-yl)-1H-imidazol-2-yl)-7-(5-chloro-2-(1H-tetrazol-1-yl)phenyl)-1,2,3,8,9,9a-hexahydro-5H-pyrrolo[1,2-a]azepin-5-one

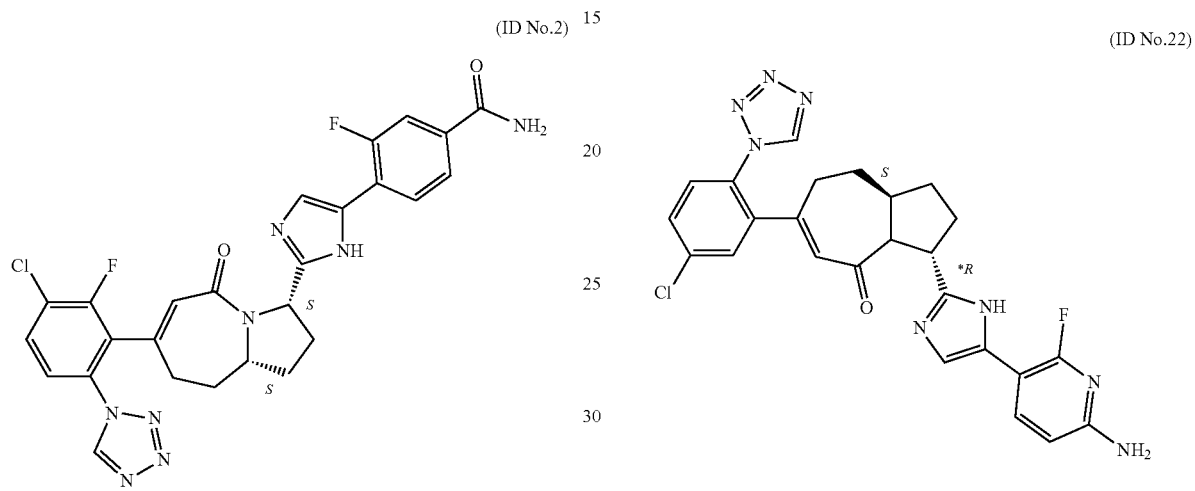

(ID No.2)

(ID No.22)

LC/MS: mass calculated for $C_{26}H_{21}ClF_2N_8O_2$: 550.14, measured (ES, m/z): 551.15 [M+H]⁺. ¹H NMR (400 MHz, DMSO-$d_6$) δ 12.16 (br, 1H), 9.83 (s, 1H), 7.98-8.07 (m, 2H), 7.88-7.97 (m, 1H), 7.67-7.77 (m, 3H), 7.42-7.44 (m, 2H), 5.74 (d, J=1.7 Hz, 1H), 5.06-5.13 (m, 1H), 3.45-3.60 (m, 1H), 2.65-2.82 (m, 1H), 2.28-2.39 (m, 1H), 1.89-2.19 (m, 6H). ¹⁹F NMR (376 MHz, DMSO-$d_6$) δ −114.02, −114.56.

Example 9: (3S,9aS)-3-(5-(6-amino-2-fluoropyridin-3-yl)-1H-imidazol-2-yl)-7-(5-chloro-2-(1H-tetrazol-1-yl)phenyl)-1,2,3,8,9,9a-hexahydro-5H-pyrrolo[1,2-a]azepin-5-one LC/MS: mass calculated for $C_{24}H_{21}ClFN_9O$: 505.15, measured (ES, m/z): 506.15 [M+H]⁺. ¹H NMR (400 MHz, Methanol-$d_4$) δ 9.46 (s, 1H), 8.00-8.06 (m, 1H), 7.51-7.62 (m, 3H), 7.21 (d, J=3.4 Hz, 1H), 6.48 (dd, J=8.3, 1.9 Hz, 1H), 5.60-5.68 (m, 1H), 5.21 (dd, J=7.7, 3.2 Hz, 1H), 4.30-4.42 (m, 1H), 3.73-3.83 (m, 1H), 2.61 (d, J=16.4 Hz, 1H), 2.32-2.53 (m, 4H), 2.14-2.28 (m, 1H), 1.83-1.98 (m, 1H). ¹⁹F NMR (376 MHz, Methanol-$d_4$) δ −76.93.

Example 11: (3S,9aR)-3-(5-(6-amino-2-fluoropyridin-3-yl)-1H-imidazol-2-yl)-7-(3-chloro-2-fluoro-6-(1H-tetrazol-1-yl)phenyl)-1,2,3,8,9,9a-hexahydro-5H-pyrrolo[1,2-a]azepin-5-one

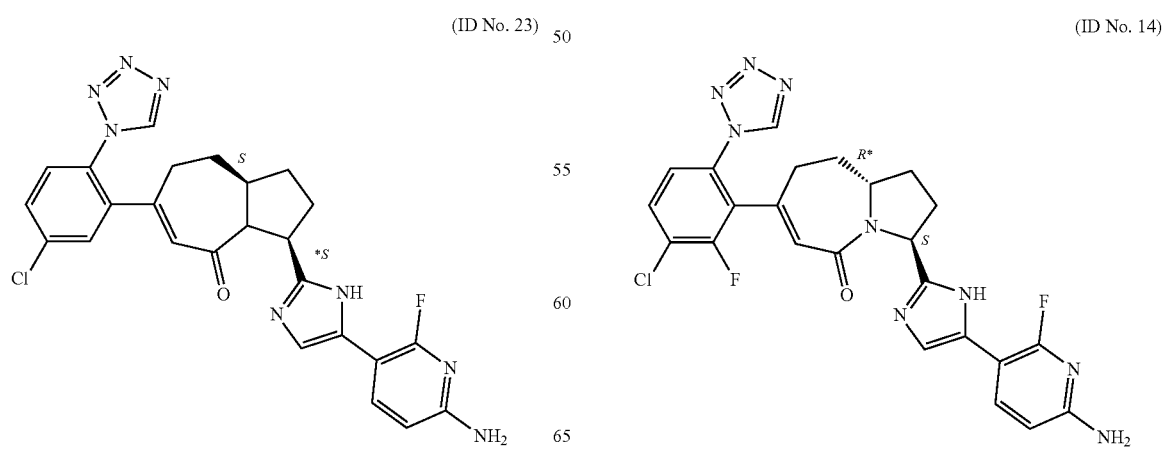

(ID No. 23)

(ID No. 14)

LC/MS: mass calculated for $C_{24}H_{20}ClF_2N_9O$: 523.14, measured (ES, m/z): 524.15 [M+H]$^+$. $^1$H NMR (300 MHz, DMSO-d$_6$) δ 11.80 (br, 1H), 9.76 (s, 1H), 7.86-8.03 (m, 1H), 7.75-7.86 (m, 1H), 7.57 (d, J=8.7 Hz, 1H), 7.04 (s, 1H), 6.28-6.45 (m, 1H), 6.15-6.26 (m, 2H), 5.46 (s, 1H), 5.07-5.11 (m, 1H), 4.02-4.21 (m, 1H), 3.65-3.80 (m, 1H), 2.51-2.71 (m, 1H), 2.12-2.29 (m, 2H), 1.83-2.10 (m, 4H). $^{19}$F NMR (282 MHz, DMSO-d$_6$) δ −70.11, −114.02.

Example 12: (3S,9aS)-3-(5-(2-amino-3-fluoropyridin-4-yl)-1H-imidazol-2-yl)-7-(3-chloro-2-fluoro-6-(1H-tetrazol-1-yl)phenyl)-1,2,3,8,9,9a-hexahydro-5H-pyrrolo[1,2-a]azepin-5-one (ID No. 16)

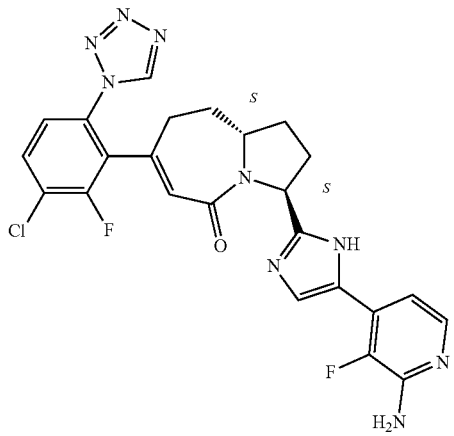

LC/MS: mass calculated for $C_{24}H_{20}ClF_2N_9O$: 523.14, measured (ES, m/z): 524.15 [M+H]$^+$. $^1$H NMR (400 MHz, DMSO-d$_6$) δ 12.20 (br, 1H), 9.83 (s, 1H), 7.92 (t, J=8.0 Hz, 1H), 7.61-7.77 (m, 2H), 7.45 (s, 1H), 6.99-7.13 (m, 1H), 6.05 (s, 2H), 5.73 (s, 1H), 5.00-5.16 (m, 1H), 3.44-3.70 (m, 1H), 2.62-2.86 (m, 1H), 2.26-2.42 (m, 1H), 1.85-2.25 (m, 6H). $^{19}$F NMR (376 MHz, DMSO-d$_6$) δ −114.00.

Example 13: (3S,9aS)-7-(3-chloro-2-fluoro-6-(1H-tetrazol-1-yl)phenyl)-3-(5-(3-fluoro-2-(hydroxymethyl)pyridin-4-yl)-1H-imidazol-2-yl)-1,2,3,8,9,9a-hexahydro-5H-pyrrolo[1,2-a]azepin-5-one (ID No. 17)

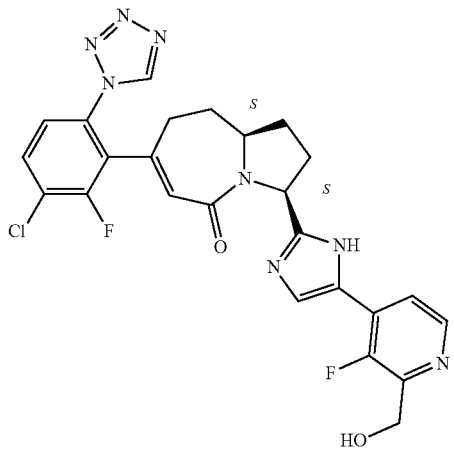

LC/MS: mass calculated for $C_{25}H_{21}ClF_2N_8O_2$: 538.14, measured (ES, m/z): 539.15 [M+H]$^+$. $^1$H NMR (400 MHz, DMSO-d$_6$) δ 12.33 (br, 1H), 9.84 (s, 1H), 8.33 (d, J=5.0 Hz, 1H), 7.93 (t, J=8.0 Hz, 1H), 7.84 (t, J=5.4 Hz, 1H), 7.68 (dd, J=8.6, 1.5 Hz, 1H), 7.52-7.62 (m, 1H), 5.74 (s, 1H), 5.27 (t, J=5.9 Hz, 1H), 5.03-5.14 (m, 1H), 4.55-4.68 (m, 2H), 3.44-3.70 (m, 1H), 2.62-2.86 (m, 1H), 2.28-2.40 (m, 1H), 1.84-2.27 (m, 6H). $^{19}$F NMR (376 MHz, DMSO-d$_6$) δ −114.01, −130.14.

Example 14: 4-(2-((3S,9aS)-7-(3-chloro-2-fluoro-6-(4-(trifluoromethyl)-1H-1,2,3-triazol-1-yl)phenyl)-5-oxo-2,3,5,8,9,9a-hexahydro-1H-pyrrolo[1,2-a]azepin-3-yl)-1H-imidazol-5-yl)-3-fluoropicolinic acid (ID NO. 6)

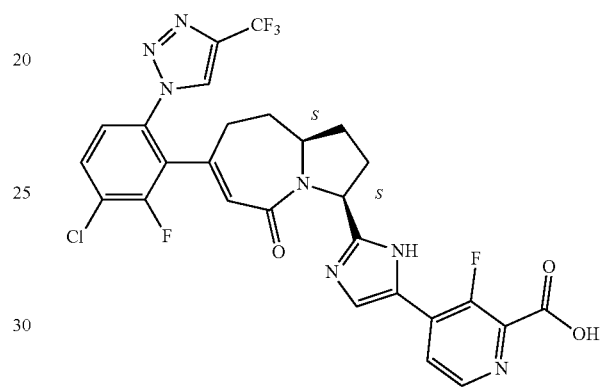

LC/MS: mass calculated for $C_{27}H_{19}ClF_5N_7O_3$: 619.12, measured (ES, m/z): 620.15 [M+H]$^+$. $^1$H NMR (400 MHz, DMSO-d$_6$) δ 9.37 (s, 1H), 8.47 (d, J=4.9 Hz, 1H), 8.07 (t, J=5.3 Hz, 1H), 7.93 (t, J=8.2 Hz, 1H), 7.63-7.81 (m, 2H), 5.77 (s, 1H), 5.07-5.16 (m, 1H), 3.26-3.70 (m, 1H), 2.65-2.85 (m, 1H), 2.26-2.42 (m, 1H), 2.03-2.24 (m, 4H), 1.79-2.01 (m, 2H). $^{19}$F NMR (376 MHz, DMSO-d$_6$) δ −59.68, −114.06, −124.13.

Example 15: 4-(2-((3S,9aS)-7-(5-chloro-2-(4-(trifluoromethyl)-1H-1,2,3-triazol-1-yl)phenyl)-5-oxo-2,3,5,8,9,9a-hexahydro-1H-pyrrolo[1,2-a]azepin-3-yl)-1H-imidazol-5-yl)-3-fluoropicolinic acid (ID NO. 7)

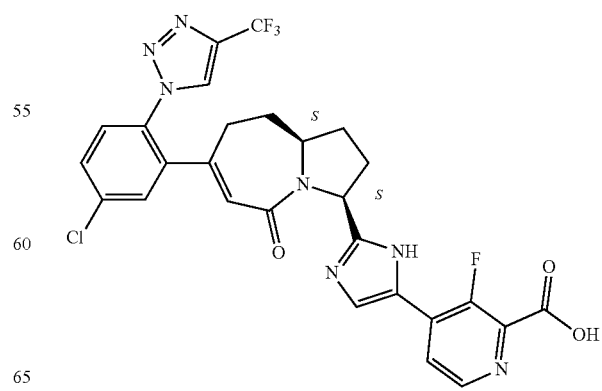

LC/MS: mass calculated for $C_{27}H_{20}ClF_4N_7O_3$: 601.13, measured (ES, m/z): 602.10 [M+H]⁺. ¹H NMR (400 MHz, Methanol-d₄) δ 8.96 (s, 1H), 8.10-8.38 (m, 2H), 7.52-7.77 (m, 4H), 5.79 (s, 1H), 5.21 (s, 1H), 3.76-3.89 (m, 1H), 2.62-2.78 (m, 1H), 2.11-2.40 (m, 5H), 1.84-2.08 (m, 2H). ¹⁹F NMR (376 MHz, Methanol-d₄) δ −62.51.

Example 16: 3S,9aS)-7-(3-chloro-2-fluoro-6-(1H-tetrazol-1-yl)phenyl)-5-oxo-N-(quinoxalin-6-yl)-2,3,5,8,9,9a-hexahydro-1H-pyrrolo[1,2-a]azepine-3-carboxamide

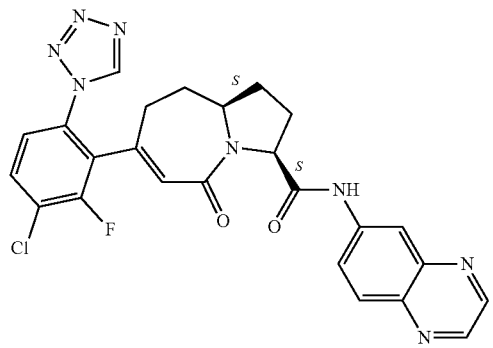

(ID No. 19)

LC/MS: mass calculated for $C_{25}H_{20}ClFN_8O_2$: 518.14, measured (ES, m/z): 519.15 [M+H]⁺. ¹H NMR (400 MHz, DMSO-d₆) δ 10.69 (s, 1H), 9.84 (s, 1H), 8.89 (d, J=1.9 Hz, 1H), 8.82 (d, J=1.9 Hz, 1H), 8.50 (d, J=2.3 Hz, 1H), 8.03-8.07 (m, 1H), 7.89-7.98 (m, 2H), 7.66-7.70 (m, 1H), 5.74-5.76 (m, 1H), 4.52-4.59 (m, 1H), 3.51-3.62 (m, 1H), 2.67-2.76 (m, 1H), 2.32-2.44 (m, 1H), 2.13-2.22 (m, 2H), 1.96-2.27 (m, 3H), 1.76-1.84 (m, 1H). ¹⁹F NMR (376 MHz, DMSO-d₆) δ −114.01

Example 17: (3S,9aR)-7-(5-chloro-2-(1H-tetrazol-1-yl)phenyl)-3-(5-(3-fluoro-2-((2-hydroxy-2-methylpropyl)amino)pyridin-4-yl)-1H-imidazol-2-yl)-1,2,3,8,9,9a-hexahydro-5H-pyrrolo[1,2-a]azepin-5-one

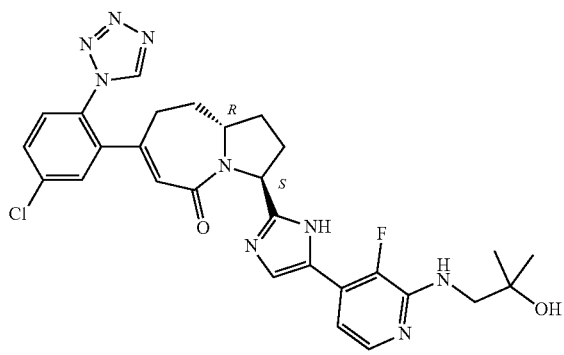

(ID No. 13)

LC/MS: mass calculated for $C_{28}H_{29}ClFN_9O_2$: 577.21, measured (ES, m/z): 578.25 [M+H]⁺. ¹H NMR (300 MHz, DMSO-d₆) δ 9.68 (s, 1H), 7.67-7.80 (m, 2H), 7.45-7.66 (m, 3H), 7.19 (t, J=5.8 Hz, 1H), 5.63 (s, 1H), 5.04-5.15 (m, 1H), 4.15-4.35 (m, 1H), 3.37 (s, 2H), 2.20-2.47 (m, 5H), 2.00-2.18 (m, 2H), 1.69-1.92 (m, 1H), 1.16 (s, 6H). ¹⁹F NMR (282 MHz, DMSO-d₆) δ −73.77, −105.50.

Example 18: (3S,9aS)-7-(5-chloro-2-(1H-tetrazol-1-yl)phenyl)-3-(5-(3-fluoro-2-((2-hydroxy-2-methylpropyl)amino)pyridin-4-yl)-1H-imidazol-2-yl)-1,2,3,8,9,9a-hexahydro-5H-pyrrolo[1,2-a]azepin-5-one

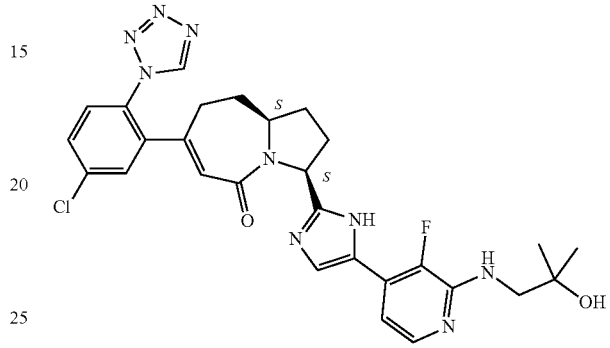

(ID No. 12)

LC/MS: mass calculated for $C_{28}H_{29}ClFN_9O_2$: 577.21, measured (ES, m/z): 578.25 [M+H]⁺. ¹H NMR (300 MHz, DMSO-d₆) δ 12.27 (br, 1H), 9.84 (s, 1H), 7.82-7.68 (m, 4H), 7.45-7.60 (m, 1H), 7.03-7.13 (m, 1H), 5.57-5.66 (m, 1H), 5.03-5.16 (m, 1H), 3.55-3.78 (m, 1H), 3.38-3.45 (m, 2H), 2.60-2.78 (m, 1H), 2.06-2.37 (m, 4H), 1.82-2.05 (m, 3H), 1.14 (s, 6H). ¹⁹F NMR (282 MHz, DMSO-d₆) δ −66.13, −177.0.

Example 19: (3S,9aS)-N-(4-carbamoyl-3-fluorophenyl)-7-(3-chloro-2-fluoro-6-(1H-tetrazol-1-yl)phenyl)-5-oxo-2,3,5,8,9,9a-hexahydro-1H-pyrrolo[1,2-a]azepine-3-carboxamide

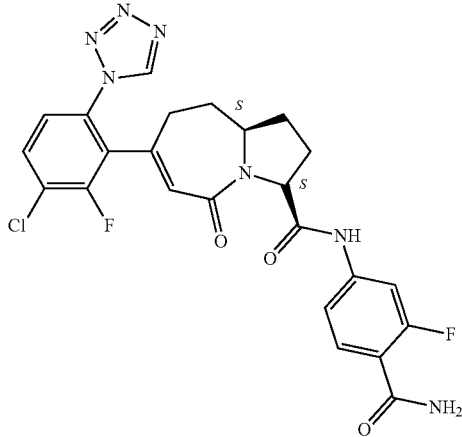

(ID No.21)

LC/MS: mass calculated for $C_{24}H_{20}ClF_2N_7O_3$: 527.13, measured (ES, m/z): 528.15 [M+H]⁺. ¹H NMR (400 MHz, DMSO-d₆) δ 10.56 (s, 1H), 9.83 (s, 1H), 7.93 (t, J=8.2 Hz, 1H), 7.60-7.72 (m, 3H), 7.48-7.53 (m, 2H), 7.31-7.37 (m, 1H), 5.74 (s, 1H), 4.43-4.51 (m, 1H), 3.48-3.56 (m, 1H), 2.64-2.72 (m, 1H), 2.31-2.40 (m, 1H), 2.11-2.18 (m, 2H), 1.90-2.01 (m, 3H), 1.71-1.80 (m, 1H). $^{19}$F NMR (376 MHz, DMSO-$d_6$) δ −110.93, −114.04.

Example 20: (3S,9aR)-N-(4-carbamoyl-3-fluorophenyl)-7-(3-chloro-2-fluoro-6-(1H-tetrazol-1-yl)phenyl)-5-oxo-2,3,5,8,9,9a-hexahydro-1H-pyrrolo[1,2-a]azepine-3-carboxamide

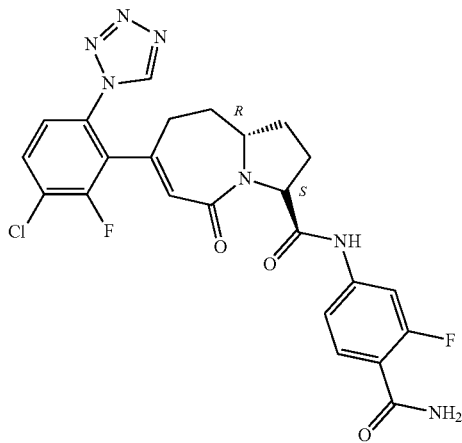

(ID No.20)

LC/MS: mass calculated for $C_{24}H_{20}ClF_2N_7O_3$: 527.13, measured (ES, m/z): 528.15 [M+H]$^+$. $^1$H NMR (400 MHz, DMSO-$d_6$) δ 10.54 (s, 1H), 9.78 (s, 1H), 7.84 (t, J=8.2 Hz, 1H), 7.56-7.73 (m, 3H), 7.50-7.53 (m, 2H), 7.34 (d, J=8.6 Hz, 1H), 5.49 (s, 1H), 4.52 (s, 1H), 4.12-4.20 (m, 1H), 3.70-3.77 (m, 1H), 2.60-2.68 (m, 1H), 2.31-2.43 (m, 1H), 2.07-2.20 (m, 3H), 1.89-1.95 (m, 1H), 1.62-1.69 (m, 1H). $^{19}$F NMR (376 MHz, DMSO-$d_6$) δ −110.92, −112.37.

Example 21: (3S,9aR)-7-(3-chloro-2-fluoro-6-(1H-tetrazol-1-yl)phenyl)-5-oxo-N-(quinoxalin-6-yl)-2,3,5,8,9,9a-hexahydro-1H-pyrrolo[1,2-a]azepine-3-carboxamide

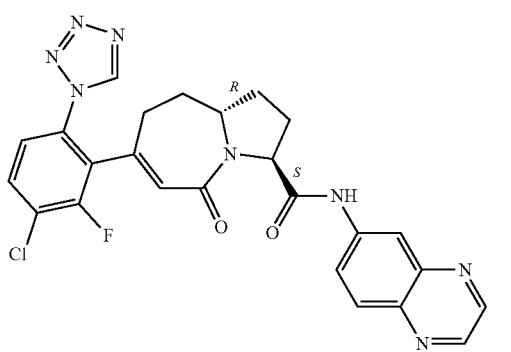

(ID No. 18)

LC/MS: mass calculated for $C_{25}H_{20}ClFN_8O_2$: 518.14, measured (ES, m/z): 519.15 [M+H]$^+$. $^1$H NMR (400 MHz, DMSO-$d_6$) δ 10.68 (s, 1H), 9.80 (s, 1H), 8.80-8.92 (m, 2H), 8.48-8.57 (m, 1H), 8.04-8.08 (m, 1H), 7.91-7.96 (m, 1H), 7.80-7.86 (m, 1H), 7.59-7.62 (m, 1H), 5.51 (s, 1H), 4.61-4.64 (m, 1H), 4.12-4.24 (m, 1H), 3.72-3.81 (m, 1H), 2.56-2.68 (m, 1H), 2.37-2.46 (m, 1H), 2.11-2.27 (m, 3H), 1.95-2.02 (m, 1H), 1.67-1.73 (m, 1H). $^{19}$F NMR (376 MHz, DMSO-$d_6$) δ −114.01.

Example 22: (3S,9aS)-7-(3-chloro-2-fluoro-6-(1H-tetrazol-1-yl)phenyl)-N-(2-(difluoromethyl)-2H-indazol-5-yl)-5-oxo-2,3,5,8,9,9a-hexahydro-1H-pyrrolo[1,2-a]azepine-3-carboxamide

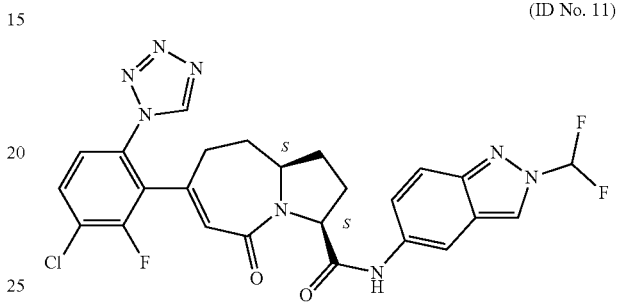

(ID No. 11)

LC/MS: mass calculated for $C_{25}H_{20}ClF_3N_8O_2$: 556.13, measured (ES, m/z): 557.15 [M+H]$^+$. $^1$H NMR (400 MHz, DMSO-$d_6$) δ 10.23 (s, 1H), 9.84 (s, 1H), 8.76 (s, 1H), 8.27-8.32 (m, 1H), 8.08-8.10 (m, 1H), 7.89-7.98 (m, 1H), 7.65-7.72 (m, 2H), 7.36 (dd, J=9.4, 2.0 Hz, 1H), 5.73-5.76 (m, 1H), 4.47-4.54 (m, 1H), 3.49-3.57 (m, 1H), 2.67-2.78 (m, 1H), 2.29-2.39 (m, 1H), 2.11-2.19 (m, 2H), 1.91-2.07 (m, 3H), 1.71-1.82 (m, 1H). $^{19}$F NMR (376 MHz, DMSO-$d_6$) δ −94.24, −114.03.

Example 23: (3S,9aR)-7-(3-chloro-2-fluoro-6-(1H-tetrazol-1-yl)phenyl)-N-(2-(difluoromethyl)-2H-indazol-5-yl)-5-oxo-2,3,5,8,9,9a-hexahydro-1H-pyrrolo[1,2-a]azepine-3-carboxamide

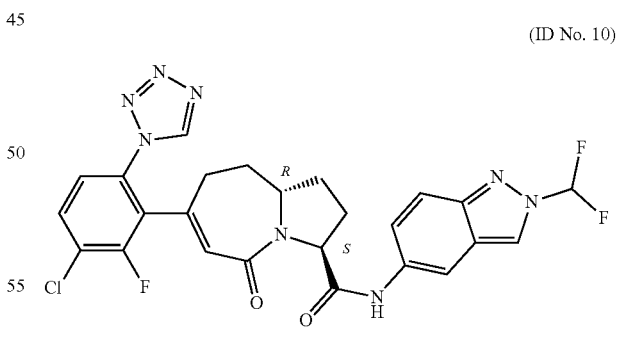

(ID No. 10)

LC/MS: mass calculated for $C_{25}H_{20}ClF_3N_8O_2$: 556.13, measured (ES, m/z): 557.15 [M+H]$^+$. $^1$H NMR (400 MHz, DMSO-$d_6$) δ 10.21 (s, 1H), 9.79 (s, 1H), 8.77 (s, 1H), 8.31 (s, 1H), 8.08-8.11 (m, 1H), 7.84 (t, J=8.2 Hz, 1H), 7.69 (d, J=9.4 Hz, 1H), 7.60 (d, J=8.8 Hz, 1H), 7.32-7.43 (m, 1H), 5.50 (s, 1H), 4.56-4.61 (m, 1H), 4.18-4.21 (m, 1H), 3.71-3.76 (m, 1H), 2.54-2.65 (m, 2H), 2.04-2.21 (m, 3H), 1.89-1.99 (m, 1H), 1.64-1.71 (m, 1H). $^{19}$F NMR (376 MHz, DMSO-$d_6$) δ −94.24, −112.33.

Biological and Formulation Examples

Biological Example 1: Factor XIa Inhibition Assay Utilizing a Fluorophore-Quencher Pair Peptide Substrate A fluorescence intensity (FLINT) based assay was used to monitor inhibition of Factor XIa. The peptide substrate, 5Fam-KLTRAETV-K5Tamra (purchased from New England Peptide) was chosen based on the FXI sequence. Conversion of zymogen FXI to its activated form, FXIa, occurs by proteolytic cleavage by FXIa at two sites, Arg146 and Arg180. The custom peptide used in this assay was based on the Arg146 cleavage site of FXI. The peptide substrate was designed with a fluorophore-quencher pair, where the fluorescence is quenched until FXIa cleaves the 8-mer peptide after the Arg residue. The substrate $K_M$ was fit to a substrate inhibition model whereby $k_{cat}$=0.86 s$^{-1}$, $K_M$=12.4 µM, $K_i$=61.6 µM with an enzymatic efficiency, and $k_{cat}/K_M$=69523 M$^{-1}$s$^{-1}$.

The Factor XIa FLINT assay was used with the following 5Fam-KLTRAETV-K5Tamra assay buffer: 50 mM Tris, pH 7.5, 100 mM NaCl, 5 mM CaCl$_2$, 0.1 mg/mL BSA, 0.03% CHAPS. Assay buffer was prepared by mixing all ingredients fresh. 5Fam-KLTRAETV-K5Tamra peptide substrate was first prepared at 10 mM in 100% DMSO, then diluted to 3 mM in 100% DMSO. Assay buffer was then added directly to the 3 mM stock of substrate to prepare the 30 µM 2× working concentration (15 µM final concentration). The 2× Factor XIa stock solution was prepared by diluting 6.562 µM stock in 1× assay buffer for a 200 µM working stock solution (100 µM final concentration).

Test compound(s) were run in an 11-point, 3-fold serial dilution with a final top compound concentration of 100 nM. Final DMSO in assay was 2%. FXIa was preincubated with compound for 30-minutes and then substrate was added to initiate the reaction. The assay was run with kinetic (KIN) reads at 5 min intervals over 30 minutes. The time course was linear using 100 µM FXIa greater than 30 minutes. More specifically, the assay was run as follows:
- 100 nL of 0.01 mM test compound was dispensed into black 384-well non-binding Greiner BioOne 784900 plate for 0.1 µM final concentration;
- 5 µL of 1× assay buffer was dispensed to column 24 (low control) and 5 µL 2× FactorXIa solution was dispensed to columns 1-23 (column 23 high control);
- the plate was centrifuged with a "cover" plate at 500 rpm for 1 min
- the plate was pre-incubated for 30 minutes at room temperature with plate covered;
- 5 µL of 2× 5Fam-KLTRAETV-K5Tamra peptide substrate was dispensed into the entire plate, columns 1-24;
- the plate was centrifuged with a "cover" plate at 500 rpm for 1 min;
- the plate was read monitoring fluorescence intensity on the BMG PHERAStar at room temperature, using fluorescence module 485 nm/520 nm.

Percent inhibition (IC$_{50}$) curves were generated per compound tested, and data was analyzed using a 4-parameter logistic fit using GeneData Screener. The relative fluorescence unit (RFU) values were normalized to percent inhibition using the following equation:

$$\% \text{ inhibition} = ((HC-LC) - (\text{compound} - LC)/(HC-LC)) * 100$$

where LC—low control=mean signal of no Factor XIa or 100% inhibition of Factor XIa; HC—high control=mean signal of Factor XIa+5Fam-KLTRAETV-K5Tamra peptide substrate with DMSO only.

An 11-point dose response curve for the test compound(s) was generated using GENDATA to determine IC$_{50}$ value based on the following equation:

$$Y = \text{Bottom} + (\text{Top} - \text{Bottom})/(1 + 10^{((\log IC_{50} - X)*\text{HillSlope})})$$

where Y is the % inhibition in the presence of X inhibitor concentration, Top=high control=mean signal of Factor XIa+5Fam-KLTRAETV-K5Tamra peptide substrate with DMSO only; Bottom=low control=mean signal of no Factor XIa or 100% inhibition of Factor XIa; HillSlope=Hill coefficient; and IC50=concentration of compound with 50% inhibition in relation to top/high control.

Biological Example 2: Kallikrein Inhibition Assay Utilizing a Quenched AMC Peptide Substrate A fluorescence intensity (FLINT) based assay was used to monitor inhibition of human plasma kallikrein. The peptide substrate, Z-Gly-Pro-Arg-AMC (Purchased from Bachem; Catalog #I-1150) was chosen based on its relatively low $K_M$ for kallikrein which enables running the assay at lower substrate concentrations to control background fluorescence. The kinetic parameters for this substrate were determined by fitting titration data to the Michaelis-Menten equation yielding a $K_M$=40 µM, $k_{cat}$=0.76 s$^{-1}$, and $k_{cat}/K_M$=18932 M$^{-1}$s$^{-1}$.

The Kallikrein FLINT assay was used with the following Z-Gly-Pro-Arg-AMC assay buffer: 50 mM Tris, pH 7.5, 100 mM NaCl, 5 mM CaCl$_2$, 0.1 mg/mL BSA, 0.03% CHAPS. Assay buffer was prepared by mixing all ingredients fresh. 2× Z-Gly-Pro-Arg-AMC peptide substrate was prepared by diluting 10 mM stock into 1× assay buffer for a 100 µM working concentration (50 µM final concentration). The 2× kallikrein stock solution was prepared by diluting 14.76 µM stock in 1× assay buffer for a 4 nM working stock solution (2 nM final concentration).

Test compound(s) were run in an 11-point, 3-fold serial dilution with a final top compound concentration of 1 µM. Final DMSO in assay was 2%. Plasma kallikrein was pre-incubated for 30-minute with compound and then 50 µM substrate was added to initiate the reaction. The assay was run with kinetic (KIN) reads at 5 min intervals over 30 minutes. The time course was linear using 2 nM kallikrein greater than 30 minutes. More specifically, the assay was run as follows:
- 100 nL of 0.1 mM test compound was dispensed into black 384-well non-binding Greiner BioOne 784900 plate for 1 µM final concentration;
- 5 µL of 1× assay buffer was dispensed to columns 24 (low control) and 5 µL 2× human kallikrein enzyme solution was dispensed to columns 1-23 (column 23 high control);
- the plate was centrifuged with a "cover" plate at 500 rpm for 1 min
- the plate was pre-incubated for 30 minutes at room temperature with plate covered;
- 5 µL of 2× Z-Gly-Pro-Arg-AMC peptide substrate was dispensed into the entire plate, columns 1-24;
- the plate was centrifuged with a "cover" plate at 500 rpm for 1 min;
- the plate was read monitoring fluorescence intensity on the BMG PHERAStar at room temperature, using fluorescence module 340 nm/440 nm.

Percent inhibition (IC$_{50}$) curves were generated per compound tested, and data was analyzed using a 4-parameter logistic fit using GeneData Screener. The relative fluorescence unit (RFU) values were normalized to percent inhibition using the following equation:

% inhibition=((HC−LC)−(compound−LC)/(HC−LC))*100 where LC—low control=mean signal of human kallikrein enzyme or 100% inhibition of human kallikrein enzyme; HC—high control=mean signal of Factor XIa+Z-Gly-Pro-Arg-AMC peptide substrate with DMSO only.

An 11-point dose response curve for the test compound(s) was generated using GENDATA to determine IC$_{50}$ value based on the following equation:

Y=Bottom+(Top−Bottom)/(1+10^((log IC$_{50}$−X)*HillSlope))

where Y is the % inhibition in the presence of X inhibitor concentration, Top=high control=mean signal of human kallikrein enzyme+Z-Gly-Pro-Arg-AMC peptide substrate with DMSO only; Bottom=low control−mean signal of no human kallikrein enzyme or 100% inhibition of human kallikrein enzyme; HillSlope=Hill coefficient; and IC$_{50}$=concentration of compound with 50% inhibition in relation to top/high control.

Representative compounds of formula (I) of the present invention were tested according to the procedure described in Biological Example 1 and Biological Example 2 above, with results as listed in Table 3, below.

TABLE 3

Biological Activity, Representative Compounds of Formula (I)

| ID No. | Factor XIa IC$_{50}$ (nM) | Factor XIa Ki (nM) | Kallikrein IC$_{50}$ (nM) |
|---|---|---|---|
| 1 | >100 | >50 | 227.9 |
| 2 | 8.9 | 4.4 | 12.2 |
| 3 | 60.9 | 30.4 | 779.7 |
| 4 | 19.9 | 9.9 | 38.7 |
| 5 | 82.1 | 41.0 | 143.7 |
| 6 | 24.2 | 12.1 | 160.1 |
| 7 | 55.8 | 27.9 | 348.1 |
| 8 | 18.7 | 9.4 | 13.9 |
| 9 | 24.3 | 12.1 | 42.8 |
| 10 | >100 | >50 | 245.9 |
| 11 | 8.8 | 4.4 | 29.4 |
| 12 | 9.9 | 5.0 | 32.4 |
| 13 | >100 | >50 | 800.8 |
| 14 | >100 | >50 | 234.6 |
| 15 | 39.9 | 20.0 | 61.7 |
| 16 | 20.0 | 10.0 | 29.5 |
| 17 | 33.4 | 16.7 | 97.1 |
| 18 | 71.9 | 35.9 | 89.8 |
| 19 | 6.9 | 3.5 | 14.0 |
| 20 | >100 | >50 | 801.7 |
| 21 | 13.9 | 6.9 | 112.4 |
| 22 | >100 | >50 | 892.1 |
| 23 | 27.0 | 13.5 | 57.7 |

Formulation Example 1

Solid, Oral Dosage Form—Prophetic Example

As a specific embodiment of an oral composition, 100 mg of Compound ID No. 15 or ID No. 3, prepared as described in Example 1 and 2, respectively, is formulated with sufficient finely divided lactose to provide a total amount of 580 to 590 mg to fill a size O hard gel capsule.

While the foregoing specification teaches the principles of the present invention, with examples provided for the purpose of illustration, it will be understood that the practice of the invention encompasses all of the usual variations, adaptations and/or modifications as come within the scope of the following claims and their equivalents.

Throughout this application, various publications are cited. The disclosure of these publications is hereby incorporated by reference into this application to describe more fully the state of the art to which this invention pertains.

What is claimed:
1. A compound of formula (I):

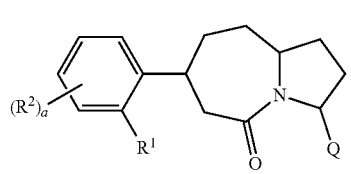

(I)

or a pharmaceutically acceptable salt or stereoisomer thereof,
wherein:
Q is C(O)NHR$^6$ or

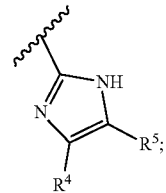

R$^1$ is halogen, CN, NO$_2$, C$_{1-4}$ alkyl, C$_{1-4}$ fluoroalkyl, C(O)C$_{1-4}$ alkyl, NR$^A$R$^B$, OH, OC$_{1-4}$ alkyl, OC$_{1-4}$ fluoroalkyl, C$_{3-6}$ cycloalkyl, phenyl, or 5- or 6-membered heterocyclyl, wherein the C$_{3-6}$ cycloalkyl, phenyl, or 5- or 6-membered heterocyclyl is optionally substituted with one or more substituents independently selected from the group consisting of halogen, CN, C$_{1-4}$ alkyl, C$_{1-4}$ fluoroalkyl, C$_{1-4}$ alkylene-NR$^A$R$^B$, C(O)OH, C(O)OC$_{1-4}$ alkyl, NR$^A$R$^B$, OH, OC$_{1-4}$ alkyl, OC$_{1-4}$ fluoroalkyl, C$_{3-7}$ cycloalkyl, and 5- or 6-membered heterocyclyl;
each R$^2$ is independently F, Cl, CH$_3$, or OCH$_3$;
R$^4$ is H or halogen;
R$^5$ is phenyl or 5- or 6-membered heteroaryl, wherein the phenyl or 5- or 6-membered heteroaryl is optionally substituted with one or two substituents independently selected from the group consisting of halogen, C$_{1-4}$ alkyl, C$_{1-2}$ fluoroalkyl, C$_{1-2}$ hydroxyalkyl, C(O)NR$^C$R$^D$, C(O)OH, C(O)OC$_{1-4}$ alkyl, NR$^A$R$^B$, and NR$^C$C(O)C$_{1-2}$ alkyl;
R$^6$ is phenyl or 9- or 10-membered heteroaryl, wherein the phenyl or 9- or 10-membered heteroaryl is optionally substituted with one or two substituents independently selected from the group consisting of halogen, C$_{1-4}$ alkyl, C$_{1-2}$ fluoroalkyl, C$_{1-2}$ hydroxyalkyl, C(O)NR$^E$R$^F$, C(O)OH, C(O)OC$_{1-4}$ alkyl, Nine, and NR$^C$C(O)C$_{1-2}$ alkyl;
each R$^A$ is independently H or C$_{1-4}$ alkyl;
each R$^B$ is independently H or C$_{1-4}$ alkyl;

each $R^C$ is independently H, $C_{1-2}$ alkyl, or $C_{1-4}$ hydroxyalkyl;
each $R^D$ is independently H, $C_{1-2}$ alkyl, or $C_{1-4}$ hydroxyalkyl;
each $R^E$ is independently H or $C_{1-4}$ alkyl;
each $R^F$ is independently H or $C_{1-4}$ alkyl; and
a is 0, 1, 2, or 3.

2. The compound of claim 1, or a pharmaceutically acceptable salt or stereoisomer thereof, wherein:
$R^1$ is halogen, $C_{1-4}$ alkyl, $C_{1-2}$ fluoroalkyl, OH, $OC_{1-4}$ alkyl, $OC_{1-2}$ fluoroalkyl, $C_{3-6}$ cycloalkyl, phenyl, or 5- or 6-membered heterocyclyl, wherein the $C_{3-6}$ cycloalkyl, phenyl, or 5- or 6-membered heterocyclyl is optionally substituted with one or two substituents independently selected from the group consisting of halogen, $C_{1-4}$ alkyl, $C_{1-2}$ fluoroalkyl, C(O)OH, C(O)OC$_{1-4}$ alkyl, OH, $OC_{1-4}$ alkyl, and $OC_{1-2}$ fluoroalkyl;
$R^6$ is phenyl or 9- or 10-membered heteroaryl, wherein the phenyl or 9- or 10-membered heteroaryl is optionally substituted with one or two substituents independently selected from the group consisting of halogen, $C_{1-4}$ alkyl, $C_{1-2}$ fluoroalkyl, $C_{1-2}$ hydroxyalkyl, C(O)NR$^E$R$^F$, C(O)OH, and C(O)OC$_{1-4}$ alkyl;
each $R^E$ is independently H or $C_{1-2}$ alkyl;
each $R^F$ is independently H or $C_{1-2}$ alkyl; and
a is 0, 1, or 2.

3. The compound of claim 1, or a pharmaceutically acceptable salt or stereoisomer thereof, wherein:
$R^1$ is $C_{1-4}$ fluoroalkyl or 5- or 6-membered heterocyclyl, wherein the 5- or 6-membered heterocyclyl is optionally substituted with one or more independently selected $C_{1-4}$ fluoroalkyl substituents;
each $R^2$ is independently F or Cl;
$R^4$ is H or F;
$R^5$ is phenyl or 6-membered heteroaryl, wherein the phenyl or 6-membered heteroaryl is optionally substituted with one or two substituents independently selected from the group consisting of halogen, $C_{1-2}$ hydroxyalkyl, C(O)NR$^C$R$^D$, C(O)OH, NR$^C$R$^D$, and NR$^C$C(O)C$_{1-2}$ alkyl;
$R^6$ is phenyl or 9- or 10-membered heteroaryl, wherein the phenyl or 9- or 10-membered heteroaryl is optionally substituted with one or two substituents independently selected from the group consisting of halogen, $C_{1-2}$, fluoroalkyl, C(O)NR$^E$R$^F$, and C(O)OH;
each $R^E$ is independently H or $C_{1-2}$ alkyl;
each $R^F$ is independently H or $C_{1-2}$, alkyl; and
a is 1 or 2.

4. The compound of claim 1, or a pharmaceutically acceptable salt or stereoisomer thereof, wherein:

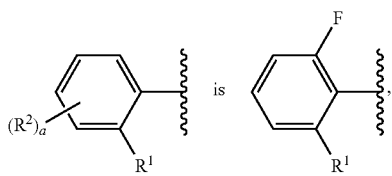 is 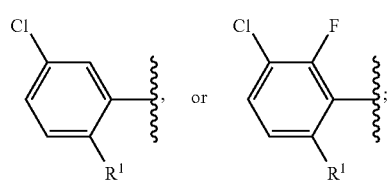, $R^1$ is OCHF$_2$, 4-(trifluoromethyl)-1,2,3-triazol-1-yl, or tetrazol-1-yl;
$R^4$ is H or F;
$R^5$ is:

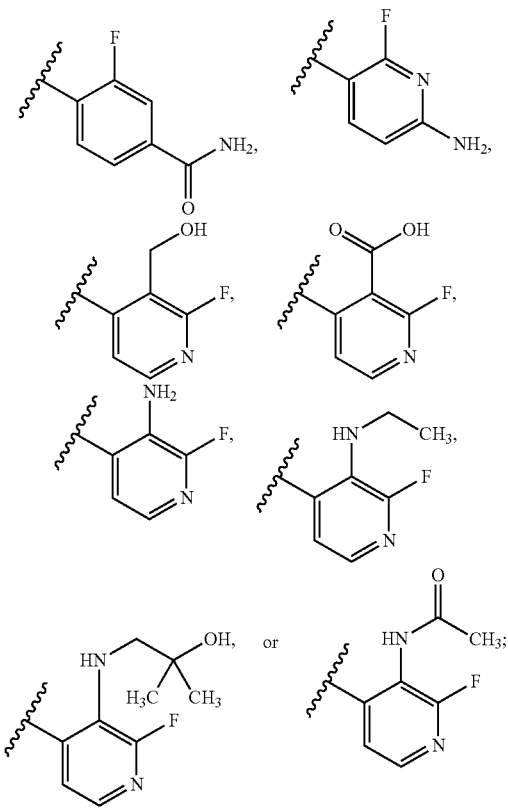

and
$R^6$ is:

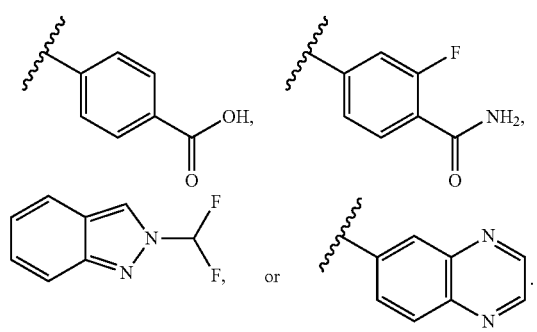

5. The compound of claim 1, or a pharmaceutically acceptable salt or stereoisomer thereof, wherein:

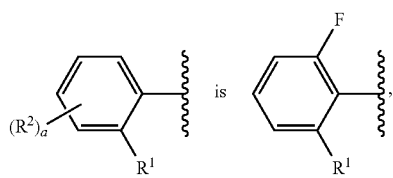

-continued

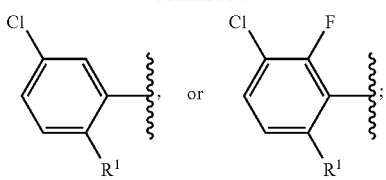

R[1] is OCHF$_2$, 4-(trifluoromethyl)-1,2,3-triazol-1-yl, or tetrazol-1-yl;
R[4] is H or F; and
R[5] is:

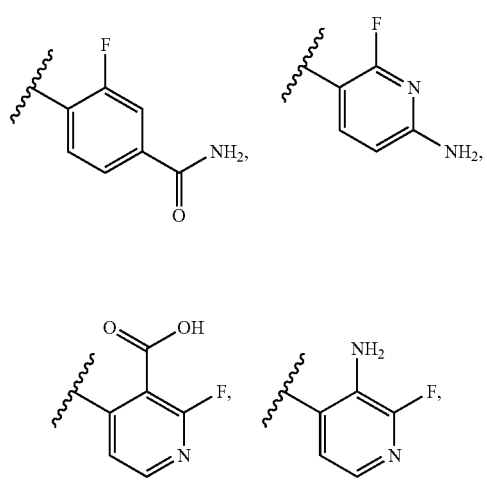

and
R[6] is:

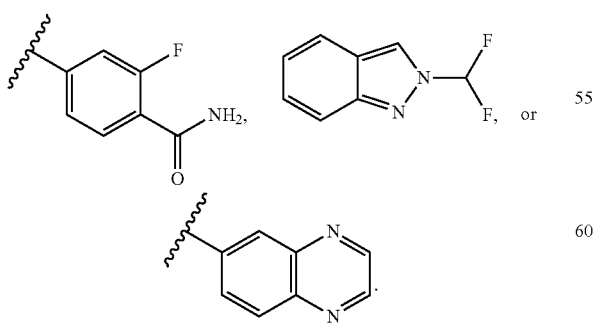

6. The compound of claim 1, or a pharmaceutically acceptable salt or stereoisomer thereof, wherein:

Q is C(O)NHR[6];

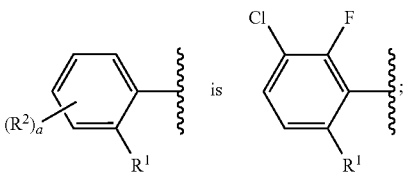

R[1] is OCHF$_2$ or tetrazol-1-yl; and
R[6] is:

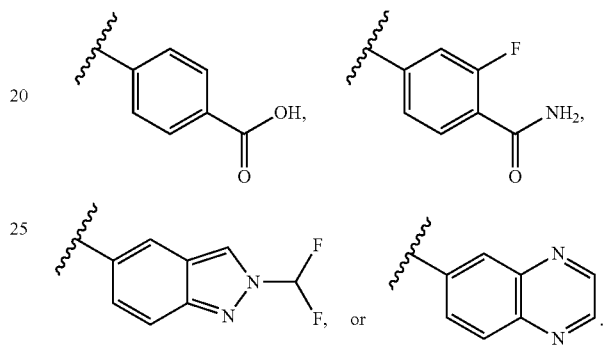

7. The compound of claim 1, or a pharmaceutically acceptable salt or stereoisomer thereof, wherein:

Q is

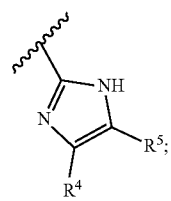

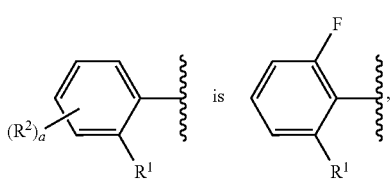

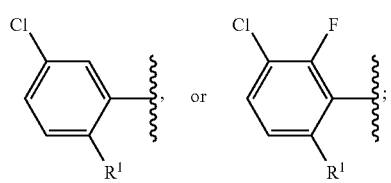

R[1] is 4-(trifluoromethyl)-1,2,3-triazol-1-yl or tetrazol-1-yl;
R[4] is H or F; and $R^5$ is:

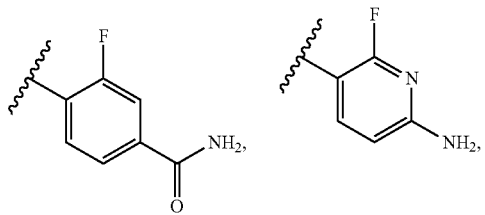

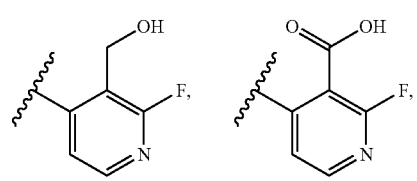

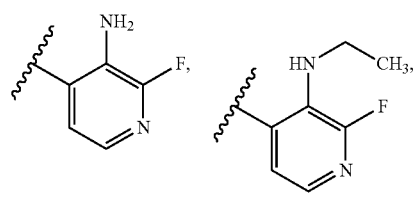

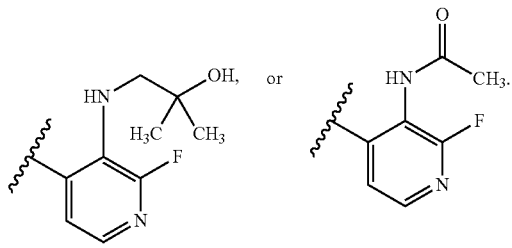

8. The compound of claim 1, or a stereoisomer thereof, wherein the compound, or stereoisomer thereof, is selected from the group consisting of:

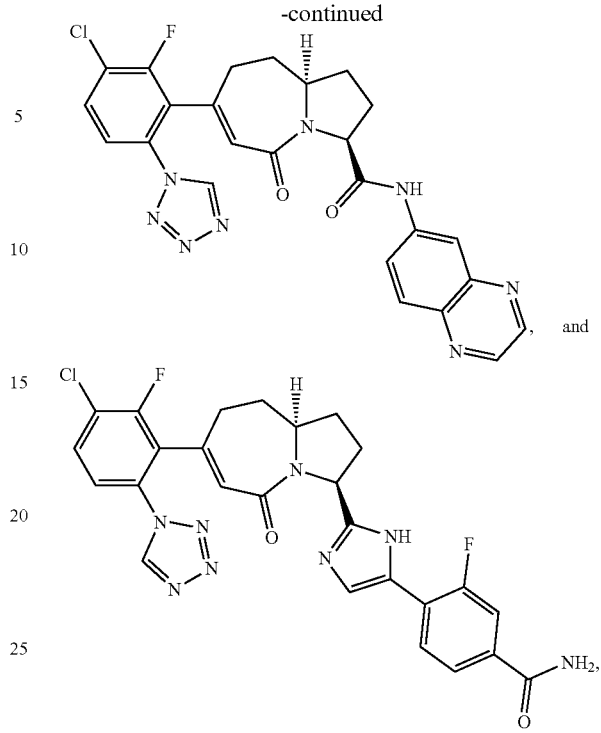

or a pharmaceutically acceptable salt thereof.

9. A pharmaceutical composition comprising a pharmaceutically acceptable carrier and a compound of claim 1, or a pharmaceutically acceptable salt or stereoisomer thereof.

10. A method for inhibiting plasma kallikrein activity in a subject, wherein the method comprises administering to the subject in need thereof a therapeutically effective amount of a compound of claim 1, or a pharmaceutically acceptable salt or stereoisomer thereof.

11. The method of claim 10, wherein the subject has a condition or disease in which plasma kallikrein activity is implicated selected from the group consisting of adult respiratory distress syndrome, arthritis, cancer, cardiomyopathy, cardiopulmonary bypass surgery, diabetes, diabetic macular edema, diabetic retinopathy, disseminated intravascular coagulation, hereditary angioedema, hypotension, impaired visual acuity, inflammation, inflammatory bowel disease, nephropathy, neuropathy, pancreatitis, and septic shock.

12. The method of claim 10, wherein the subject has a disease or disorder selected from the group consisting of an inflammatory disease, an inflammatory disorder, and a thromboembolic disorder.

13. The method of claim 12, wherein the inflammatory disorder is selected from the group consisting of acute respiratory distress syndrome, sepsis, and systemic inflammatory response syndrome.

14. The method of claim 12, wherein the thromboembolic disorder is selected from the group consisting of an arterial cardiovascular thromboembolic disorder, a venous cardiovascular thromboembolic disorder, an arterial cerebrovascular thromboembolic disorder, and a venous cerebrovascular thromboembolic disorder.

15. The method of claim 12, wherein the thromboembolic disorder is selected from the group consisting of an acute coronary syndrome, arterial embolism, atherosclerosis, atrial fibrillation, cerebral arterial thrombosis, cerebral embolism, coronary arterial thrombosis, deep vein thrombosis, first myocardial infarction, ischemic sudden death, kidney embolism, peripheral occlusive arterial disease, pulmonary embolism, recurrent myocardial infarction, stroke, thrombophlebitis, thrombosis resulting from cardiopulmonary bypass, thrombosis resulting from hemodialysis, thrombosis resulting from an implant, thrombosis resulting from an indwelling catheter, thrombosis resulting from a prosthetic valve, thrombosis resulting from a stent, transient ischemic attack, unstable angina, and venous thrombosis.

16. The method of claim 12, wherein the thromboembolic disorder is diabetic macular edema (DME) or hereditary angioedema (HAE).

\* \* \* \* \*